United States Patent
Ashley et al.

(10) Patent No.: US 6,492,562 B1
(45) Date of Patent: Dec. 10, 2002

(54) RACEMIC THIOESTERS FOR PRODUCTION OF POLYKETIDES

(75) Inventors: Gary Ashley, Alameda, CA (US); Isaac C. Chan-Kai, Hayward, CA (US); Mark A. Burlingame, San Francisco, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/492,733

(22) Filed: Jan. 27, 2000

Related U.S. Application Data
(60) Provisional application No. 60/117,384, filed on Jan. 27, 1999.

(51) Int. Cl.$^7$ .............................................. C07C 11/00
(52) U.S. Cl. ..................................... 568/75; 424/70.51
(58) Field of Search .......................... 424/70.51; 568/75

(56) References Cited

U.S. PATENT DOCUMENTS

| | | | |
|---|---|---|---|
| 5,824,513 A | 10/1998 | Katz et al. | 453/76 |
| 6,004,787 A | 12/1999 | Katz et al. | 453/183 |

FOREIGN PATENT DOCUMENTS

| | | |
|---|---|---|
| WO | WO 99 03986 | 1/1999 |

OTHER PUBLICATIONS

Harris et al., "Enantiospecific Synthesis of Analogs of the Diketide Intermediate of the Erythromycin Polyketide Synthase (PKS)" (1998) J. Chem. Res., Synop., (6), 283.

Cane et al., "Macrolide Biosynthesis. 4. Intact Incorporation of a Chain–Elongation Intermediate into Erythromycin," *J Am Chem Soc* (1987) 109:1255–1257.

Cane et al., "Macrolide Biosynthesis. 7. Incorporation of Polyketide Chain Elongation Intermediates into Methymycin," *J Am Chem Soc* (1993) 115:522–526.

Cane et al., "Nargenicin Biosynthesis. Incorporation of Polyketide Chain Elongation Intermediates and Support for a Proposed Intramolecular Diels–Alder Cyclization," *J Am Chem Soc* (1993) 115:527–535.

Cane et al., "Erythromycin Biosynthesis. Highly Efficient Incorporation of Polyketide Chain Elongation Intermediates into 6–Deoxyerythronolide B in an Engineered Streptomyces Host," *J Antibiotics* (1995) 48:647–651.

Dutton et al., "Novel Avermectins Produced by Mutational Biosynthesis," *J Antibiotics* (1991) 44:357–365.

Evans et al., "Contrasteric Carboximide Hydrolysis with Lithium Hydroperoxide," *Tetrahedron Lett* (1987) 28:6141.

Evans et al., "Directed Reduction of β–Hydroxy Ketones Employing Tetramethylammonium Triacetoxyborohydride," *J Am Chem Soc* (1988) 110:3560–3578.

Evans et al., "Diastereoselective Aldol Reactions Using β–Keto Imide Derived Enolates. A Versatile Approach to the Assemblage of Polypropionate Systems," *J Am Chem Soc* (1990) 112:866–868.

Evans et al., "Diastereoselective Anti Aldol Reactions of Chiral Ethyl Ketones. Enantioselective Processes for the Synthesis of Polypropionate Natural Products," *Tetrahedron Lett* (1992) 48:2127–2142.

Jacobsen et al., "Precursor–Directed Biosynthesis of Erythromycin Analogs by an Engineered Polyketide Synthase," *Science* (1997) 277:367–369.

Kao et al., "Engineered Biosynthesis of a Triketide Lactone from an Incomplete Modular Polyketide Synthase," *J Am Chem Soc* (1994) 116:11612–11613.

Marsden et al., "Engineering Broader Specificity into an Antibiotic–Producing Polyketide Synthase," *Science* (1998) 279:199–202.

Miyata et al., "An Efficient Method for Removal of Chiral Auxiliaries, Camphorsultam and 4–Isopropyl–2–Oxazolidinone," *Syn Lett* (1994) 637–638.

Kao et al., "Evidence for Two Catalytically Independent Clusters of Active Sites in a Functional Modular Polyketide Synthase," *Biochemistry* (1996) 35(38):12363–12368.

Sann et al., "A General Synthesis of Homochiral β–Hydroxy N–Acetylcysteamine Thioesters," *Tetrahedron Letters* (1999) 40(21):4093–4096.

Kira J. Weissman et al., "Evaluating Precursor–directed Biosynthesis Towards Novel Erythromycins through in vitro Studies on a Bimodular Polyketide Synthase", Chemistry and Biology (1998) 5:743–754.

Christopher J. Dutton et al., "Avermectin Biosynthesis. Intact Incoporation of a Diketide Chain–Assembly Intermediate Into the Polyketide Macrocyclic Ring", Tetrahedron Letters (1994) 35:327–330.

*Primary Examiner*—Jon P. Weber
(74) *Attorney, Agent, or Firm*—Kate H. Murashige; Gary Ashley; Kevin Kaster

(57) ABSTRACT

Facile methods for preparing diketide and triketide thioesters are disclosed. The resulting thioesters may be used as intermediates in the synthesis of desired polyketides, and may contain functional groups which ultimately reside in side chains on the resulting polyketide and thus can be used further to manipulate the polyketide so as form derivatives. The polyketides produced may also be tailored by glycosylation, hydroxylation and the like. New polyketides and their derivatives and tailored forms are thereby produced.

17 Claims, 8 Drawing Sheets anti-aldol
(not observed)

syn-aldol

RACEMIC THIOESTERS FOR PRODUCTION OF POLYKETIDES

This application claims priority under 35 U.S.C. §119 from U.S. Ser. No. 60/117,384 filed Jan. 27, 1999. The contents of this application are incorporated herein by reference.

TECHNICAL FIELD

The invention concerns methods for the efficient synthesis of oligoketide thioesters, including diketide and triketides, which are useful as intermediates in polyketide production and to methods to use these intermediates. The methods of synthesis are suitable for liquid phase as well as solid-phase combinatorial synthesis. The invention also includes polyketide and tailored polyketide products.

BACKGROUND OF THE INVENTION

The creation of novel macrolide polyketides has been achieved through genetic manipulation of polyketide synthases. The modular nature of the Type 1 polyketide synthases allows for domain exchange between different polyketide synthase genes, resulting in hybrid genes which produce polyketide synthases with altered properties that result, in turn, in modified macrolide structures. Thus, it is possible to control chain length, choice of chain extender unit, degree of β-carbon oxidation level, and to some degree stereochemistry. The choice of starter unit has been more difficult to control. Two complementary approaches have been described.

Dutton, et al., *J. Antibiotics* (1991) 44:357–365 demonstrated that the avermectin polyketide synthase was somewhat flexible in choice of starter units. When denied the natural starter unit through inactivation of the branched-chain amino acid dehydrogenase, the avermectin polyketide synthase will accept a variety of α-branched carboxylic acids as the starter unit. However, only about 30 acids out of nearly 800 candidate acids tried were accepted. Acids without an α-branch appear to be metabolized through β-oxidation until an α-branch is reached, further limiting this methodology. Marsden, et al., *Science* (1998) 79:199–202 exchanged the native loading domain of the erythromycin PKS with that from the avermectin polyketide synthase, resulting in a hybrid PKS having the same loosened starter unit specificity as the avermectin PKS. Clearly, the native specificities of enzymatic domains will always be a limitation on the flexibility of resulting hybrid systems.

A more general method for controlling starter unit specificity has been described by Jacobsen, et al., *Science* (1997) 277:367–369. Inactivation of the ketosynthase in module 1 (KS1) of the erythromycin PKS (DEBS) results in an enzyme (KS1°-DEBS) incapable of initiating polyketide synthesis using precursors normally available to the cell. When supplied with a suitable thioester of the diketide product of module 1 or its analogs, however, KS1°-DEBS efficiently incorporates these into full-length polyketides. Subsequent experiments have demonstrated that a very wide range of diketide analogs are accepted by KS1°-DEBS, making this a very general method for production of analogs of the polyketide precursor of erythromycin, 6-deoxyerythronolide B (6-dEB), with variations at the positions controlled by the starter unit. Further, this method allows for production of 6-dEB analogs altered at the 12-position; this is equivalent to altering the substrate specificity of the module 1 acyltransferase (AT1) which transfers the first extender unit. While this has been accomplished through the above described domain exchange experiments as well, the "diketide method" allows for introduction of 12-position substituents which are not available from nature. Furthermore, triketide analogs are accepted, opening the 10- and 11-positions of 6-dEB for modification. The 6-dEB analogs obtained can be further converted into analogs of erythromycin by feeding to a suitable converter strain, such as a strain of *Saccharopolyspora erythraea* containing a non-functional erythromycin PKS. The resulting erythromycins have altered side-chains at the 13-position as well as other optional modifications, and show altered biological activity. These erythromycin analogs can also be produced by introducing the KS1°-mutation into an erythromycin-producing strain of *Saccharopolyspora erythraea*, then supplying the mutant strain with suitable diketide or triketide thioesters as described above.

Implementation of this method requires the availability of the N-acylcysteamine oligoketide thioesters. Synthetic methods available in the art for these thioesters do not lend themselves to efficient, economical synthesis, or to the systematic production of variants. The diketide and triketides also typically contain chiral centers requiring the control of absolute or relative stereochemistry.

Cane, D. E., et al., *J Am Chem Soc* (1987) 109:1255–1257 describes a three-step process to produce the N-acetylcysteamine thioester of (2S,3R)-2-methyl-3-hydroxy pentanoic acid. The method relies on the use of a chiral reagent N-propionyl-(4S)-4-isopropyl-2-oxazolidinone for control of the absolute stereochemistry of the product:

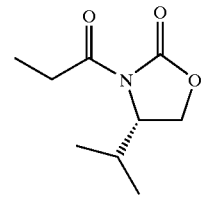

N-propionyl-(4S)-4-isopropyl-2-oxazolidinone

This material results from the acylation of (4S)-4-isopropyl-2-oxazolidinone with propionyl chloride, typically using a strong base such as n-butyllithium at low temperature. The Cane process is an aldol condensation of this starting material with propionaldehyde in the presence of dibutyl-boron triflate (Bu$_2$BOTf), followed by hydrolysis of the imide (lithium hydroperoxide) and thioesterification with N-acetylcysteamine in the presence of diphenyl phosphorylazide and triethylamine. This multi-step process is inefficient, with substantial losses accompanying the hydrolysis step.

Cane, D. E., et al., *J Antibiotics* (1995) 48:647–651 was able to improve yields using a five-step process which replaces the aldol condensation with a Claisen condensation between the lithium enolate of the propionyl oxazolidinone (N-propionyl-(4S)-4-benzyl-2-oxazolidinone was used as the stereochemistry controlling starting material in this method) and propionyl chloride followed by reduction of the resulting β-ketoester product using zinc borohydride. Protection of the β-hydroxy substituent as a tert-butyldimethylsilyl ether preceded hydrolysis of the imide, which again required lithium hydroperoxide. The protecting group gave improved yields from hydrolysis, but required an additional two steps to add and remove. This longer process also suffers from the use of zinc borohydride, which is not commercially available.

Cleavage of the N-acyloxazolidinones resulting from either aldol or Claisen condensations as described above is problematic. Various methods of cleavage are known in the art, including that of Evans, D. A., et al., *Tetrahedron Lett* (1987) 28:6141, in which undesired reaction at the oxazolidinone carbonyl during hydrolysis is suppressed by the use of lithium hydroperoxide. This process requires the use of concentrated solutions of hydrogen peroxide, which are explosive and dangerous for large-scale processes. The N-acyloxazolidinones are unreactive towards thiols or thiolates, although some conversion to thioesters can be observed using concentrated solutions of lithium thiolates in tetrahydrofuran. The low solubility of the thiolates in tetrahydrofuran combined with epimerization of chiral diketides due to the basicity of the thiolates limits the utility of this method. Miyata, O., et al., *Syn Lett* (1994) 637–638, describes conversion of N-acyloxazolidinones to S-benzylthioesters through the use of lithium benzylthiotrimethylaluminate. The production of more complex thioesters containing groups capable of binding Lewis acids like trimethylaluminum, such as those based on N-acylcysteamine, has not been reported.

The N-acetylcysteamine thioesters of larger oligoketides have also been prepared. Cane, D. E., et al., *J Am Chem Soc* (1993) 115:522–526 synthesized the N-acetylcysteamine thioester of (4S,5R)-5-hydroxy-4-methyl-2-heptenbic acid using the stereochemically controlled aldol condensation product of N-propionyl-(4S)-4-benzyl-2-oxazolidinone as the starting material:

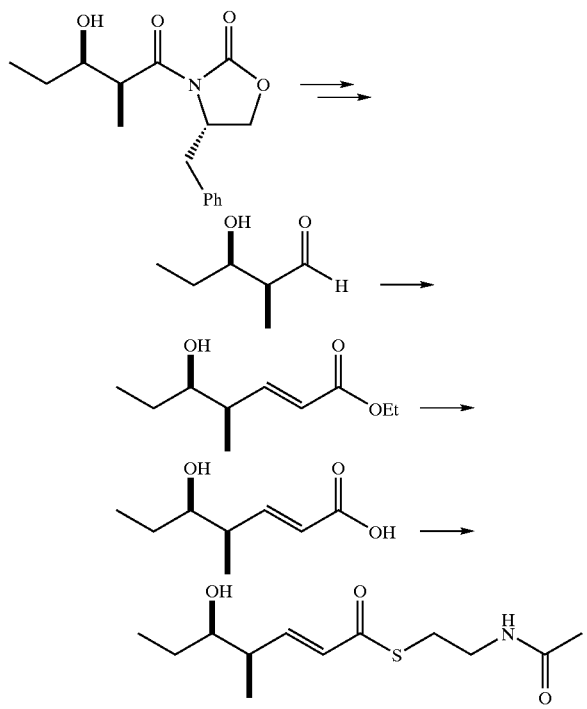

This imide was converted to the corresponding aldehyde, and extended at the carbonyl group by a Wittig reaction to obtain the desired triketide as the ethyl ester which was then hydrolyzed and converted to the acylcysteamine thioester in a two-step process. Yields were improved by addition of steps protecting the alcohol, Cane, D. E., et al., *J Am Chem Soc* (1993) 115:527–535. However, this approach clearly does not lend itself to efficient modular solid-phase synthesis since the building of the triketide chain is nonlinear—i.e., the condensations and the Wittig reactions extend the diketide in opposing directions. Each new analogrequires complete passage through the synthesis with no common intermediates.

While it is clear that thioester forms of acyl moieties, diketides and triketides can be incorporated by PKS systems, to date, little has been reported concerning the optimal thioesters to produce the desired polyketides other than that N-acetylcysteamine thioesters are generally effective as compared with the free carboxylic acids or their oxy-esters (Cane & Yan). It may be expected, however, that the nature of the thioester, e.g. the acyl group in an N-acylcysteamine thioester, might influence such important factors as water solubility, transport into the bacterial cell, metabolism, and recognition by the PKS. A synthetic method for producing variation in the thioester group itself would thus be advantageous.

The present invention offers both improved efficiency in the synthesis of optically-pure diketide thioester intermediates and an approach which provides for efficient extension of the diketides into the corresponding triketide thioesters and provides for additional condensation steps to extend the oligoketide still further. The present invention further provides a method: for synthesis of racemic rather than optically pure diketide thioesters. The racemic materials constitute low-cost alternatives for large-scale production of novel polyketides by fermentation.

DISCLOSURE OF THE INVENTION

The invention offers improvements in the synthesis of oligoketide thioester intermediates. These intermediates can then be incorporated into pathways for the synthesis of novel polyketides using native or modified polyketide synthase (PKS) systems. The invention offers an improvement in the efficiency of diketide synthesis as well as a method for synthesis of triketides and oligoketides in general which is adapted to efficient, linear, solid-phase synthesis. The invention further provides a method to produce racemic diketide thioesters in an economical manner. The invention further provides a method for producing novel polyketides suitable for further modification through the introduction of unique functionalities.

Thus, in one aspect, the invention is directed to the conversion of an acyl imide such as that of a diketide, triketide or oligoketide directly to an N-acylcysteamine thioester by treating the imide with a salt of the corresponding mercaptan. For the synthesis of optically active oligoketide thioesters starting from chiral oxazolidinones, this is done in the presence of a Lewis acid to facilitate the reaction and preserve stereochemical purity. For the synthesis of racemic oligoketide thioesters starting from achiral benzoxazolones, the Lewis acid is not required. This method obviates the intermediate steps of imide hydrolysis, alcohol protection, thioesterification, and deprotection used by previous methods. This method is particularly advantageous for solid-phase synthesis, as it allows for generation of the product with simultaneous cleavage of the oligoketide from the solid support. A particularly facile process using transthiolation of thioesters is given.

In a second aspect, the invention is directed to a method to synthesize racemic diketides and their derivatives through the titanium-mediated aldol condensation between N-acyl-2-benzoxazolones with aldehydes, followed by reaction of the aldol products with nucleophiles to yield the desired derivatives. This method provides a direct route to various oligoketide derivatives, including esters and amides, and is particularly advantageous for the multi-kilogram, economical synthesis of diketide N-acylcysteamine thioesters required for fermentation. As the relative chirality of the carbons at positions 2 and 3 of the attached acyl group is preserved, the racemic mixture will contain one isomer which can be utilized by the PKS and only one additional isomer which cannot. This is in contrast to production of the four possible diestereomerswhich would result in utilization of only one-quarter of the available molecules.

Thus, in still another aspect, the invention is directed to methods to synthesize diketides and triketides which can be used to produce macrolides with functional substituents for example at the 13- and 14-positions by employing, for example, alkenyl- or benzyloxy-aldehydes to introduce starter unit and/or first extender moiety equivalents containing derivatizable groups. The benzyloxy group can readily be converted to a hydroxyl by reduction and then mesylated to provide a suitable leaving group for replacement with nucleophiles, including halides, azides, amines, thiols, other alcohols, and cyanide. The alkenyl group can be.functionalized by any of numerous methods known in the art, including Heck coupling to introduce aryl groups. Such derivatizations can be performed either on the oligoketide or on the polyketides which are produced upon feeding of the oligoketides to suitable PKS systems or cultures of microorganisms.

In an additional aspect, the invention is directed to methods to synthesize oligoketide thioesters using solid-phase combinatorial chemistry. These methods are particularly advantageous when a library of oligoketide thioesters is desired.

In summary, because the invention permits a wide variety of diketide and triketide thioesters to be synthesized in a facile and economic manner, it is possible to prepare a wide variety of polyketides and their tailored derivatives taking advantage of the availability of both recombinant and natively produced polyketide synthase systems and tailoring enzymes, as well as employing chemical transformations using side-chain functional groups.

In still other aspects, the invention relates to feeding diketides or triketides, prepared by the methods of the invention, to suitable PKS systems in vitro or in vivo to obtain oligoketides or polyketides and further converting said polyketides to antibiotics by glycosylation and/or other modifications. The invention also relates to novel intermediates and the resulting modified polyketides and antibiotics.

MODES OF CARRYING OUT THE INVENTION

The invention provides methods useful in the synthesis of intermediates for the production of polyketides that have characteristics desirable for efficient and practical applications.

An efficient synthetic strategy for the required oligoketide thioesters should provide:

1) stereochemical control;
2) a minimum number of synthetic steps;
3) synthetic steps with high yields;
4) use of common intermediates;
5) adaptability to solid phase synthesis;
6) adaptability to combinatorial library generation.

For large-scale applications, further criteria concern the cost and availability of reagents.

Figure 1:
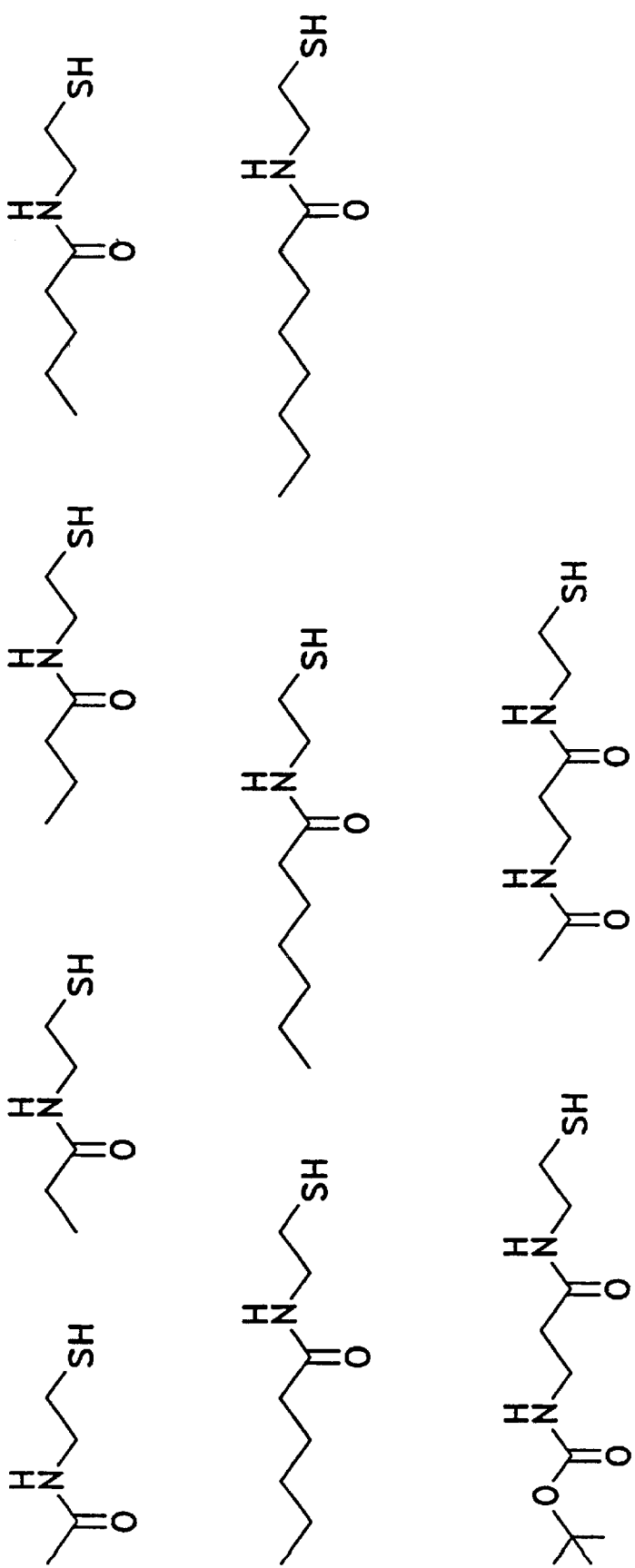
FIG. 1 sets forth structures of illustrative suitable N-acyl cysteamines.
Figure 2:
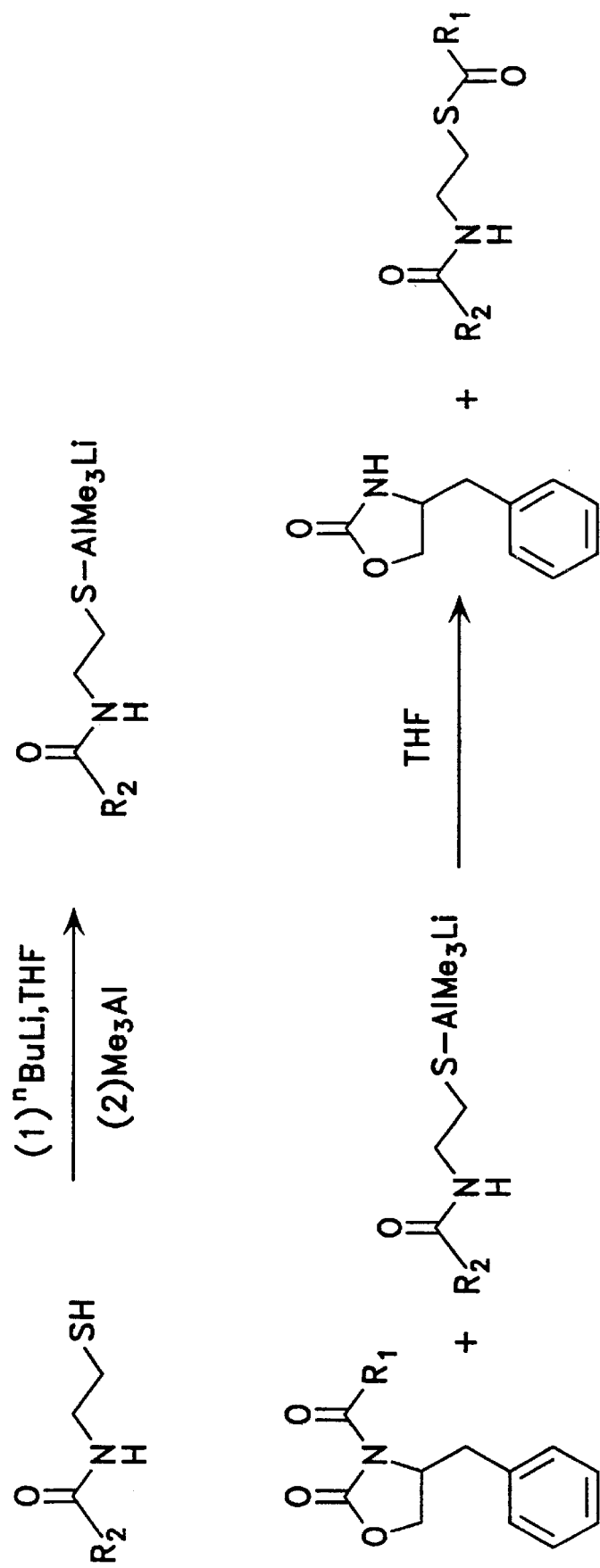
FIG. 2 illustrates the method for conversion of N-acyloxazolidinones into N-acylcysteamine thioesters.

The invention methods provide these characteristics. The crucial step in all routes to diketide thioesters is the formation of the thioester linkage. Due to low reactivity of the commonly used N-acyloxazolidinone intermediates towards thiol nucleophiles, this process usually requires several steps as described above. The oxazolidinone auxiliary is removed by hydrolysis, and the resulting acid is activated and converted into the thioester. It is possible to convert N-acyloxazolidinones into thioesters directly by treatment with the lithium salt of the mercaptan, but yields are typically low and loss of stereochemical integrity is often noted for chiral diketides. The invention provides an efficient method for direct conversion of N-acyloxazolidinones into thioesters of N-acylcysteamines which uses the trimethylaluminum complex of the lithium mercaptide (FIG. 2). This proceeds in high yields without detectable loss of stereochemical integrity. Since the filing of provisional application 60/117,384, a similar method using trimethylaluminuni with N-acetylcysteamine has been reported in C. LeSann, et al., *Tetrahedron Letters* (1999) 40:4093–4096.

Figure 3:
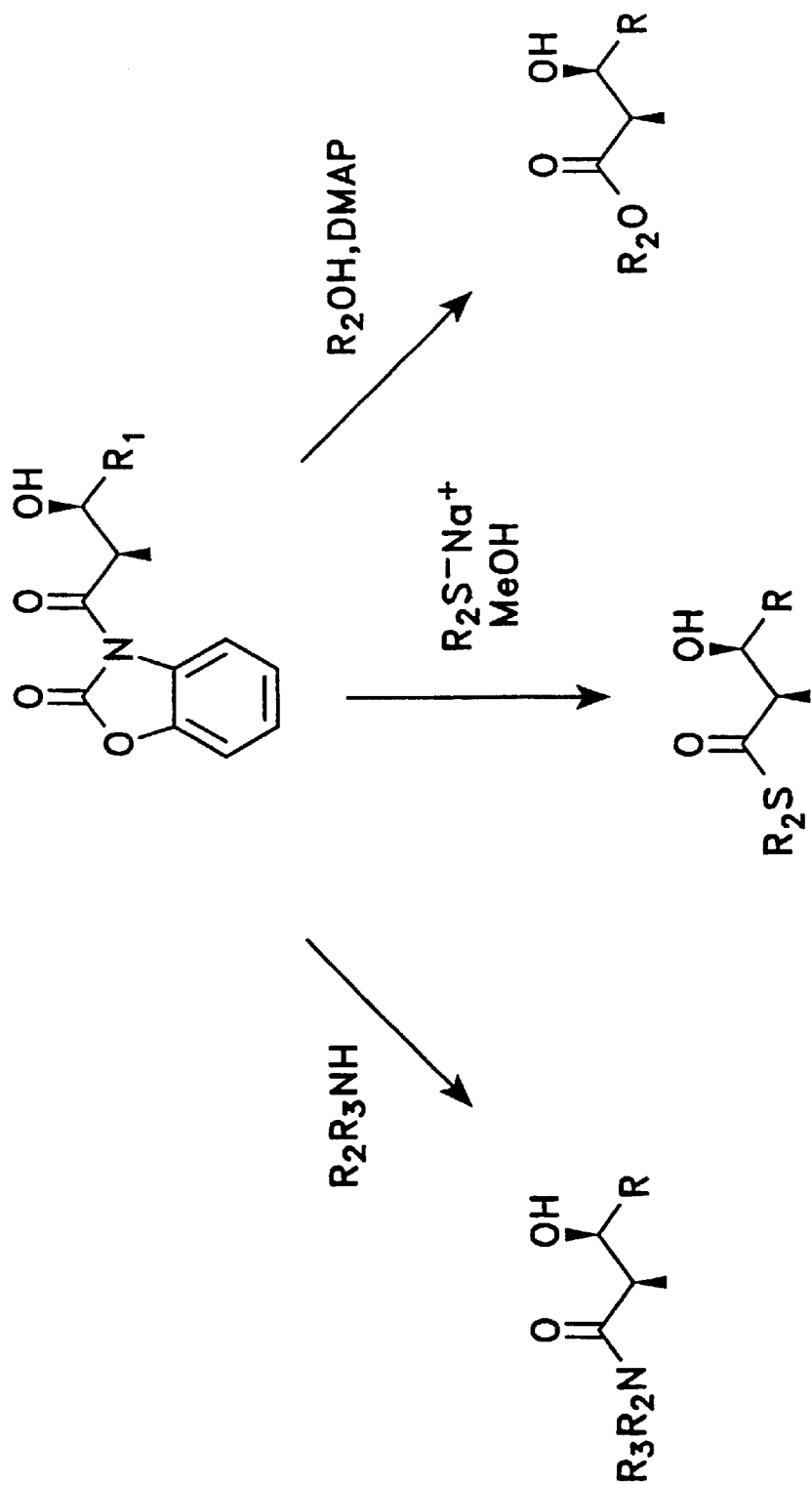
FIG. 3 illustrates methods for the conversion of N-acyl-2-benzoxazolones into various acyl derivatives, including N-acylcysteamine thioesters.

The invention also provides a method for the direct conversion of N-acyl-2-benzoxazolones into N-acylcysteamine thioesters by simple treatment with an alkali metal salt of the mercaptan in an alcohol solvent (FIG. 3). This is efficient and mild due to the more ready displaceability of the benzoxa zolone as compared with an oxazolidinone and the lower basicityof thiolates in protic solvents. Methods for the conversion of the N-acylbenzoxazolones into other functional groups are also illustrated. The alkali metal salt of the mercaptan may be generated through the reaction of a mercaptan with a metal alkoxide, such as sodium methoxide or sodium ethoxide, under inert atmosphere so as to prevent disulfide formation. In a particularly simple embodiment, the required alkali metal salt of the mercaptan is generated in situ through treatment of a alcoholic solution of a simple thioester, e.g., N,S-diacylcysteamine, with one molar equivalent of an alkali metal alkoxide. Addition of the N-acylbenzoxazolone where acyl is an oligoketide then provides the oligoketide thioester. Suitable alcohols are methanol, ethanol, isopropanol, and related solvents. Suitable alkali metal alkoxides are those derived from the aforementioned alcohol solvents, such as lithium methoxide, sodium methoxide, potassium methoxide, and similar salts of the other alcohols. The reaction is typically performed at ambient temperatures. This method has the advantage of avoiding disulfides which are typically present in free mercaptans due to air oxidation. The N,S-diacylcysteamines are readily available through the reaction of cysteamine hydrochloride with an excess of the acyl anhydride in water in the presence of a suitable base. A convenient base is saturated aqueou s sodium bicarbonate, which provides a pH where the thioester product is stable. Unlike N-acylcysteamines, the N,S-diacylcysteamines are typically crystalline, stable materials which can be stored indefinitely.

Figure 4:
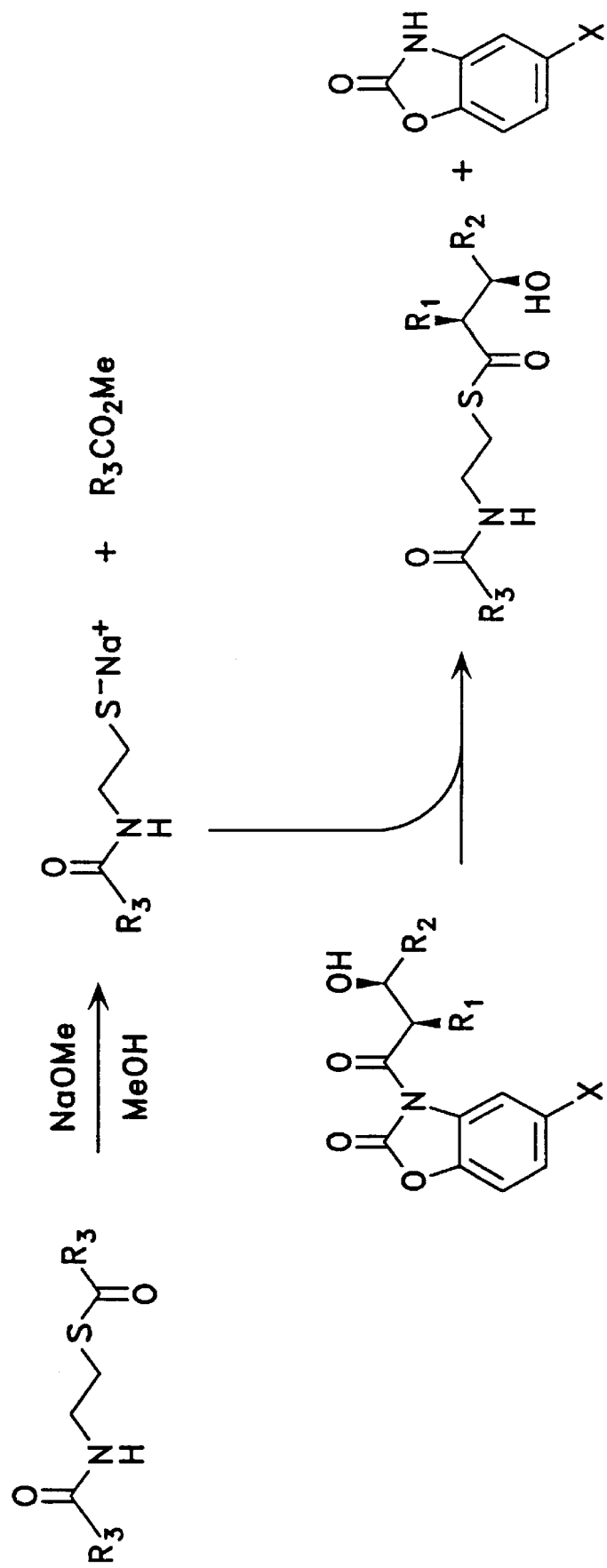
FIG. 4 illustrates the transthioesterification method developed for use with the diketide benzoxazolones.
Figure 5:
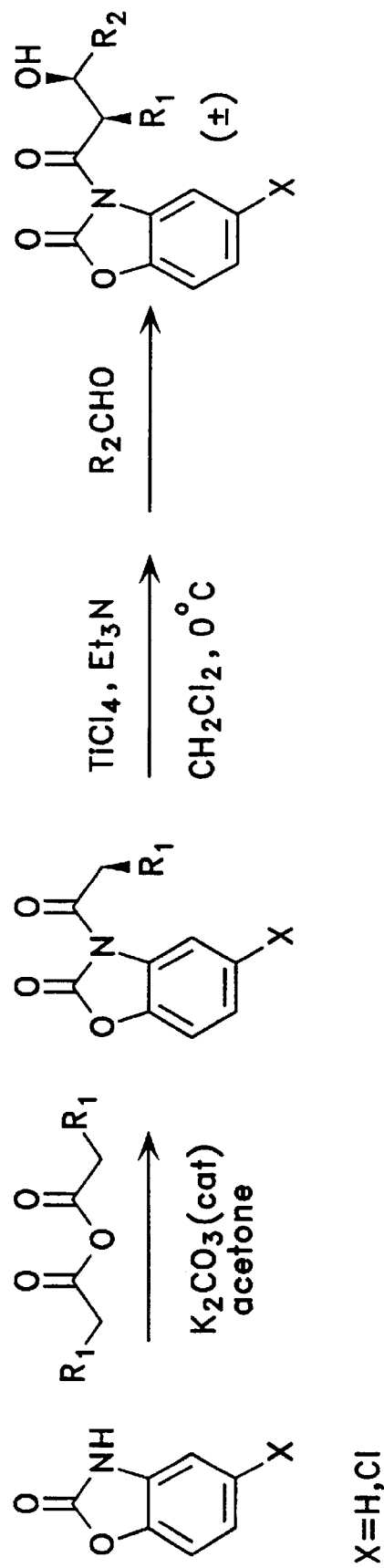
FIG. 5 illustrates the formation of N-acyl-2-benzoxazolone and the aldol condensation between N-acyl-2-benzoxazolones and aldehydes, used to prepare intermediates for the synthesis of racemic diketides.
Figure 6:
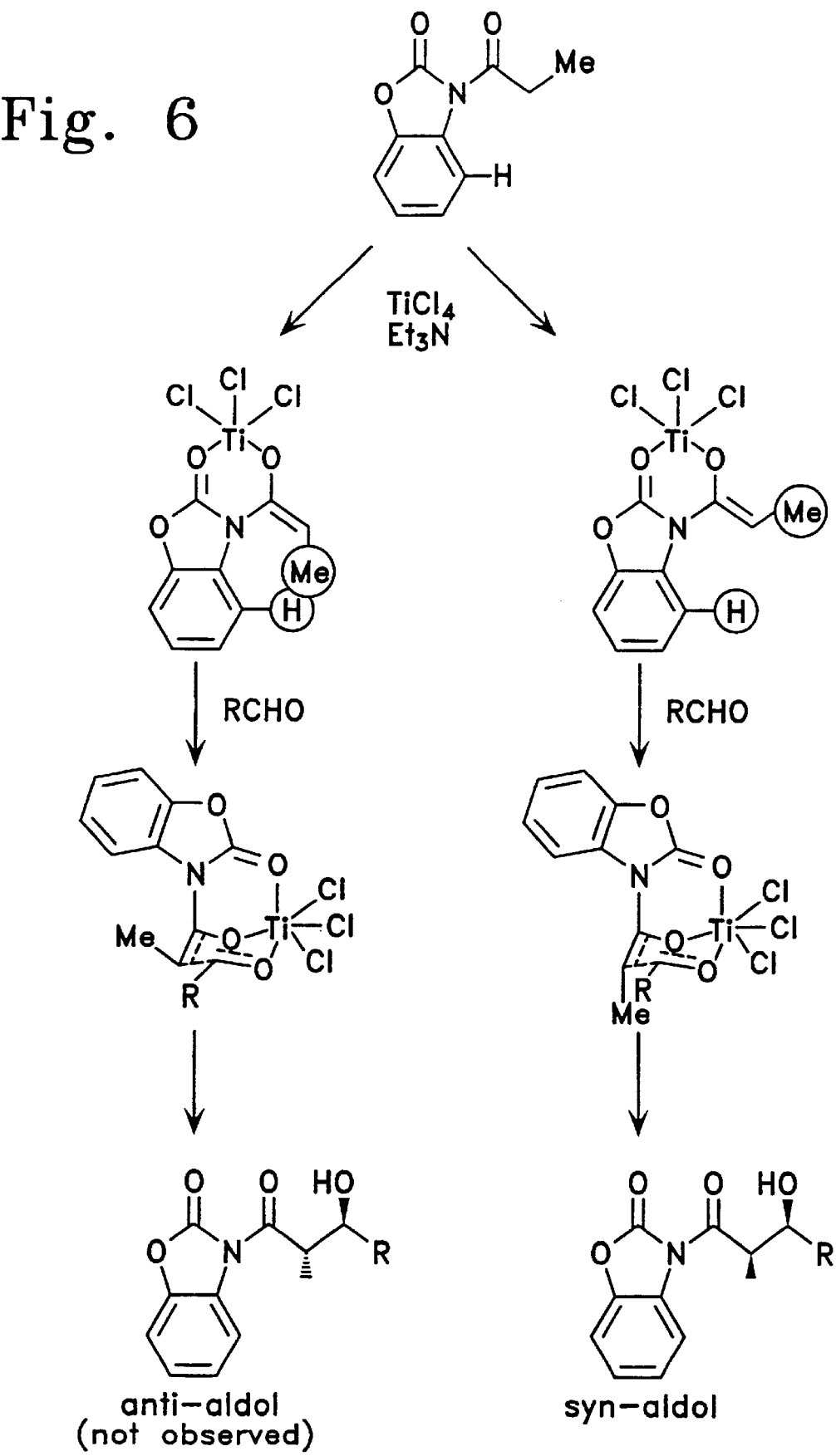
FIG. 6 illustrates the rationale for enforcement of syn-stereochemistry by the benzoxazolone auxiliary.
Figure 7:
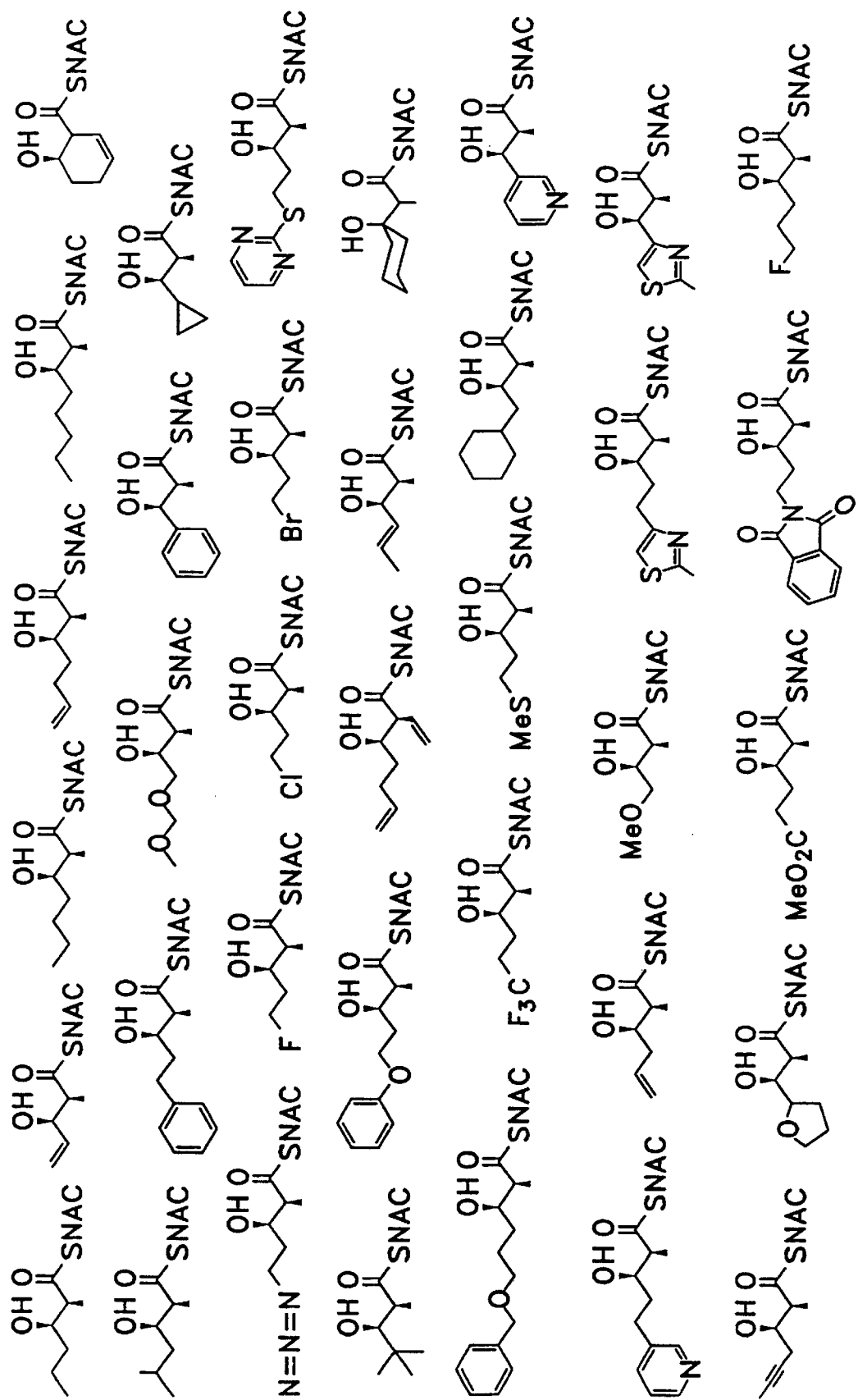
FIG. 7 illustrates typical diketides, shown as their N-acylcysteamine (SNAC) thioesters, prepared according to the invention.
Figure 8:
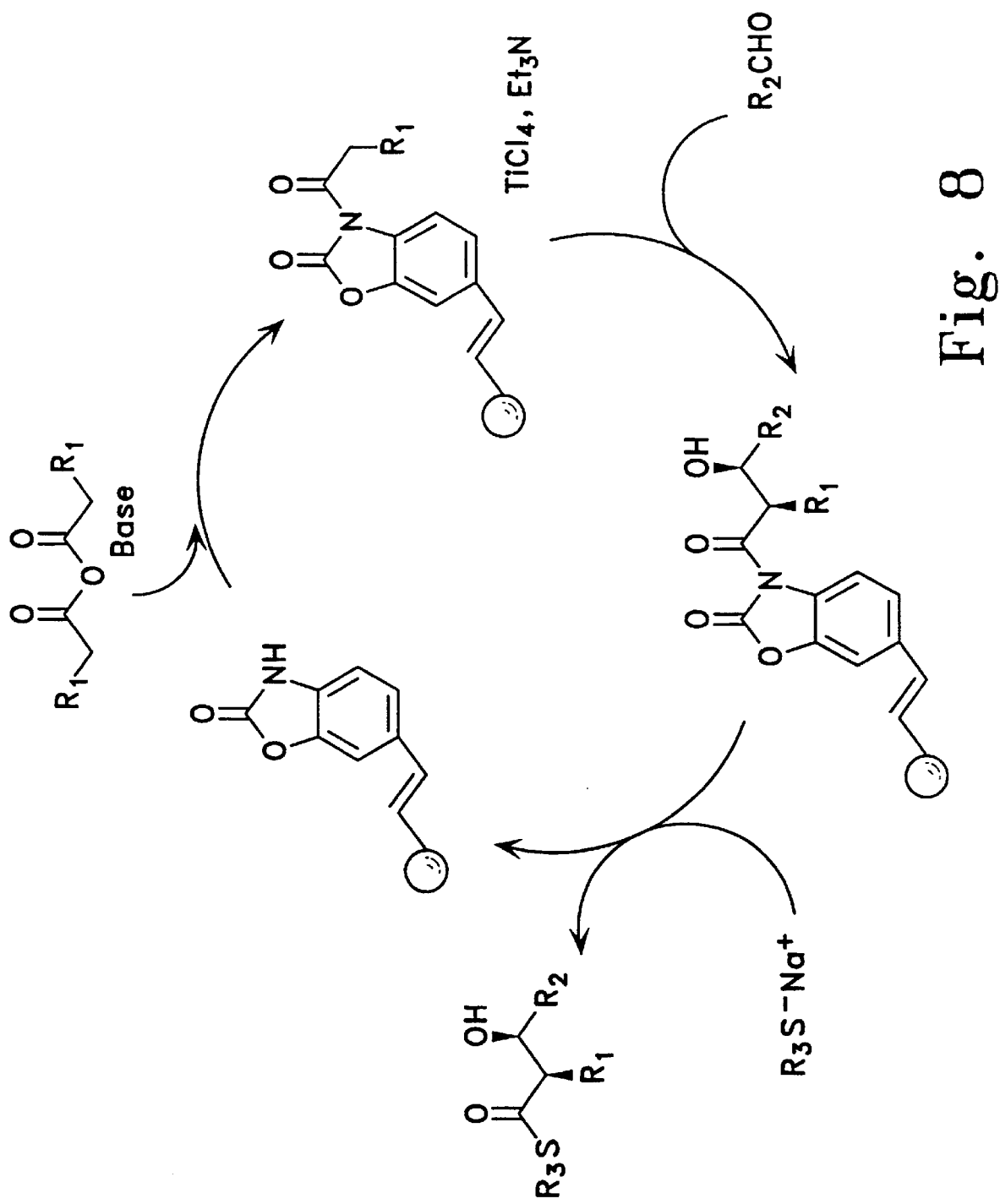
FIG. 8 illustrates synthesis of oligoketide thioesters using solid-phase chemistry.

The invention further provides a method for synthesis of racemic diketides using 2-benzoxazolone as supporting auxiliary (FIG. 4). The titanium tetrachloride-mediated aldol condensation between N-propionyl-2-benzoxazolone and an aldehyde provides high yields of these diketides, with excellent diastereochemical control. "Benzoxazolone derivative" means, generally, the imide of an acyl group with a 2-benzoxazolone. The aromatic moiety in benzoxazolone may be unsubstituted as in benzoxazolone per se or may be substituted, for example as is the case for chlorzoxazone. Alternative substitutions on the benzylidene moiety may also be employed, such as bromo, methyl, and the like. Both 2-benzoxazolone and 5-chloro-2-benzoxazolone (chlorzoxazone) have been shown to be effective auxiliaries, supporting >95% syn aldol condensation for simple aldehydes and ca. 90% syn aldol condensation with sterically-hindered aldehydes such as pivalaldehyde and with chelating aldehydes such as α-alkoxyaldehydes. The titanium aldol condensation has further advantages in that it can be performed at moderate temperatures (0° C.), unlike reactions of lithium enolates which require the use of −78° C., and in that the reagents are extremely inexpensive ($10/mol) as compared with dibutylboron triflate ($750/mol). Further, the oxidative workup using concentrated hydrogen peroxide needed with boron-mediated aldols is not required.

The use of N-propionyl-2-benzoxazolone in the aldol condensation provides diketides of benzoxazolones having a 2-methyl substituent, which, in turn, provides a 12-methyl group in the 6-dEB analog obtained upon conversion of the diketide by the erythromycin PKS. Similarly, the use of N-crotonyl-2-benzoxazolone ultimately provides diketides having a 2-vinyl substituent, which provides a 12-vinyl group in the 6-dEB analog obtained upon conversion of the diketide by the erythromycin PKS. Other N-acyl-2-benzoxazolones can be used to provide other 2-substituted diketides, and thus other 12-substituted 6-dEB and erythromycin analogs.

The invention further provides a method for introducing substituents at the 12-, 14-, and 15-positions of 6-dEB or erythromycin which are not tolerated by the erythromycin PKS and thus cannot be introduced directly by feeding the corresponding oligoketide thioester. This method involves feeding an oligoketide thioester containing a functional group, typically an alkene or a protected alcohol group, which is tolerated by the PKS and which can be converted post-PKS into the desired functionality using chemical, enzymic, or biological conversion. For example, the erythromycin PKS will efficiently convert diketides containing alkene groups either at the 2- or 3-positions (or both) to provide the corresponding 12- or 13-vinyl 6-dEB analogs. The erythromycin PKS will convert 3-hydroxy-2-methyl-4-pentenoate N-acylcysteamine thioesters into 14,15-dehydro-6-dEB, for example, and the post-PKS enzymes of *Saccharopolyspora erythraea* will convert this further into 14,15-dehydroerythromycins. This introduces a unique alkene functionality into the 6-dEB and erythromycin molecules. Methods for conversion of this alkene, e.g., into halides, carbonyls, alcohols, ethers, and amines are well known in the art. The alkene can also be used to add aromatic moieties onto the 6-dEB or erythromycin molecule through the Heck reaction:

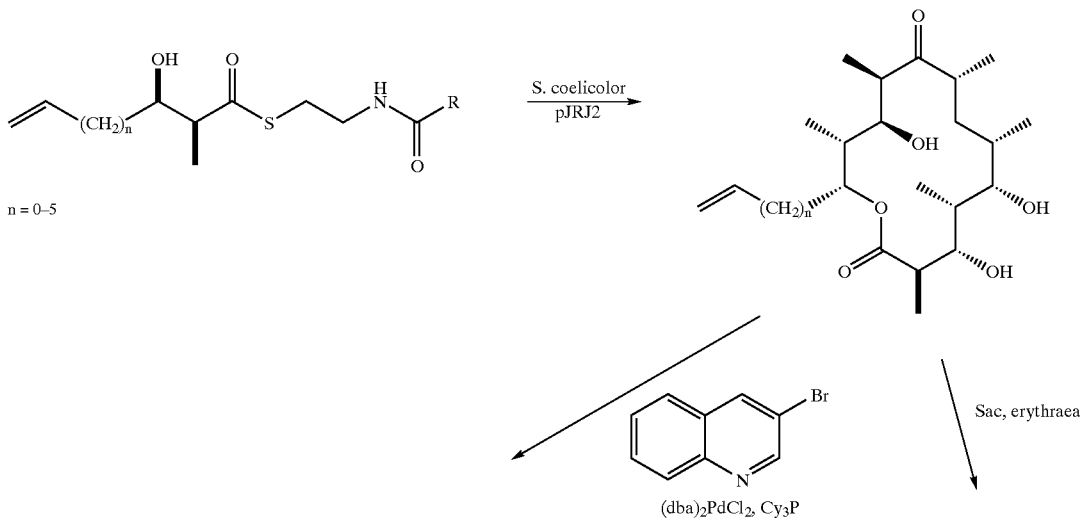

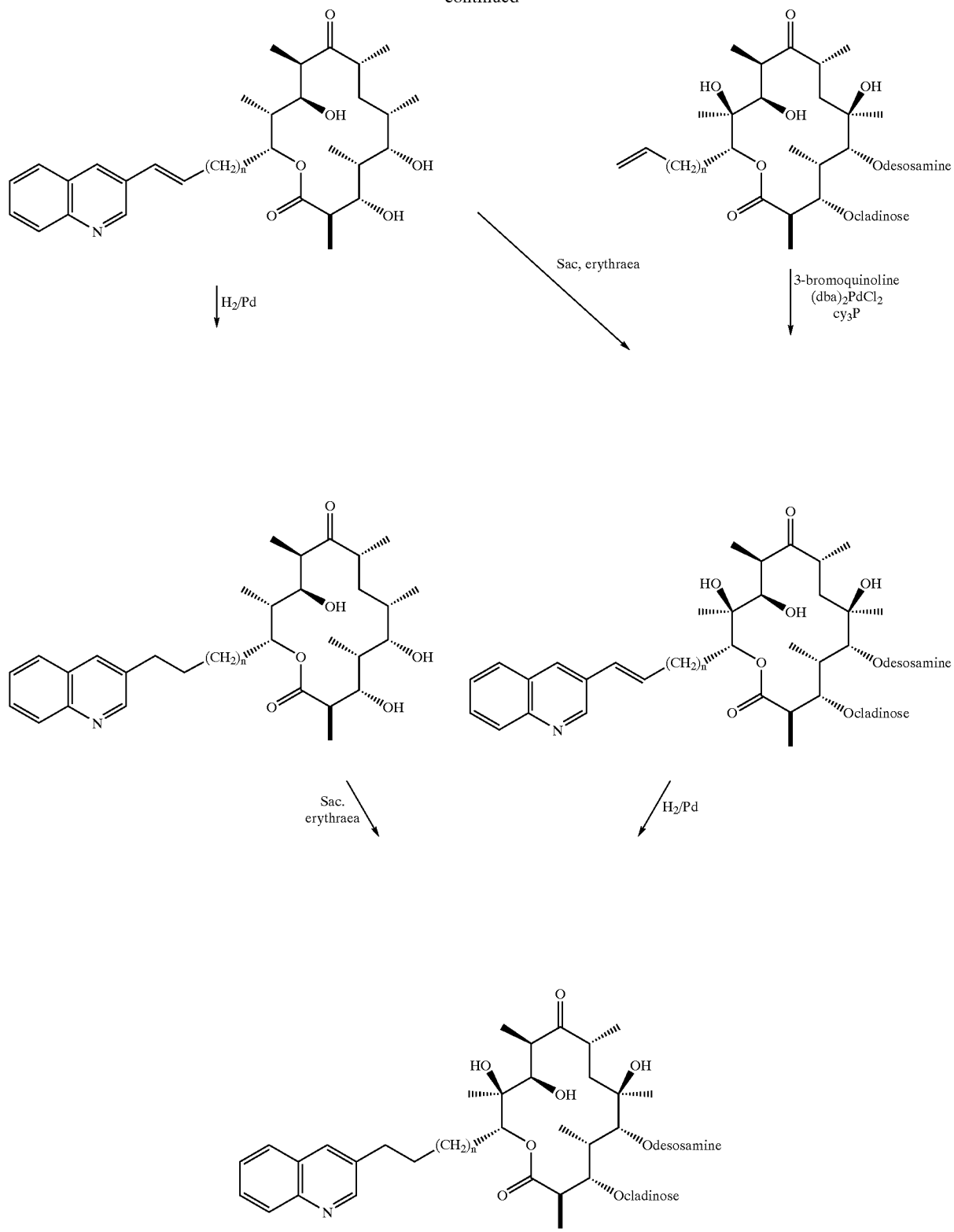

Similarly, the erythromycin PKS will convert 3-hydroxy-2-vinylpentanoate N-acylcysteamine thioesters into 12-desmethyl-12-vinyl-6-dEB. This provides a unique alkene functionality at the 12-position of 6-dEB which can be further manipulated. As an extension of this concept, *Streptomyces coelicolor* CH999 expressing the plasmid pJRJ2 converts 3-hydroxy-2-vinyl-6-heptenoate N-acylcysteamine thioesters into 12,15-divinyl-12-desmethyl-6-dEB at levels of approximately 50 mg/L:

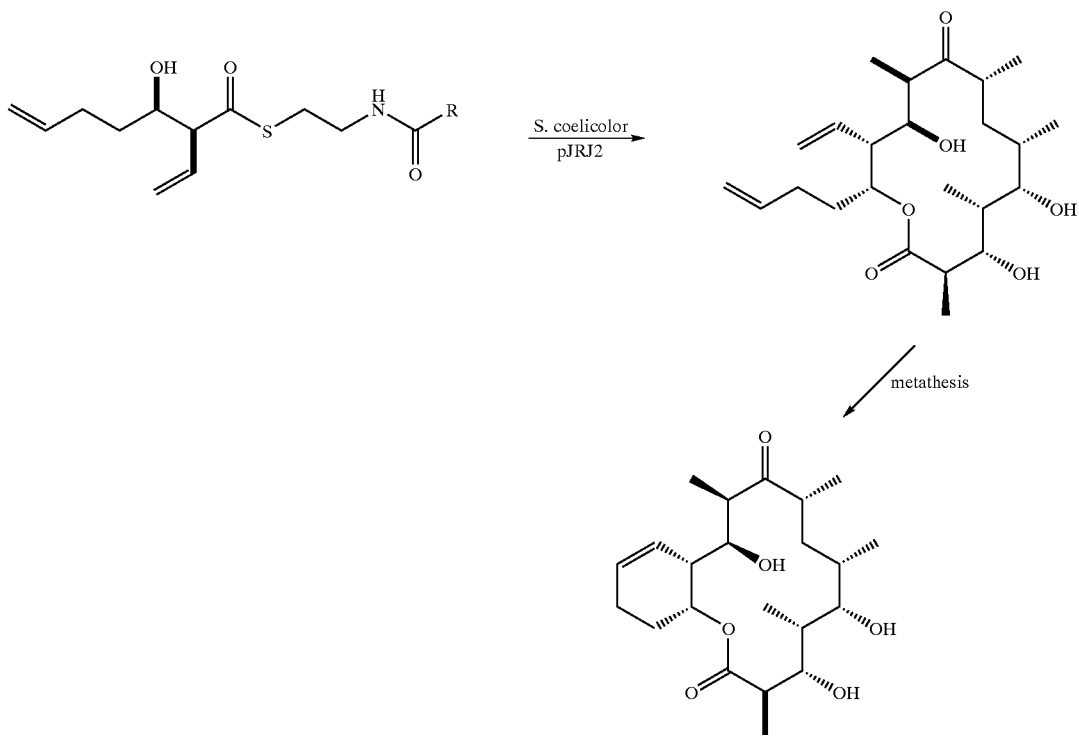

This compound can be subsequently converted into various derivatives, such as the bicyclic analog illustrated through the use of an olefin metathesis catalyst.

Other protected or masked functionalities can be introduced into the 6-dEB and erythromycin molecules in this fashion. For example, alcohols protected as esters or as benzyl ethers would be suitable precursors which would allow for introduction of a new alcohol group in the polyketide. The modification of alcohols into other functional groups is well known in the art.

This methodology can also be used to introduce reactive functionalities directly. As an example, the erythromycin PKS will convert 5-halo-3-hydroxy-2-methylpentanoate N-acylcysteamine thioesters into the corresponding 15-halo-6-dEBs. The halogen can be F, Cl, Br, or I, and supplies a readily-displaceable group for subsequent modification of the 15-position of the 6-dEB or erythromycin.

It can be seen, therefore, that the feeding of synthetic diketide thioester analogs to the erythromycin PKS or an organism expressing the erythromycin PKS is a useful means of producing novel polyketides. The method is particularly useful when the PKS has been modified so as to preclude formation of the natural polyketide, such as by inactivation of the module 1 ketosynthase, or more generally when the supply of natural starter unit has been otherwise eliminated.

It can be seen as well that methods existing in the art for construction of lengthier oligoketides can be adapted for use in these systems. For examnple, triketides are readily available by aldol condensations between aldehydes and β-ketoimides as described in D. A. Evans, et al., *J. Am. Chem. Soc.* (1990) 112:866–868. Methods have been developed for the efficient control of relative stereochemistry in these transformations, as described in D. A. Evans, et al., *Tetrahedron* (1992) 48:2127–2142. The stereoselective reduction of the resulting products using triacetoxyborohydrides has been described in D. A. Evans, et al., *J. Am. Chem. Soc.* (1988) 110:3560–3578, and provides a means of further altering the functionality of the oligoketides by selective introduction of a β-hydroxyl. Such hydroxyls can be further converted into alkenes through acylation and β-elimination, with the proviso that other hydroxyls in the oligoketide must be protected against acylation or at least must be readily deprotected afterwards. The invention provides a particularly simple method for this transformation using phosgene to form a cyclic carbonate, which simultaneously activates the β-hydroxyl for elimination and protects the δ-hydroxyl:

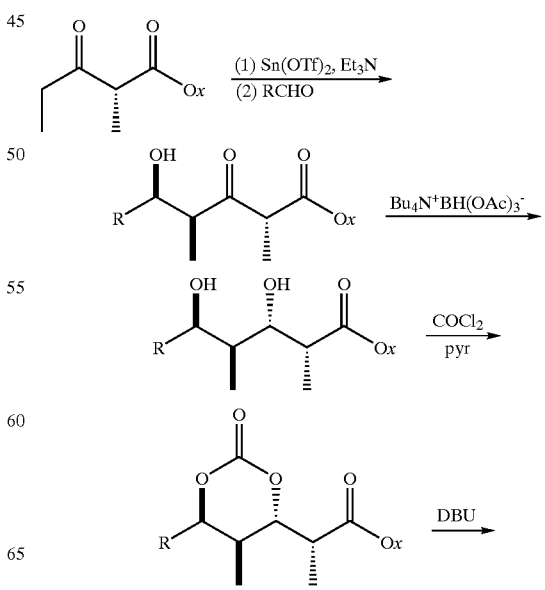

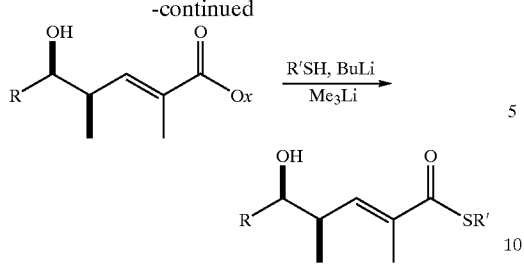

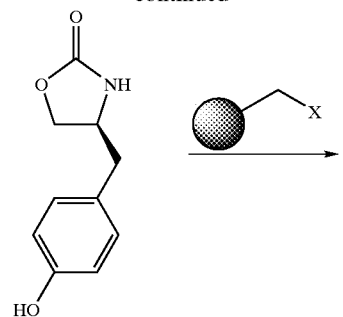

Alternatively, the alkene resulting from elimination can be reduced to the alkane, for example by catalytic hydrogenation, prior to thiolysis. Thus, all four reductive outcomes observed from natural polyketide synthesis can be mimicked in the chemical construction of triketides.

The direct, efficient conversion of oligoketide imides into thioesters opens the possibility of efficient solid-phase synthesis of oligoketide thioesters, as thiolysis can be used to free the oligoketide chain from the solid support as the final step in the synthesis. Methods exist for the linear elaboration of oligoketides wherein the oligoketide chain is grown off an initial auxiliary unit, typically a chiral oxazolidinone, at least up to the triketide level. The number of required steps is minimal and the yields are high. The use of the 4-benzyl-2-oxazolidinone residue maintains the stereochemistry through multiple chain extensions using similar reagents. Because common intermediates are used and the auxiliary stereochemistry controlling compound can readily be linked to solid supports as described in the invention, the method provides a suitable basis for the solid-phase production of combinatorial libraries of triketides and beyond.

Two possible attachment sites to a solid support can be envisioned. By providing functionality on the phenyl group of the 4-benzyloxazolidinone, covalent coupling to a wide variety of supports may conveniently be obtained; means for coupling through this moiety are well known in the art. For example, the corresponding auxiliary derived from tyrosine rather than phenylalanine can be readily prepared. This would provide a phenolic hydroxyl group which could readily be attached to a solid support through, for example, reaction with a chlorobenzyl polystyrene resin to give a diphenylether-linked chiral oxazolidinone.

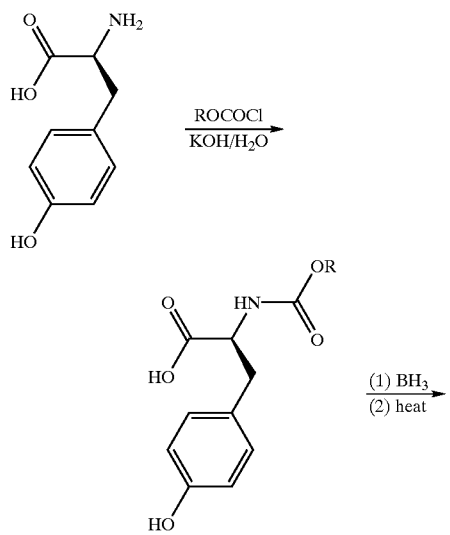

The oligoketide chain can be grown on this support using methods well-established in the art, then cleaved from the solid support, preferably by formation of the thioester as described herein. This offers an advantage over previous methods for solid-phase oligoketide synthesis, e.g., Reggelin, M., et al., *Tetrahedron Letters* (1996) 37:6851–6852, in which the oligoketide chain itself is used as the attachment point, with a corresponding attachment functionality remaining as part of the oligoketide at the end of the synthesis.

Alternatively, the oxazolidinone nrng itself is used as the point of attachment to the support. For example, the solid support of the invention may employ a chiral imidazolidinone, wherein the imidazolidinone replaces the oxazolidinone described above:

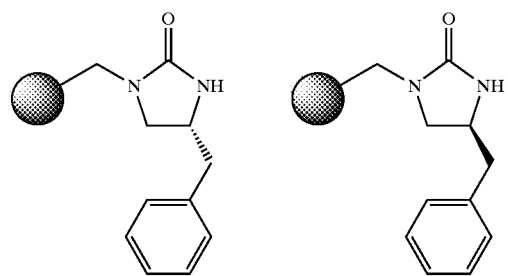

(R)-resin      (S)-resin

The second nitrogen atom of the imidazolidinone is used as the attachment point to the solid support, leaving the nitrogen adjacent to the chiral center (equivalent to the nitrogen in an oxazolidinone) open for acylation with an acyl chloride. The use of untethered chiral imidazolidinones as synthetic auxiliaries has been described by S. E. Drewes, el al., *Chem. Ber.* (1993) 126:2663, and an especially facile method for their acylation has been described by W. M. Clark & C. Bender, *J. Org. Chem.* (1998) 63:6732.

The tethered chiral imidazolidinones can be readily prepared from optically pure amino acids by standard procedures; e.g., by conversion of a chiral amino acid such as phenylalanine into the carbamate by reaction with a suitable chloroformate or chloroformnate equivalent, followed by conversion to the aminoaldehyde (Rittel, K. E., et al., *J Org Chem* (1988) 47:3016; *Organic Syntheses*, vol. 67:69–75) and subsequent reductive amination to add a suitable functionalized linker.

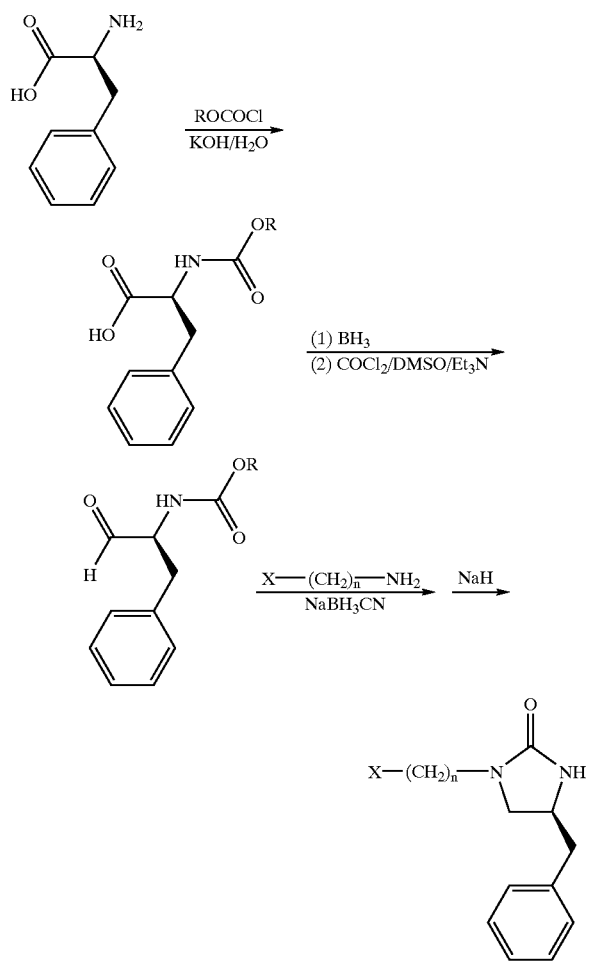

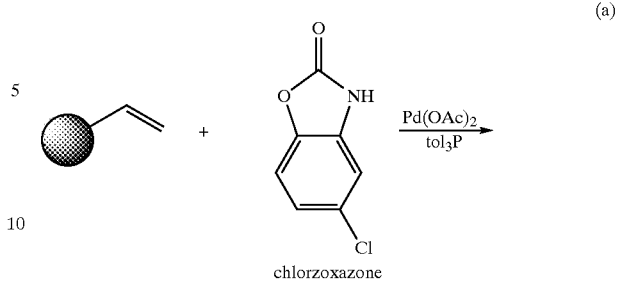

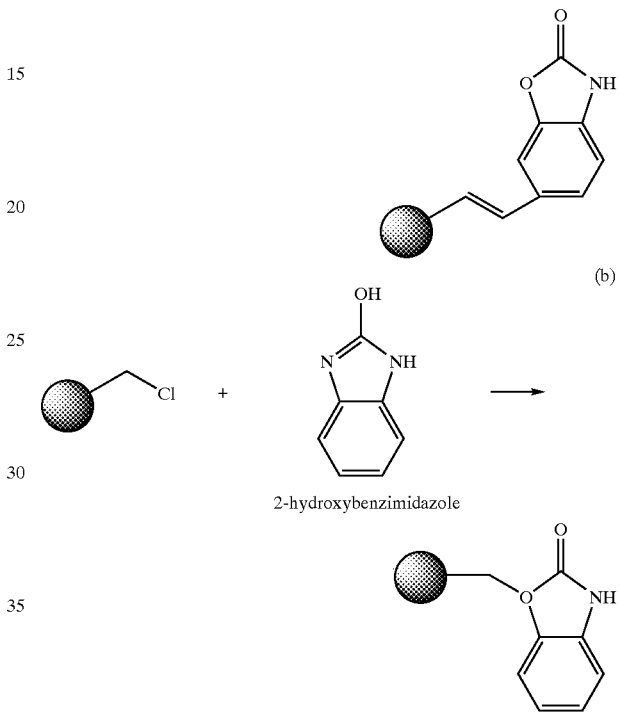

The functional group, shown as "X" is, for example, an amine, a carboxylate or an ester, thiol or halide which is used to attach the auxiliary to a solid support. The resulting amino carbamate is cyclized to the imidazolidinone by treatment with a suitable base or with heat.

Racemic diketides can be synthesized on solid supports using a similar technique. In this case, the 2-benzoxazolone auxiliary can be attached to the support by either of two methods. Halogenated benzoxazolones, such as chlorzoxazone (5-chloro-2-benzoxazolone), are readily available and provide a simple means of attachment through the aromatic halide. For example, chlorzoxazone can be coupled with an alkene-containing support using palladium catalysis (the Heck reaction). Alternately, 2-benzimidazolone (2-hydroxybenzimidazole) can be coupled to a support through one of the imidazolone nitrogens, leaving the second free for acylation as described above.

The methods described above for elaboration of triketides are ideally suited to solid-phase synthesis, as the directing auxiliary group (oxazolidinone or benzoxazolone) remain attached to the growing oligoketide chain. The attached auxiliary then serves as a leaving group during thioester formation, yielding an oligoketide thioester with no residue remaining from the solid support.

Incorporation into Polyketides

As used herein, "polyketide" refers to the immediate product of a polyketide synthase enzyme system. It is generally a lactone of 13–15C. An example of a polyketide would be 6-dEB, the immediate product of the erythromycin PKS. "Tailored polyketides" refers to the products of subsequent derivatization of the resultant polyketide which occurs through enzymatic treatment by enzymes endogenous to organisms which synthesize polyketide antibiotics. Such tailoring enzymes may add hydroxyl groups, remove hydroxyl or oxo groups, add sugars, modify sugars that have been coupled to the polyketide, and the like. "Derivatized polyketides" refers to polyketides or tailored polyketides which have been modified chemically in ways generally unavailable from straightforward enzymatic treatment. The diketides and triketides prepared by the methods of the invention, because they contain functional groups which can further be reacted result in polyketides and tailored polyketides that can be derivatized using synthetic chemical reactions. Methods for further converting polyketides (or tailored polyketides) are found, for example, in PCT publications WO 99/35156 and WO 99/35157, incorporated herein by reference. Such methods are also described in U.S. Ser. Nos., respectively, 60/172,154 and 60/172,159, both filed Dec. 17, 1999; 60/173,805 filed Dec. 30, 1999; and 60/173,804 filed Dec. 30, 1999, and each incorporated herein by reference.

The thioesters of the diketides and triketides of the invention can be incorporated into polyketides by the PKS system, most advantageously when competition from the native starter unit is eliminated by, for example, the inactivation of the ketosynthase domain in module 1 as described in PCT application PCT/US96/11317 incorporated herein by reference. Polyketide synthases thus modified are also described in U.S. Ser. No. 08/896,323 filed Jul. 17, 1997 and incorporated herein by reference. As described in these applications, the polyketide synthase system can be employed in a cell-free context, or can be utilized in vivo either in its native host or in a recombinant host cell. For example, the organism which natively produces erythromycin, *Saccharopolyspora erythreae* may be used, or, as set forth in U.S. Pat. No. 5,672,491, the entire erythromycin gene cluster can be inserted into a suitable host such as *Streptomyces coelicolor* or *S. lividans*, preferably a *S. coelicolor* or *S. lividans* which has been modified to delete its endogenous actinorhodin polyketide synthesis mechanism. A typical host would be *S. coelicolor* CH999/pJRJ2, which expresses a mutant 6-deoxyerythronolide B synthase having an inactivated module 1 ketosynthase (J. Jacobsen, et al., 1997 *Science* 277:367–369). The diketides or triketides are thus incorporated into the resulting polyketide. In the case of the diketides and triketides provided by this invention, the resulting erythronolide will be correspondingly modified at positions 10–15. For example, feeding a growing culture of *S. coelicolor* CH999/pJRJ2 with (2S,3R)-5-fluoro-3-hydroxy-2-methylpentanoate N-acetylcysteamine thioester results in production of 15-fluoro-6-deoxyerythronolide B, while feeding with (2S,3R)-3-hydroxy-2-methylhexanoate N-acetylcysteamine thioester results in production of 15-methyl-6-deoxyerythronolide B. Feeding *S. coelicolor* CH999/pJRJ2 with (2S,3R)-3-hydroxy-2-vinylpentanoate N-acetylcysteamine thioester results in production of 12-desmethyl-12-vinyl-6-deoxyerythronolide B.

Further, the diketide or triketide intermediates can be provided to PKS enzymes other than the 6-dEB synthase of *Saccharopolyspora erythraea*. Other PKS enzymes include the 6-dEB synthase of *Micromonospora megalomicea* and its KS1° derivative described in U.S. Ser. No. 60/158,305, filed Oct. 8, 1999; the oleandolide PKS and its KS1° derivative described in PCT application No. US99/24478, filed Oct. 22, 1999; and the narbonolide PKS and its KS1° derivative described in PCT publication No. WO 99/61599, published Dec. 2, 1999, all incorporated by reference.

The diketides and triketides can be provided to a host cell that expresses a PKS but not post PKS modification enzymes (such as hydroxylases and glycosyltransferases) or can be provided to a host cell that expresses both types of enzymes.

Recombinant host cells containing cloned PKS expression vectors can be constructed to express all of the biosynthetic genes for a modified polyketide or only a subset of the same. If only the genes for the PKS are expressed in a host cell that otherwise does not produce polyketide modifying enzymes that can act on the polyketide produced, then the host cell produces unmodified polyketides. Such unmodified polyketides can be hydroxylated and glycosylated, for example, by adding them to the fermentation of a strain such as, for example, *Streptomyces antibioticus* or *Saccharopolyspora erythraea*, that contains the requisite modification enzymes.

If desired, further modifications at positions 14 and 15 are achievable once the resulting polyketide is isolated by employing an appropriate benzyloxy-, alkene-, or halo-substituted diketide thioester. As set forth above, these groups can be converted to other functionalities using methods well known in the art.

The resulting polyketides can further be modified by chemical means or by feeding to a native antibiotic producing host for glycosylation or further modification. For example, a resulting 6-deoxyerythronolide can be fed to *Sac. erythraea* for hydroxylation at the 6- and/or 12-positions and sugar attachment at the 3- and/or 5-positions. This is particularly useful when the organism used contains a defective PKS gene, resulting either from random mutagenesis or from designed deletion. The strain *Sac. erythraea* K39–14 expresses a defective 6-deoxyerythronolide B synthase, and so is incapable of producing erythromycins under normal fermentation conditions. Feeding a growing culture of *Sac. erythraea* K39–14 with 15-fluoro-6-deoxyerythonolide B results in production of 15-fluoroerythromycins. Feeding this strain with 15-methyl-6-deoxyerythronolide B results in formation of 15-methylerythromycins. Both 15-fluoroerythromycin A and 15-methylerythromycin A have been found to have strong antibacterial activity.

In lieu of, or in addition to chemical synthesis steps, the initially produced polyketides can be "tailored." There is a wide variety of diverse organisms that can modify polyketides and/or their derivatives to provide compounds with, or that can be readily modified to have, useful activities. As stated above, *Saccharopolyspora erythraea* can convert 6-dEB to a variety of useful compounds. The erythronolide 6-dEB is converted by the eryF gene product to erythronolide B, which is, in turn, glycosylated by the eryB gene product to obtain 3-O-mycarosylerythronolide B, which contains L-mycarose at C-3. The enzyme eryC gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromycin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product. The unmodified polyketide compounds provided by the present invention can be provided to cultures of *S. erythraea* and converted to the corresponding derivatives of erythromycins A, B, C, and D in accordance with the invention. To ensure that only the desired compound is produced, one can use an *S. erythraea* eryA mutant that is unable to produce 6-dEB but can still carry out the desired conversions (Weber, et al., 1985, *J. Bacteriol.* 164(1):425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

There are other useful organisms that can be employed to hydroxylate and/or glycosylate the compounds of the invention. The organisms can be mutants unable to produce the polyketide normally produced in that organism, the fermentation can be carried out on plates or in large fermentors, and the compounds produced can be chemically altered after fermentation. Thus, *Streptomyces venezuelae*, which produces picromycin, contains enzymes that can transfer a desosaminyl group to the C-5 hydroxyl and a hydroxyl group to the C-12 position. In addition, *S. venezuelae* contains a glucosylation acticity that glucosylates the 2'-hydroxyl group of the desosamine sugar. This latter modification reduces antibiotic activity, but the glucosyl residue is removed by enzymatic action prior to release of the polyketide from the cell. Another organism, *S. narbonensis*, contains the same modification enzymes as *S. venezuelae*, except the C-12 hydroxylase. Thus, the present invention includes the compounds produced by hydroxylation and glycosylation of the initially formed polyketides of the invention by action of the enzymes endogenous to *S. narbonensis* and *S. venezuelae*.

Other organisms suitable for making compounds of the invention include *Micromonospora megalomicea, Streptomyces antibioticus, S. fradiae,* and *S. thermotolerans. S. antibioticus* produces oleandomycin and contains enzymes that hydroxylate the C-6 and C-12 positions, glycosylate the C-3 hydroxyl with oleandrose and the C-5 hydroxyl with desosamine, and form an epoxide at C-8–C-8a. *S. fradiae* contains enzymes that glycosylate the C-5 hydroxyl with mycaminose and then the 4'-hydroxyl of mycaminose with mycarose, forming a disaccharide. *S. thermotolerans* contains the same activities as *S. fradiae*, as well as acylation activities. Thus, the present invention provides the compounds produced by hydroxylation and glycosylation of the macrolide aglycones of the invention by action of the enzymes endogenous to *S. antibioticus, S. fradiae* and *S. thermotolerans*. The modified polyketides of the invention can also be produced in recombinant host cells that have been transformed with genes that encode polyketide modification enzymes from another organism.

The present invention also provides methods and genetic constructs for producing the glycosylated and/or hydroxylated compounds of the invention directly in the host cell of interest. Thus, the polyketides of the invention can be produced directly by feeding in *Saccharopolyspora erythraea, Streptomyces antibioticus, Microinonospora megalomicea, S. fradiae,* and *S. thermotolerans*. A number of erythromycin high-producing strains of *Saccharopolyspora erythraea* have been developed, and such strains can also be used to feed the diketide compounds of the invention to produce modified polyketides.

Modification can also be effected by chemical means, such as glycosylation through cell-free preparations of appropriate glycosylases or through chemical derivatization. Thus, a multiplicity of polyketides and corresponding antibiotics may be obtained using the methods and compounds of the invention.

In a specific embodiment of the invention, the diketide thioester prepared from 4-pentenal is used to produce 15-ethenylerythromycins, which can be chemically converted into 15-(2-arylethyl)erythromycin analogs such as 15-(2-(3-quinolyl)ethyl)erythromycin A and related compounds:

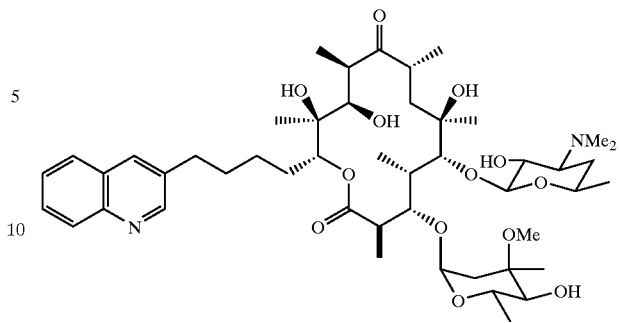

These analogs are expected to provide an aromatic moiety suitably positioned to interact with additional binding sites on the bacterial ribosome, and thus exhibit enhanced antibacterial activity. Particularly preferred analogs are the 6-O-methyl-3-descladinosyl-3-oxo analog and the corresponding 11,12-cyclic carbamate (X=H,F):

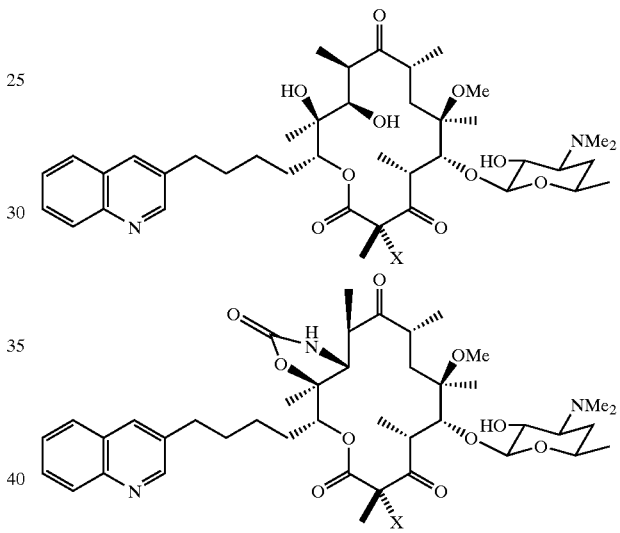

Given the high structural similarity between the modular polyketide synthases examined to date, it should be clear that the invention will provide methods for production of novel polyketides using many different enzymes other than the erythromycin polyketide synthase. For example, the genes encoding the polyketide synthases for rapamycin, FK-506, soraphen, epothilone, rifamycin, picromycin, tylosin, spiramicin, niddamycin, and avermectin have been examined and found to show high homologies.

The following examples are thus intended to illustrate, not to limit, the invention.

Preparation A

N,S-Diacyl Cysteamines

A. N,S-Diacetylcysteamine:

Cysteamine hydrochloride (50.0 g) is added to a 1-L 3-neck round bottom flask fitted with a magnetic stir bar, 2 addition funnels, and a pH electrode. Water (300 ml) is added and the stirred solution is cooled on ice. The pH is adjusted to 8.0 by addition of 8 N KOH. Acetic anhydride (125 ml) is placed in one addition funnel, and 8N KOH (350 ml) is placed in the other addition funnel. The acetic anhydride is added dropwise to the cysteamine solution, with 8 N KOH being added so as to keep the reaction pH at 8 +/−1. After addition of acetic anhydride is complete, the pH was adjusted to 7.0 using 1 N HCl and the mixture is allowed to stir for 75 min on ice. Solid NaCl is added to saturation, and the solution is extracted 4 times using 400 ml portions of $CH_2Cl_2$. The organic extracts are combined, dried over $MgSO_4$, filtered, and concentrated under reduced pressure to yield 68.9 g (97% yield) of a pale yellow oil, which crystallizes upon standing at 4° C. $^1$H-NMR ($CDCl_3$, 400 MHz): δ 6.43 (br s, 1H), 3.42 (q, 2H, J=7), 3.03 (t, 2H, J=7), 2.36 (s, 3H), 1.98 (s, 3H). $^{13}$C-NMR ($CDCl_3$, 100 MHz): δ 196.09, 170.45, 39.42, 30.56, 28.71, 23.06.

B. N,S-Dipropionylcysteamine:

A solution of cysteamine hydrochloride (100 g) in 750 mL of water in a 2-L round bottom flask fitted with a 250 ml addition funnel and a magnetic stirrer was treated with potassium hydroxide (49.4 g). Sodium bicarbonate (222 g) was added after complete dissolution of the KOH. The addition funnel was charged with propionic anhydride (237 mL), which was added to the reaction over a period of 1 hour. Upon completion of addition, the reaction was stirred vigorously for an additional 1 hour. Solid sodium chloride was added to saturation, and the solution was extracted 4 times with 500 ml portions of $CH_2Cl_2$. The organic extracts were combined, dried over $MgSO_4$, filtered, and concentrated on rotary evaporator to give 155.2 g (93% yield) of a pale yellow oil, which crystallizes upon standing at 4° C.; mp 48–49° C. $^1$H-NMR ($CDCl_3$, 400 MHz): δ 5.8 (br s, 1H); 3.44 (q, 2H, J=6); 3.03 (t, 2H, J=6); 2.59 (q, 2H, J=7); 2.19 (q, 2H, J=7); 1.18 (t, 3H, J=7); 1.14 (t, 3H, J=7). $^{13}$C-NMR ($CDCl_3$, 100 MHz): δ 200.64, 174.05, 39.45, 37.38, 29.52, 28.36, 9.74, 9.60.

C. N,S-dibutyrylcysteamine:

Butyryl chloride (10.4 mL) was added dropwise to a solution of cysteamine (3.86 g) and triethylamine (14 mL) in 150 mL of dichloromethane at 0° C. After addition, the mixture is warmed to ambient temperature and stirred for an additional hour. The mixture is poured into water, and the organic phase is collected. The organics are washed sequentially with water, 1N HCl, saturated $NaHCO_3$, and brine, then dried over $MgSO_4$, filtered, and evaporated to yield a colorless oil. Crystallization yields a waxy solid. $^1$H-NMR ($CDCl_3$): δ 6.0 (br s, 1H), 3.44 (q, 2H, J=6); 3.03 (t, 2H, J=6); 2.55 (t, 2H, J=7); 2.14 (t, 2H, J=7); 1.67 (m, 4H); 0.98 (t, 3H, J=7); 0.94 (t, 3H, J=7). $^{13}$C-NMR ($CDCl_3$): δ 200.00, 173.15, 45.86, 39.50, 38.52, 28.39, 19.09, 19.01, 13.66, 13.39.

D. N,S-dipentanoylcysteamine, N,S-dihexanoylcysteamine, N,S-diheptanoylcysteamine, and N,S-dioctanoylcysteamine:

These were prepared as in paragraph A by reaction of cysteamine hydrochloride with the appropriate anhydride or acid chloride.

Preparation B

Preparation of N-Acylcysteamines

A. N-Acetylcysteamine:

N,S-diacetylcysteamine (42.64 g) is placed in a 2-L round bottom flask fitted with a magnetic stirrer, and dissolved in 1400 ml of water. The flask is purged with $N_2$, and the mixture is chilled on an ice bath. Potassium hydroxide (49.42 g) is added, and the mixture is stirred for 2 h on ice under inert atmosphere. The pH is adjusted to 7 using 6 N HCl, and solid NaCl is added to saturation. The mixture is extracted 7 times with 500 ml portions of $CH_2Cl_2$. The organic extracts are combined, dried over $MgSO_4$, filtered, and concentrated under reduced pressure to yield 30.2 g (96% yield) of product. This material is distilled immediately prior to use, bp 138–140° C./7 mmHg.

B. N-Propionylcysteamine:

A solution of N,S-dipropionylcysteamine (18.9 g) in methanol (100 mL) is placed under a nitrogen atmosphere with stirring. A solution of sodium methoxide (25 wt %) in methanol (ca. 22 mL) is added slowly until analysis by thin-layer chromatography (1:1 ethyl acetate/hexane) reveals complete disappearance of starting material. Oxalic acid dihydrate (6.3 g) is added, then the mixture is vacuum filtered through a pad of Celite and evaporated to give a colorless oil. Purification by distillation gives the product.

C. Additional N-acylcysteamines:

Using the procedure of paragraph A, the corresponding N-butyrylcysteamine, N-pentanoylcysteamine, hexanoylcysteamine, N-heptanoylcysteamine, and N-octanoylcysteamine were prepared.

EXAMPLE 1

Preparation of (2S,3R)-2-Methyl-3-hydroxyhexanoate N-Acetylcysteamine Thioester

A. (4S)-N-[(2S,3R)-2-Methyl-3-hydroxyhexanoyl]-4-benzyl-2-oxazolidinone

A dry, 2 L three-necked round bottomed flask equipped with a 500 ml addition funnel, a low-temperature thermometer, and a stir bar was charged with 19.84 g of N-propionyl-oxazolidinone, capped with septa and flushed with nitrogen. Anhydrous dichloromethane (100 ml) was added by cannula and the resulting solution was cooled to −65° C. in a bath of dry ice/isopropanol. The addition funnel was charged by cannula with 100 ml of dibutylboron trinflate (1.0 M in dichloromethane), which was added in a slow stream to the reaction. Triethylamine (15.6 ml) was added dropwise by syringe, keeping the reaction temperature below −10° C. The reaction was then transferred to an ice bath and allowed to stir at 0° C. for 30 minutes. After that period, the reaction was placed back into the dry ice/isopropanol bath and allowed to cool to −65° C. Butyraldehyde (8.6 ml) was added rapidly by syringe, and the reaction was allowed to stir for 30 min.

The reaction was transferred to an ice bath and the addition funnel was charged with 100 ml of a 1 M aqueous phosphate solution, pH 7.0 (the phosphate solution is comprised of equal molar amounts of mono- and dibasic potassium phosphate). The phosphate solution was added as quickly as possible while keeping the reaction temperature below 10° C. The addition funnel was then charged with 300 ml of methanol which was added as quickly as possible while keeping the reaction temperature below 10° C. Finally, the addition funnel was charged with 300 ml of 2:1 methanol-30% hydrogen peroxide. This was added dropwise to ensure that the temperature was kept below 10° C. The reaction was stirred for one hour after completion of addition. The solvent was then removed on a rotary evaporator until a slurry remained. The slurry was extracted 4 times with 500 ml portions of ethyl ether. The combined organic extracts were washed with 250 ml each of saturated aqueous sodium bicarbonate and brine. The extract was then dried with $MgSO_4$, filtered, and concentrated to give a slightly yellow oil. The material was then chromatographed on $SiO_2$ using 2:1 hexanes:ethyl acetate (product Rf=0.4) resulting in 22.0 g (85% yield) of title compound as a colorless oil. APCI-MS: m/z 306 (MH+). $^1$H-NMR (360 MHz, $CDCl_3$): δ 7.2–7.4 (5H, m, phenyl); 4.71 (1H, m, H4); 4.17–4.25 (2H, m, H5); 3.96 (1H, m, H3'); 3.77 (1H, dq, J=2.5,7 Hz, H2'); 3.26 (1H, dd, J=4,13 Hz, benzylic); 2.79 (1H, dd, J=9,13 Hz, benzylic); 1.5–1.6 (2H, m, H4'); 1.3–1.5 (2H, m, H5'); 1.27 (3H, d, J=7 Hz, 2'-Me); 0.94 (3H, t, J=7 Hz, H6').

B. (2S,3R)-2-Methyl-3-hydroxyhexanoate N-Acetylcysteamine Thioester

N-acetylcysteamine was distilled at 130° C./7 mmHg to give a colorless liquid at room temperature. A dry, 1 L three-necked round bottomed flask equipped with a 500 ml addition funnel and a stir bar was capped with septa and flushed with nitrogen. The flask was then charged with 10.7 ml of N-acetylcysteamine by syringe and with 400 ml of anhydrous THF by cannula. The mixture was cooled with a MeOH/ice bath. Butyllithium (64 ml of 1.6 M in hexanes) was added dropwise by syringe, resulting in formation of a white precipitate. After stirring for 30 min, trinethylaluminum (51 ml of 2.0 M in hexanes) was added dropwise by syringe. The reaction became clear after addition of trimethylaluminum and was allowed to stir an additional 30 min. During this period, 20.5 g (0.068 mol) of (4S)-N-[(2S,3R)-2-methyl-3-hydroxylhexanoyl]4-benzyl-2was put under a blanket of nitrogen and dissolved in 100 ml of anhydrous THF; this solution was then transferred in a slow stream by cannula into the reaction. The resulting reaction mixture turned a yellow-green color and was allowed to stir for 1 hr. The reaction was judged complete when the starting material could no longer be seen by thin-layer chromatographic analysis (ca. 1 hr).

The reaction was treated with enough saturated, oxalic acid to give a neutral reaction with pH paper (approximately 90 ml). The solvents were then removed on a rotary evaporator to give a white slurry. The slurry was extracted six times with 250 ml portions of ethyl ether. The organic extracts were combined and washed with brine, dried with $MgSO_4$, filtered, and concentrated to give a slightly yellow oil. The thioester product was purified by flash chromatography on $SiO_2$ using 1:1 hexanes:EtOAc until the elution of 4-benzyl-2-oxazolidinone. At that point, the solvent system was switched to 100% EtOAc to give pure fractions of diketide thioester. The product fractions were combined and concentrated to give 14.9 g (89% yield) of title compound. APCI-MS: m/z 248 (MH+). $^1$H-NMR (360 MHz, $CDCl_3$): δ 5.8 (br s, 1H); 3.94 (dt, 1H), 3.46 (m, 2H), 3.03 (dt, 2H), 2.71 (dq, 1H), 1.97 (s, 3H), 1.50 (m, 2H), 1.37 (m, 2H), 1.21 (d, 3H), 0.94 (t, 3H).

C. In a manner similar to that set forth in paragraph A, but substituting for N-acetylcysteamine, the various N-acylcysteamines prepared in Preparation B, the corresponding N-acylcysteamine thioesters of (2S,3R)-2-methyl-3-hydroxyhexanoate were prepared.

EXAMPLE 2

Comparative Feeding of Diketide N-Acylcysteamine Thioesters

The N-acylcysteamine thioesters of (±)-(2S*,3R*)-2-methyl-3-hydroxy-hexanoate were fed to growing cultures of *Streptomyces coelicolor* CH999/pJRJ2, and the production of 15-methyl-6-deoxyerythronolide B was monitored. Duplicate cultures were grown in 50 ml of medium (sucrose (103 g/l), $K_2SO_4$ (0.25 g/l), $MgCl_2.6H_2O$ (10.12 g/l), casaminoacids (0.1 g/l), yeast extract (5 g/l), TES buffer (5.73 g/l), sodium propionate (10 mM), and trace elements) supplemented with 50 ug/ml of thiostrepton. After 2 days post-inoculation, the cultures were fed with a solution of diketide thioester in 9:1 water/DMSO to give a final concentration of 0.5 mM diketide thioester. Aliquots of the cultures were removed periodically and assayed for polyketide production by HPLC, with quantitation performed by evaporative light scattering. Production of 15-methyl-6-dEB 6 days after feeding was as follows:

| Acyl group | Yield of 15-methyl-6-dEB |
|---|---|
| Acetyl | 26 mg/L |
| Propionyl | 35 mg/L |
| Butyryl | 30 mg/L |
| Pentanoyl | 35 mg/L |
| Hexanoyl | 33 mg/L |
| Heptanoyl | 27 mg/L |
| Octanoyl | 23 mg/L |

These preliminary results indicate that relatively little difference in yield is obtained depending on the acyl group coupled to cysteamine, but that an optimum chain length at least with respect to the diketide tested, is between 3–6C in the acyl group.

The following examples 3–6 describe the preparation of additional optically active forms of N-acylcysteamines

EXAMPLE 3

Preparation of (2S,3R)-2-Methyl-3-hydroxy-4-pentenoate N-Acetylcysteamine Thioester A. (4S)-N-[(2S,3R)-2-Methyl-3-hydroxy-4-pentenoyl]-4-benzyl-2-oxazolidinone A dry, 2 L three-necked round bottomed flask equipped with a 500 ml addition funnel, a low-temperature therrnometer, and a stir bar was charged with 20.0 g of propionyl oxazolidinone A, capped with septa and flushed with nitrogen. Anhydrous dichloromethane (100 ml) was added and the resulting solution was cooled to −15° C. in a bath of methanol/ice. Dibutylboron triflate (100 ml of 1.0M in dichloromethane) was added in a slow stream via the addition funnel at such a rate as to keep the reaction temperature below 3° C. Diisopropylethylamine (17.9 ml) was added dropwise by syringe, again keeping the internal temperature below 3° C. The reaction was then cooled to −65° C. using a dry ice/isopropanol bath. Acrolein was added over 5 minutes by syringe. The reaction was allowed to stir for 30 min after completion of addition.

The reaction was then transferred to an ice bath and the addition funnel was charged with 120 ml (0.1 mol) of a 1 M aqueous phosphate solution, pH 7.0 (the phosphate solution is comprised of equal molar amounts of mono- and dibasic phosphate). The phosphate solution was added as quickly as possible while keeping the reaction temperature below 10° C. The addition funnel was then charged with 400 ml methanol which was added as quickly as possible while keeping the reaction temperature below 10° C. Finally, the addition funnel was charged with 400 ml of 2:1 methanol-30% hydrogen peroxide. This was added dropwise at first to ensure that the temperature was kept below 10° C. The reaction was stirred for one hour. The solvent was then removed by rotary evaporation until a slurry remained. The slurry was extracted 4 times with 500 ml portions of ethyl ether. The organic extracts were combined and washed with 250 ml each of saturated sodium bicarbonate and brine, then dried with $MgSO_4$, filtered, and concentrated to give a slightly yellow oil. Trituration with hexane induced crystallization. Recrystallization from ether by addition of hexane resulted in 13.67 g (55% yield) of product. $^1$H-NMR (360 MHz, $CDCl_3$): δ 7.2–7.4 (m, 5H); 5.86 (ddd, 1H), 5.35 (dt, 1H), 5.22 (dt, 1H), 4.71 (m, 1H), 4.51 (m, 1H), 4.21 (m, 2H), 3.89 (dq, 1H), 3.26 (dd, 1H), 2.80 (dd, 1H), 1.25 (d, 3H).

B. (2S,3R)-2-Methyl-3-hydroxy-4-pentenoate N-Acetylcysteamine Thioester

N-acetylcysteamine was distilled at 130°/7 mm to give a colorless liquid at room temperature. A dry, 1 L three-necked round bottomed flask equipped with a 500 ml addition funnel and a stir bar was capped with septa and flushed with nitrogen. The flask was then charged with 7.5 ml of N-acetylcysteamine by syringe and with 500 ml of anhydrous THF by cannula. The reaction was then cooled with a MeOH/ice bath. Butyllithium (44 ml of 1.6 M in hexane) was added dropwise by syringe. A white precipitate formed as the n-BuLi was added. After stirring for 30 min, 35.5 ml (0.071 mol) of trimethylaluminum (2.0 M in hexane) was added dropwise by syringe. The reaction became clear after addition of trimethylaluminum and was allowed to stir an additional 30 min. (4S)-N-[(2S,3R)-2-methyl-3-hydroxy-4-pentenoyl]-4-benzyl-2-oxazolidinone from paragraph A (13.6 g) was put under a blanket of nitrogen, dissolved in 50 ml of anhydrous THF, and this solution was then transferred in a slow stream by cannula into the reaction. The resulting reaction mixture turned a yellow-green color and was allowed to stir for 1 hr. The reaction was judged to be finished when starting material could no longer be seen by thin-layer chromatography (ca. 30 min).

Enough saturated oxalic acid was added to give a neutral reaction with pH paper (approximately 60 ml). The solvents were then removed by rotary evaporator to give a white slurry. The slurry was extracted six times with 250 ml portions of ethyl ether The organic extracts were combined, washed with brine, dried with $MgSO_4$, filtered, and concentrated to give a slightly yellow oil. The thioester was then purified by flash chromatography on $SiO_2$. The column was run with 1:1 hexanes:ethyl acetate until the elution of oxazolidinone. At that point, the eluent was switched to 100% ethyl acetate to give pure fractions of product. The fractions were combined and concentrated to give 7.7 g (71% yield) of product. $^1$H-NMR (360 MHz, $CDCl_3$): δ 5.82 (ddd, 1H), 5.78 (br s, 1H), 5.32 (dt, 1H), 5.21 (dt, 1H), 4.47 (m, 1H), 3.45 (m, 2H), 3.04 (m, 2H), 2.81 (dq, 1H), 1.96 (s, 3H), 1.22 (d, 3H).

EXAMPLE 4

Preparation of (2S,3R)-2-Methyl-3-hydroxy-4-pentynoate N-Acetylcysteamine Thioester A. (4S)-N-[(2S,3R)-2-Methyl-3-hydroxy-5-trimethylsilyl-4-pentynoyl]-4-benzyl-2-oxazolidinone Prepared according to the method of Example 1, paragraph A by reaction of (4S)-N-propionyl-4-benzyl-2-oxazolidinone with 3-trimethylsilylpropargyl aldehyde in 80% yield.

B. (4S)-N-[(2S,3R)-2-Methyl-3-hydroxy-4-pentynoyl]-4-benzyl-2-oxazolidinone

A solution of (4S)-N-[(2S,3R)-2-methyl-3-hydroxy-5-trimethylsilyl-4-pentynoyl]-4-benzyl-2-oxazolidinone (0.13 g) in 3 mL of dimethylformamide was treated with 48% aqueous HF (2.6 uL) and $KF.2H_2O$ at ambient temperature for 100 min. Upon completion of the reaction, saturated aqueous sodium bicarbonate was added to neutralize the HF, and the mixture was extracted three times with equal portions of ether. The organic extracts were combined, filtered, and dried over MgSO4. Filtration and evaporation gave the crude product, which was purified by silica gel chromatography (3:2 hexanes/ethyl acetate) to yield 64 mg of product.

C. (2S,3R)-2-Methyl-3-hydroxy-4-pentynoate N-Acetylcysteamine Thioester

In a 25 ml round bottom flask purged with $N_2$, N-acetyl cysteamine (0.12 ml, 1.1 mmol, 1.1 eq) was dissolved in 5.2 ml of anhydrous THF. The solution was cooled to 0° C. A 1.6 M solution of butyllithium in hexanes (0.68 ml, 1.1 mmol, 1.1 eq) was added with a syringe to give a heterogeneous mixture. A 2.0 M solution of trimethylaluminum in hexanes (0.55 ml, 1.1 mmol, 1.1 eq) was added dropwise with vigorous stirring to give a yellow-green solution. A solution of (4S)-N-[(2S,3R)-2-methyl-3-hydroxyl-4-pentynoyl]-4-benzyl-2-oxazolidinone (280 mg, 1.0 mmol, 1.0 eq) in 2 ml of THF was added. The solution was stirred for 15 min and neutralized with saturated oxalic acid (aq). Volatiles were removed in vacuo. The resulting slurry was extracted with 4×20 ml of ethyl acetate. The combined extracts were washed with a minimum of saturated aqueous $CuSO_4$ to remove excess thiol. Some distilled water was used to aid separation. The organic layer was dried over $MgSO_4$, filtered and concentrated. The resulting oil was purified by flash chromatography to give 191 mg of title compound (83% yield) as a pale yellow oil. $^1$H-NMR (400 MHz, $CDCl_3$): δ 5.76 (br s, 1H); 4.68 (dd, 1H, J=2,4); 3.47 (m, 2H); 3.05 (m, 2H), 2.9 (dq, 1H), 2.8 (br d, 1H); 2.51 (d, 1H, J=2); 1.97 (s, 3H); 1.38 (d, 3H, J=7).

D. Preparation of (2S,3R)-5-Fluoro-2-methyl-3-hydroxypentanoate N-Acetylcysteamine Thioester Prepared according to the procedure of Example 3, paragraph B, from (4S)-N-[(2S,3R)-5-fluoro-2-methyl-3-hydroxypentanoyl]-4-benzyl-2-oxazolidinone and N-acetylcysteamine. C-NMR (100 MHz, $CDCl_3$): δ 203.53, 170.65, 81.22 (d, $J_{CF}$=163), 68.48 (d, $J_{CF}$=4), 53.42, 39.12, 34.99 (d, $J_{CF}$=26), 28.54, 23.07, 11.33.

EXAMPLE 5

Preparation of (4S,5R)-4-Methyl-5-hydroxy-2-heptenoate N-Acetylcysteamine Thioester A. (4S)-N-[(2S,4S,5R)-2,4-Dimethyl-5-hydroxy-3-oxoheptanoyl]-4-benzyl-2-oxazolidinone A solution of 2.0 g of (4S)-N-[(2S)-2-methyl-3-oxopentanoyl]-4-benzyl-2-oxazolidinone (prepared according to the procedure of Evans, et al., *Tetrahedron* (1992) 48:2127–2142) in 18 ml of $CH_2Cl_2$ was cooled to −15° C., and 0.89 ml of $TiCl_4$ was added dropwise over 3 minutes, followed by addition of 1.38 ml of diisopropylethylamine over 10 minutes. After stirring for 30 minutes, the mixture was cooled to −78° C. and 0.55 ml of propionaldehyde was added over 20 minutes. The mix was stirred overnight, then quenched with 20 ml of saturated $NH_4Cl$ and allowed to warm to ambient temperature. Water (5 ml) was added, and the resulting mixture was extracted three times with 75 ml portions of ether. The organic extracts were combined, washed with saturated $NH_4Cl$, saturated $NaHCO_3$, and brine, then dried over $MgSO_4$ and concentrated. The crude product was purified by chromatography on $SiO_2$ using a gradient from 9:1 to 1:1 hexanes/ethyl acetate, yielding 1.9 gm (79%) of the product.

B. (4S)-N-[(2S,3S,4S,5R)-2,4-Dimethyl-3,5-dihydroxyhentanoyl]-4-benzyl-2-oxazolidinone Tetramethylammonium triacetoxyborohydride (2.89 g) was dissolved in a mixture of acetic acid (11 ml) and acetonitrile (11 ml), stirred for 30 minutes at ambient temperature, then cooled to −15° C. before addition of (4S)-N-[(2S,4S,5R)-2,4-dimethyl5-hydroxy-3-oxoheptanyl]-4-benzyl-2-oxazolidinone (0.764 g). After stirring for 4 hours, 34 ml of 0.5 M sodium tartrate was added and stirring was continued for an additional 3 hours. After extraction with 3 portions of $CH_2Cl_2$, the organic phases were combined and dried over $MgSO_4$. The solvent was removed under vacuum, and the crude product was evaporated 3 times from 50 ml of methanol to yield 0.644 g of product (84%).

C. (4S)-N-[(2S,3S,4S,5R)-2,4-Dimethyl-3,5-dihydroxyheptanoyl]-4-benzyl-2-oxazolidinone 3',5'-cyclic carbonate Triphosgene (0.138 g) was added to a −15° C. solution of (4S)-N-[(2S,3S,4S,5R)-2,4-dimethyl-3,5-dihydroxyheptanoyl]-4-benzyl-2-oxazolidinone (0.175 g), diisopropylethylamine (0.52 ml) and 4-dimethylaminopyridine (0.02 g) in 2 ml of $CH_2Cl_2$. After stirring for 16 hours, the reaction was quenched by addition of 2 ml of sat. $NH_4Cl$ and was extracted with ethyl acetate. The organic extract was washed with sat. $NH_4Cl$ and brine, then concentrated to give an orange oil. Chromatography ($SiO_2$) gave the pure cyclic carbonate (71 mg).

D. (4S)-N-[(4S,5R)-4-Methyl-5-hydroxy-2-heptenoyl]-4-benzyl-2-oxazolidinone

A solution of (4S)-N-[(2S,3S,4S,5R)-2,4-dimethyl-3,5-dihydroxyheptanoyl]-4-benzyl-2-oxazolidinone 3',5'-cyclic carbonate (71 mg) in 4 ml of tetrahydrofuran was treated with 0.052 ml of diazabicycloundecene at ambient temperature for 16 hours. Addition of 5 ml of sat. $NH_4Cl$ followed by extraction with ethyl acetate and evaporation of solvent yielded crude product, which was chromatographed on $SiO_2$ to give pure material (31 mg, 50%).

E. (4S,5R)-4-Methyl-5-hydroxy-2-heptenoate N-Acetylcysteamine Thioester

A solution of N-acetylcysteamine (0.064 ml) in 3.4 ml of tetrahydrofuran at −15° C. was treated with 0.38 ml of 1.6 M n-butyllithium in hexanes followed by 0.30 ml of 2.0 M trimethylaluminum in hexanes and stirred for 30 minutes. A 0.54 ml portion of this solution was then added to a solution of 31 mg of (4S)-N-[(4S,5R)-4-methyl-5-hydroxy-2-heptenoyl]-4-benzyl-2-oxazolidnone in 0.3 ml of tetrahydrofuran and the mixture was stirred for 2 hours before neutralization with saturated aqueous oxalic acid.

EXAMPLE 6

Additional Precursors to Optically Active N-Acyl Cysteamine Thioesters

A. Preparation of (4S)-N-[(2S,3R)-2-Methyl-3-hydroxybutanoyl]-4-benzyl-2-oxazolidinone:

Prepared from (4S)-N-propionyl-4-benzyl-2-oxazolidinone and acetaldehyde according to the procedure described in Example 1, paragraph A. $^1$H-NMR (360 MHz, $CDCl_3$): δ 7.2–7.4 (m, 5H); 4.71 (m, 1H); 4.12–4.25 (m, 2H); 3.76 (dq, 1H); 3.26 (dd, 1H); 2.79 (dd, 1H); 1.30 (d, 3H), 1.21 (d, 3H).

B. Preparation of (4S)-N-[(2S,3R)-2-Vinyl-3-hydroxypentanoyl]-4-benzyl-2-oxazolidinone:

A solution of 2.45 g of (4S)-N-crotonyl-4-benzyl-2-oxazolidinone in 10 ml of anhydrous $CH_2Cl_2$ was cooled to −78° C., and 1.7 ml of triethylamine was added followed by 10.5 ml of a 1 M solution of dibutylboron triflate in $CH_2Cl_2$. After 30 minutes, the reaction was warmed to 0° C., kept for 20 minutes, then recooled to −78° C. Propionaldehyde (0.9 ml) was added, and the reaction was allowed to slowly warm to ambient temperature over 16 hours. Standard oxidative workup yielded the product (1.98 g, 65% yield) after chromatography (2:1 hexane/ethyl acetate). $^1$H-NMR (360 MHz, $CDCl_3$): δ 7.2–7.35 (m, 5H); 6.02 (1H, m); 5.41 (m, 2H); 4.72 (m, 1H); 4.58 (dd, 1H); 4.20 (m, 2H); 3.92 (m, 1H); 3.25 (dd, 1H); 2.98 (br s, 1H); 2.76 (dd, 1H); 1.53 (m, 2H); 0.98 (t, 3H).

C. Preparation of (4S)-N-[(2S,3R)-2-Methyl-3-hydroxy-3-(3-pyridyl)propanoyl]-4-benzyl-2-oxazolidinone

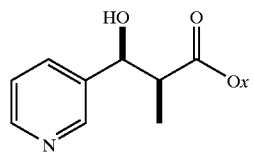

Prepared from (4S)-N-propionyl-4-benzyl-2-oxazolidinone and pyridine-3-carboxaldehyde according to the procedure described in Example 1, paragraph A. $^{13}$C-NMR (100 MHz, $CDCl_3$): δ 176.40, 152.83, 148.74, 147.85, 136.78, 134.80, 134.04, 129.34, 128.95, 127.45, 123.21, 109.75, 71.46, 66.23, 55.05, 44.28, 37.70, 10.64.

D. (4S)-N-[(2S,3R)-5-Fluoro-3-hydroxy-2-methylpentanoyl)]-4-benzyl-2-oxazolidinone

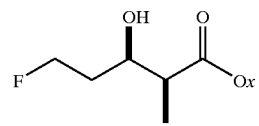

(a) A solution of 3-fluoropropanol in dichloromethane was oxidized with the Dess-Martin periodinane. Analysis by $^1$H-NMR revealed complete oxidation to 3-fluoropropanal. The suspension was filtered, washed with saturated sodium thiosulfate, then dried over $MgSO_4$. $^1$H-NMR ($CDCl_3$, 400 MHz): δ 9.8 (t, 1H), 4.8 (dt, 2H), 2.85 (dt, 2H).

(b) The aldol adduct was prepared according to the method of Example 1, paragraph A by reaction of (4S)-N-propionyl-4-benzyl-2-oxazolidinone with the solution of 3-fluoropropanal. $^{13}$C-NMR(100 MHz, $CDCl_3$): δ 177.08, 153.00, 134.94, 129.37, 128.91, 127.39, 81.16 (d, $J_{CF}$=163), 67.67 (d, $J_{CF}$=4), 66.20, 55.08, 42.23, 37.71, 34.52 (d, $J_{CF}$=19), 10.68.

Examples 7–14 illustrate the preparation of racemic diketide thioesters.

EXAMPLE 7

Preparation of 2-Benzoxazolone and Chlorozoxazone Intermediates

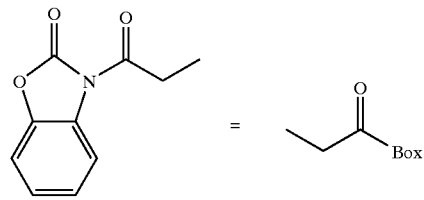

A. N-Propionyl-2-benzoxazolone

A solution of 135 g of 2-benzoxazolone (1.0 mol) in 750 mL of acetone was treated with 14 g (0.1 mol) of potassium carbonate and with 130 mL (1.0 mol) of propionic anhydride at ambient temperature with stirring. After 4 hours, the mixture was poured into 3000 mL of water with vigorous stirring. The precipitated product was collected by vacuum filtration, washed with water, and air dried to yield 187 g (98%) of light tan-colored product suitable for further use; mp=88–90° C. (uncorr). Recrystallization from ether/hexane yields the pure product, 172 g (90% yield), mp=92–93° C. (uncorr). $^1$H-NMR ($CDCl_3$, 400 MHz): δ 8.07 (1H, m); 7.21 (1H, m); 7.22–7.28 (2H, m); 3.12 (2H, q, J=7 Hz); 1.28 (3H, t, J=7 Hz). $^{13}$C-NMR ($CDCl_3$, 100 MHz): δ 173.3, 151.3, 142.2, 127.8, 125.1, 124.7, 115.9, 109.7, 30.4, 7.9.

B. N-Propionylchlorzoxazone

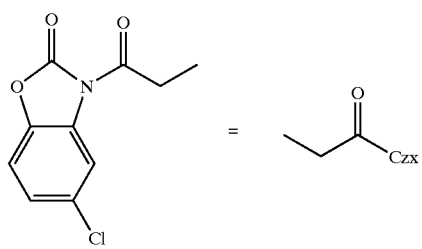

A solution of 17 g of chlorzoxazone (5-chloro-2-benzoxazolone) (0.1 mol) in 75 mL of acetone was treated with 1.0 g (0.007 mol) of potassium carbonate and 15 mL (0.12 mol) of propionic anhydride at ambient temperature with stirring. After 4 hours, the mixture was poured into 300 mL of water with vigorous stirring. The precipitated product was collected by vacuum filtration, washed with water, and air dried to yield 22 g (98%) of colorless product; mp=97–99° C. (uncorr). $^1$H-NMR (CDCl$_3$, 400 MHz): δ 8.11 (d, 1H, J=2 Hz); 7.23 (dd, 1H, J=2,9 Hz); 7.13 (d, 1H, J=9 Hz); 3.12 (q, 2H, J=7 Hz); 1.28 (t, 3H, J=7 Hz). $^{13}$C-NMR (CDCl$_3$, 100 MHz): δ 173.08, 150.97, 140.67, 130.29, 128.45, 125.16, 116.41, 110.59, 30.41, 7.89.

C. (±)-N-[(2R*,3S*)-(2-Methyl-3-hydroxyhexanoyl)]-2-benzoxazolone

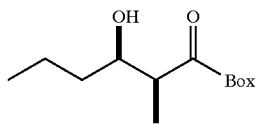

A solution of N-propionyl-2-benzoxazolone (100.0 g) in anhydrous CH$_2$Cl$_2$ (1100 mL) was cooled to 3° C. with mechanical stirring under N$_2$ atmosphere. TiCl$_4$ (58.4 mL) was added at a rate such that the internal temperature remained below 10° C. (ca. 10 minutes). The resulting yellow slurry was stirred vigorously for 40 minutes, then triethylamine (87.4 mL) was added at a rate such that the internal temperature remained below 10° C. (ca. 10 minutes). The resulting deep red solution was stirred for 80 minutes. Butyraldehyde (58.9 mL) was added at a rate such that the internal temperature remained below 10° C. (ca. 20 minutes), and the reaction was followed by thin-layer chromatography (4:1 hexanes/ethyl acetate). After stirring for 90 minutes, the reaction was quenched by addition of 450 mL of 2 N HCl. The phases were separated, and the aqueous phase was extracted 3 times with 750-mL portions of ether. The organic phases were combined and washed three times with 200-mL portions of 2 N HCl. The acidic washes were combined and back-extracted 3 times with 150-mL portions of ether. The combined organic extract was washed once with 300 mL of sat. aq. NaHCO$_3$, and once with 300 mL of sat. aq. NaCl. The organic phase was then dried over MgSO$_4$, filtered, and concentrated under vacuum to a yellow slurry. The product was collected by vacuum filtration and rinsed with hexanes to yield a colorless solid. Concentration of the filtrate yielded a second crop of product, which was collected in the same manner, giving a combined 103 g (80% yield) of crystalline product; mp=123–4° C. The mother liquor can be chromatographed (4:1 hexanes/ethyl acetate) to yield additional product. $^1$H-NMR (CDCl$_3$, 400 MHz): δ 8.10 (1H, m), 7.23–7.32 (3H, m), 4.12 (1H, m), 3.98 (1H, dq, J=3,7), 2.26 (1H, br s), 1.38–1.64 (4H, m), 1.34 (3H, d, J=7), 0.98 (3H, t, J=7). $^{13}$C-NMR (CDCl$_3$, 100 MHz): δ 176.4, 151.1, 142.2, 127.8, 125.5, 124.9, 116.3, 109.9, 71.3, 43.7, 36.2, 19.2, 13.9, 10.1.

D. (±)-N-[(2R*,3S*)-(2-Methy-3-hydroxy-4-pentenoyl)]-2-benzoxazolone

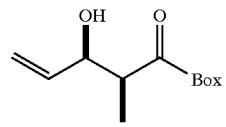

This compound was prepared according to the procedure of paragraph C, by reaction of N-propionyl-2-benzoxazolone with acrolein. $^1$H-NMR (CDCl$_3$, 400 MHz) δ 8.06 (m, 1H), 7.27–7.20 (m, 2H), 5.91 (ddd, J=17, 10, 5 Hz). 5.37 (dt, J=1, 17 Hz, 1H), 5.24 (dt, J=1, 10 Hz, 1H), 4.60 (m, 1H), 4.06 (dq, J=3, 6 Hz, 1H), 2.62 (d, J=4 Hz, 1H), 1.30 (d, 6 Hz, 3H). $^{13}$C-NMR (CDCl$_3$, 100 MHz) δ 175.4, 151.1, 142.2, 137.2, 127.7, 125.5, 124.9, 116.6, 116.2, 109.9, 72.7, 44.0, 10.7.

E. (±)-N-[(2R*,3S*)-(2-Methyl-3-hydroxyheptanoyl)]-2-benzoxazolone

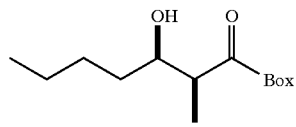

This compound was prepared according to the method of paragraph C by reaction of N-propionyl-2-benzoxazolinone with pentanal.

F. (±)-N-[(2R*,3S*)-(2-Methyl-3-hydroxy-6-heptenoyl)]-2-benzoxazolone

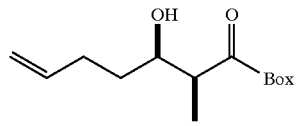

Was prepared according to the method of paragraph C by reaction of N-propionyl-2-benzoxazolinone with 4-pentenal. $^{13}$C-NMR (CDCl$_3$, 100 MHz): δ 176.28, 151.07, 142.20, 137.96, 127.75, 125.50, 124.89, 116.26, 115.19, 109.89, 70.93, 43.76, 33.12, 30.16, 10.21.

G. (±)-N-[(2R*,3S*)-(2-Methyl-3-hydroxyoctanoyl)]-2-benzoxazolone

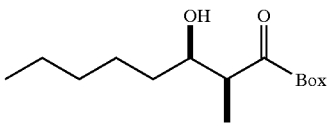

Was prepared according to the method of paragraph C by reaction of N-propionyl-2-benzoxazolinone with hexanal.

H. (±)-N-[(2R*,3S*)-(2,5-Dimethyl-3-hydroxyhexanoyl)]-2-benzoxazolone

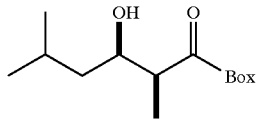

Prepared according to the method of paragraph C by reaction of N-propionyl-2-benzoxazolinone with 3-methylbutanal. ¹H-NMR (CDCl₃, 400 MHz): δ 8.06 (m, 1H); 7.25 (m, 3H); 4.17 (m, 1H); 3.91 (dq, 1H, J=3,7); 2.52 (br s, 1H); 1.82 (m, 1H); 1.56 (ddd, 1H, J=5,9,13); 1.31 (d, 3H, J=7); 1.25 (ddd, 1H, J=4,6,13); 0.95 (d, 3H, J=7); 0.94 (d, 3H, J=7).

I. (±)-N-[(2R*,3S*)-(2-Methyl-3-hydroxy-5-phenylpentanoyl)]-2-benzoxazolone

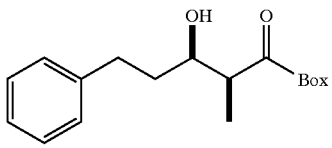

Prepared according to the method of paragraph C by reaction of N-propionyl-2-benzoxazolinone with 3-phenylpropanal. ¹H-NMR (CDCl₃, 400 MHz): δ 8.06 (m, 1H); 7.25 (m, 8H); 4.11 (dt, 1H, J=4,7); 3.96 (dq, 1H, J=3,7); 2.91 (m, 1H); 2.70 (m, 1H); 1.95 (m, 1H); 1.81 (m, 1H); 1.34 (t, 3H, J=7).

J. (±)-N-[(2R*,3S*)-(4-(2-Methoxyethoxy)-2-methyl-3-hydroxybutanoyl)]-2-benzoxazolone

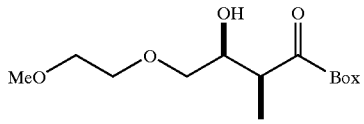

Prepared according to the method of paragraph C by reaction of N-propionyl-2-benzoxazolinone with (2-methoxyethoxy)acetaldehyde. ¹³C-NMR (CDCl₃, 100 MHz): δ 175.01, 151.02, 142.18, 127.91, 125.30, 124.77, 116.15, 109.76, 73.23, 71.86, 70.73, 70.64, 58.88, 41.63, 11.88.

K. (±)-N-[(2R*,3S*)-(2-Methyl-3-hydroxy-3-phenylpropanoyl)]-2-benzoxazolone

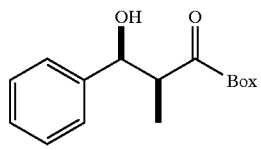

Prepared according to the method of paragraph C by reaction of N-propionyl-2-benzoxazolinone with benzaldehyde; mp 155–158° C. ¹H NMR (CDCl₃) δ 8.10 (m, 1H), 7.45 (m, 2H), 7.35 (m, 2H), 7.26 (m, 4H), 5.30 (d, 1H), 4.26 (dq, J=3,6 Hz, 1H), 1.26 (d, 3H). ¹³C NMR (CDCl₃) δ 175.6, 151.0, 142.2, 141.0, 128.4, 127.7, 126.0, 125.5, 124.9, 116.3, 110.0, 73.2, 46.0, 10.3.

L. (±)-N-[(2R*,3S*)-(5-Azido-2-methyl-3-hydroxypentanoyl)]-2-benzoxazolone

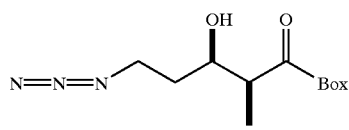

(a) 3-azidopropanal was prepared by addition of HN₃ to acrolein according to A. J. Davies, et al. (1967) *J. Chem. Soc.*, 2109–2112, and gave the following NMR data: ¹H-NMR (CDCl₃, 400 MHz): δ 9.80 (t, 1H, J=1 Hz); 3.61 (t, 2H, J=7 Hz); 2.74 (dt, 2H, J=1,7 Hz). ¹³C-NMR (CDCl₃, 400 MHz): δ 199.41, 44.42, 42.70.

(b) The aldol adduct of 3-azidopropanal and N-propionyl-2-benzoxazolone was prepared according to the procedure of paragraph C. ¹H-NMR (CDCl₃, 400 MHz): δ 8.07.(m, 1H); 7.26 (m, 3H); 4.23 (dq, 1H, J=3,10 Hz); 3.96 (dq, 1H, J=3,7 Hz); 3.52 (dd, 2H, J=6,8 Hz); 2.80 (dd, 1H, J=1,3 Hz); 1.84 (m, 2H); 1.75 (m, 2H); 1.34 (d, 3H, J=7 Hz). ¹³C-NMR (CDCl₃, 100 MHz): δ 176.05, 151.07, 142.20, 127.63, 125.63, 124.97, 116.26, 109.96, 68.85, 48.44, 43.80. 32.94, 10.48.

M. (±)-N-[(2R*,3S*)-(5-Chloro-2-methyl-3-hydroxypentanoyl)]-2-benzoxazolone

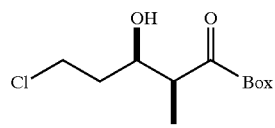

(a) A solution of 3-chloropropanal in CH₂Cl₂ was prepared by addition of HCl to acrolein according to the procedure described above for 3-bromopropanal, and gave the following NMR data: ¹H-NMR (CDCl₃, 400 MHz): δ 9.78 (t, 1H, J=1 Hz); 3.80 (t, 2H, J=7 Hz); 2.93 (dt, 2H, J=1,7 Hz). ¹³C-NMR (CDCl₃, 100 MHz): δ 198.77, 45.90, 36.79.

(b) This solution was reacted with N-propionyl-2-benzoxazolone according to the procedure of paragraph C to yield the product, which was crystallized from ether/hexane; mp=116–7° C. ¹³C-NMR (CDCl₃, 100 MHz): δ 176.12, 151.06, 142.19, 127.63, 125.63, 124.96, 116.25, 109.96, 68.40, 43.68, 41.70, 36.46, 10.55.

N. (±)-N-[(2R*,3S*)-(5-(2-Pyrimidinylthio)-2-methyl-3-hydroxypentanoyl)]-2-benzoxazolone

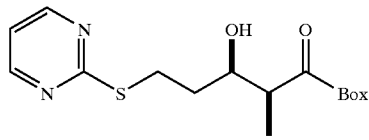

(a) A suspension of 2-mercaptopyrimidine (6 g, 52 mmol) in ethyl acetate (25 mL) was treated with 4 mL of acrolein and 100 mg of tetrabutylammonium hydroxide at 70° C. The bright yellow suspension turned orange and cleared noticeably. After 30 min, the mixture was cooled, filtered, and evaporated to yield 8.53 gm (95%) of the product as an orange oil. ¹H-NMR (CDCl₃, 400 MHz): δ 9.83 (t, 1H, J=1 Hz); 8.51 (d, 2H, J=5 Hz); 7.00 (t, 1H, J=5 Hz); 3.40 (t, 2H, J=7 Hz); 2.97 (dt, 2H, J=1, 7 Hz). ¹³C-NMR (CDCl₃, 400 MHz): δ 200.51, 171.69, 157.30, 116.66, 43.67, 23.31.

(b) The aldol adduct between 3-(2-pyrimidinyl-thio)propanal and N-propionyl-2-benzoxazolone was prepared according to the procedure of paragraph C. ¹H-NMR (CDCl₃, 400 MHz): δ 8.49 (d, 2H, J=5 Hz); 8.07 (m, 1H); 7.25 (m, 3H); 6.97 (t, 1H, 5 Hz); 4.25 (m, 1H); 4.01 (dq, 1H, J=3, 7 Hz); 3.92 (br d, 1H, J=4 Hz); 3.32 (m, 2H); 2.05 (m, 1H); 1.95 (m, 1H); 1.35 (d, 3H, J=7 Hz). ¹³C-NMR (CDCl₃, 100 MHz): δ 175.58, 172.66, 157.28, 151.04, 142.16, 127.81, 125.38, 124.81, 116.51, 116.22, 109.81, 69.62, 43.87, 34.29, 27.34, 10.89.

O. (±)-N-[(2R*,3S*)-(3-Hydroxy-2,4,4-trimethylpentanoyl)]-2-benzoxazolone

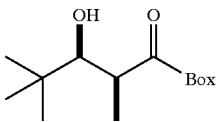

Prepared according to the method of paragraph C by reaction of N-propionyl-2-benzoxazolone with trimethylacetaldehyde. Slow addition of the aldehyde to the enolate solution over 1 hour at 0° C. gave a 9:1 ratio of the (2R*,3S*) and (2R*,3R*) isomers. The desired isomer was crystallized from 1:1 ether/hexanes, mp=90–2° C. ¹H-NMR (CDCl₃, 400 MHz) δ 8.04 (m, 1H), 7.23–7.29 (m, 3H), 4.32 (dq, J=3, 7 Hz, 1H), 3.79 (d, J=10 Hz, 1H), 3.41 (dd, J=3,10 Hz, 1H), 1.51 (d, J=7 Hz, 3H), 0.94 (s, 9H). ¹³C-NMR (CDCl₃, 100 MHz) δ 178.2, 150.8, 142.0, 127.6, 125.7, 125.0, 116.3, 110.0, 84.0, 37.4, 36.2, 26.7, 18.1.

P. (±)-N-[(2R*,3R*)-(3-Hydroxy-2,4,4-trimethylpentanoyl)]-2-benzoxazolone

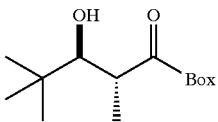

Prepared according to the method of paragraph C by reaction of N-propionyl-2-benzoxazolone with trimethylacetaldehyde. Rapid addition of the aldehyde to the enolate solution at 0° C. gave a 1:1 ratio of the (2R*,3S*) and (2R*,3R*) isomers. The desired isomer was isolated by silica gel chromatography, then crystallized. ¹H-NMR (CDCl₃, 400 MHz) δ 8.05 (m, 1H), 7.20–7.27 (m, 4H), 4.24 (dq, J=7,4 Hz, 1H), 3.82 (br t, J=4 Hz, 1H), 2.33 (br d, J=4 Hz, 1H), 1.36(d, J=7 Hz, 3H), 0.99, (s, 9H). ¹³C-NMR (CDCl₃, 100 MHz) δ 175.3, 150.8, 142.2, 127.9, 125.4, 124.9, 116.2, 109.9, 77.6, 40.3, 35.8, 29.7, 26.7, 12.7.

Q. (±)-N-[(2R*,3S*)-4-Benzyloxy-3-hydroxy-2-methylbutanoyl)]-2-benzoxazolone and (±)-N-[(2R*,3R*)-4-benzyloxy-2-methylbutanoyl)]-2-benzoxazolone

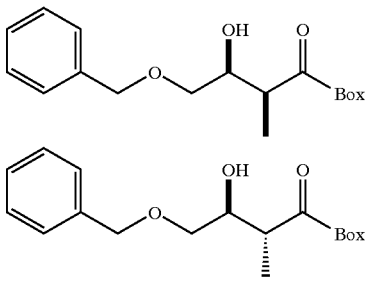

Prepared according to the procedure of paragraph C, by reaction of N-propionyl-2-benzoxazolone with benzyloxyacetaldehyde. The reaction Yielded a 9:1 mixture of (2R*, 3S*) and (2R*,3R*) isomers. The isomers were separated by silica gel chromatography: (2R*,3S*): ¹H-NMR (CDCl₃, 400 MHz) δ 8.03 (m, 1H), 7.20–7.33 (m, 9H), 4.55 (dd, J=25, 8 Hz, 2H), 4.26 (br q, J=5 Hz, 1H), 4.10 (dq, J=5, 6 Hz, 1H), 3.59 (m, 2H), 1.36 (d, 7 Hz, 3H). ¹³C-NMR (CDCl₃, 100 MHz) δ 175.2, 151.0, 142.2, 137.6, 128.4 (2), 127.7 (2), 125.4, 124.8, 116.2, 109.8, 7304, 71.6, 70.7, 41.7, 11.9. (2R*,3R*): ¹H-NMR (CDCl₃, 400 MHz) δ 8.02 (m, 1H), 7.16–7.33 (m, 9H), 4.52 (q, J=12 Hz, 2H), 4.28 (p, J=7 Hz, 1H), 4.04 (br m, 1H), 3.69 (dd, J=3, 10 Hz, 1H), 3.64 (dd, J=5, 10 Hz, 1H), 3.09 (br s, 1H), 1.31 (d, J=7H Hz 3H). ¹³C-NMR (CDCl₃, 100 MHz) δ 175.8, 151.3, 142.0, 137.5, 128.3, 127.8, 127.7, 127.5, 125.3, 124.7, 116.2, 109.7, 73.5, 73.4, 73.0, 41.1, 14.5.

R. (±)-N-[(2R*,3S*)-3-Hydroxy-2-methyl-4-hexenoyl)]-2-benzoxazolone

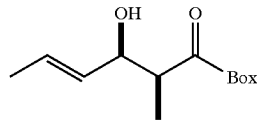

Prepared according to the method of paragraph C by reaction of N-propionyl-2-benzoxazolone with trans-crotonaldehyde; mp 74–6° C. ¹H NMR (CDCl₃) δ 8.06 (m, 1H); 7.23 (m, 3H); 5.78 (dqd, 1H, J=15, 7, 1 Hz); 5.55 (ddq, 1H, J=15, 7, 2 Hz); 4.52 (br, 1H); 4.05 (qd, 1H, J=7, 4 Hz); 2.38 (br d, 1H, J=3 Hz); 1.70 (ddd, 3H, J=7, 1, 1 Hz, 3H); 1.30 (d, 3H, J=7 Hz). ¹³C NMR (CDCl₃) δ 175.50, 151.20, 142.18, 129.99, 128.78, 127.80, 125.43, 124.86, 116.22, 109.85, 72.92, 44.31, 17.71, 11.04.

S. (±)-N-(2-(1-Hydroxycyclohexyl)propionyl)-2-benzoxazolone

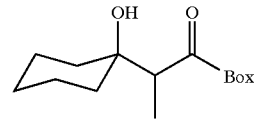

Prepared according to the method of paragraph C by reaction of N-propionyl-2-benzoxazolone with cyclohexanone; mp 58–9° C. ¹H NMR (CDCl₃) δ 8.09 (m, 1H); 7.25 (m, 3H); 4.11 (q, 1H, J=7 Hz); 2.90 (br s, 1H); 1.82 (br d, 1H, J=13 Hz); 1.59 (m, 8H); 1.34 (d, 3H, J=7 Hz); 1.23 (m, 1H). ¹³C NMR (CDCl₃) δ 177.20, 151.42, 142.03, 127.69, 125.55, 124.91, 116.38, 109.88, 72.89, 46.77, 37.03, 33.37, 25.64, 21.73, 21.40, 12.16.

T. (±)-N-[(2R*, 3S*)-6-Benzyloxy-3-hydroxy-2-methylhexanoyl)]-2-benzoxazolone

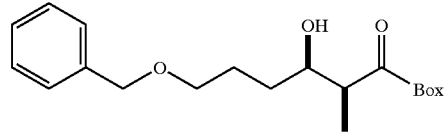

Is prepared according to the method of paragraph C by reaction of N-propionyl-2-benzoxazolone with 4-benzyloxybutyraldehyde.

U. (±)-N-[(2R*,3S*)-6,6,6-Trifluoro-3-hydroxy-2-methylhexanoyl)]-2-benzoxazolone

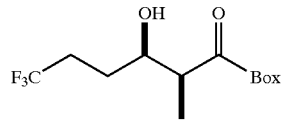

Prepared according to the method of paragraph C by reaction of N-propionyl-2-benzoxazolone with 4,4,4-trifluorobutyraldehyde. ¹H-NMR (CDCl₃, 400 MHz): δ 8.05 (m, 1H); 7.25 (m, 3H); 4.10 (dt, 1H, J=3, 10); 3.95 (dq, 1H, J=3, 7); 2.65 (br s, 1H); 2.43 (m, 1H); 2.17 (m, 1H); 1.76 (m, 2H); 1.33 (d, 3H, J=7). $^{19}$F-NMR (CDCl$_3$, 386 MHz): δ-66.77.

V. (±)-N-[(2R*,3S*)-5-Methylthio-3-hydroxy-2-methylpentanoyl)]-2-benzoxazolone

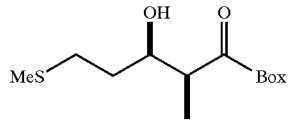

Prepared according to the method of paragraph C by reaction of N-propionyl-2-benzoxazolone with 3-(methylthio)propionaldehyde. $^1$H-NMR (CDCl$_3$, 400 MHz): δ 8.06 (m, 1H); 7.25 (m, 3H); 4.25 (m, 1H); 3.96 (dq, 1H, J=3,7); 2.82 (br d, 1H); 2.68 (m, 2H); 2.11 (s, 3H); 1.90 (m, 1H); 1.78 (m, 1H); 1.34 (d, 3H, J=7).

W. (±)-N-[(2R*,3S*)-4-Cyclohexyl-3-hydroxy-2-methylbutanoyl)]-2-benzoxazolone

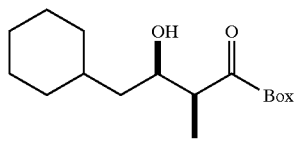

Prepared according to the method of paragraph C by reaction of N-propionyl-2-benzoxazolone with cyclohexylacetaldehyde.

X. (±)-N-[(2R*,3S*)-5-(3-Pyridyl-3-hydroxy-2-methylpentanoyl)]-2-benzoxazolone

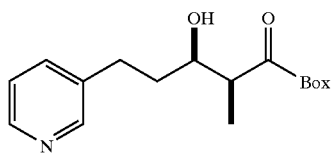

Is prepared according to the method of paragraph C by reaction of N-propionyl-2-benzoxazolone with 3-(3-pyridyl)propanal.

Y. (±)-N-[(2R*,3S*)-3-Hydroxy-2-methyl-5-hexenoyl)-2-benzoxazolone

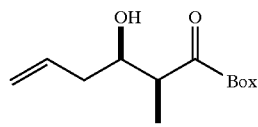

Is prepared according to the method of paragraph C by reaction of N-propionyl-2-benzoxazolone with 3-butenal.

Z. (±)-N-[(2R*,3S*)-4-Methoxy-3-hydroxy-2-methylbutanoyl)]-2-benzoxazolone

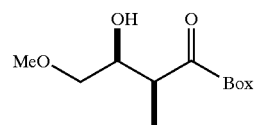

Is prepared according to the method of paragraph C by reaction of N-propionyl-2-benzoxazolone with methoxyacetaldehyde.

AA. (±)-N-[(2R*,3S*)-3-(2-Methylthiazol-4-yl)-3-hydroxy-2-methylpropanoyl)]-2-benzoxazolone

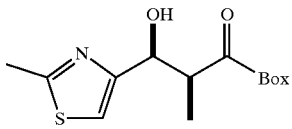

Is prepared according to the method of paragraph C by reaction of N-propionyl-2-benzoxazolone with 2-methylthiazole-4-carboxaldehyde.

BB. (±)-N-[(2R*,3S*)-5-(2-Methylthiazol-4-yl)-3-hydroxy-2-methylpentanoyl)]-2-benzoxazolone

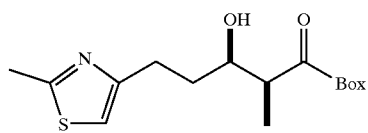

Is prepared according to the method of paragraph C by reaction of N-propionyl-2-benzoxazolone with 3-(2-methylthiazol-4-yl)propanal.

CC. (±)-N-[(2R*,3S*)-3-Hydroxy-2-methyl-5-heptynol)]-2-benzoxazolone

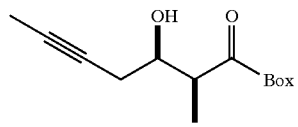

Is prepared according to the method of paragraph C by reaction of N-propionyl-2-benzoxazolone with 3-pentynal.

DD. (±)-N-[(2R*,3S*)-3-(Tetrahydrofuran-2-yl)-3-hydroxy-2-methylpropanoyl)]-2-benzoxazolone

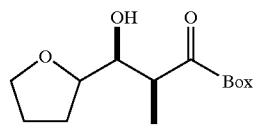

Is prepared according to the method of paragraph C by reaction of N-propionyl-2-benzoxazolone with tetrahydrofuran-2-carboxaldehyde.

EE. (±)-N-[(2R*,3S*)-5-(Methoxycarbonyl)-3-hydroxy-2-methlpentanoyl)]-2-benzoxazolone

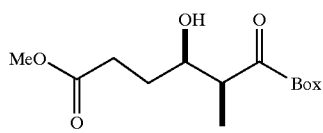

Is prepared according to the method of paragraph C by reaction of N-propionyl-2-benzoxazolone with methyl 4-oxobutanoate.

FF. (±)-N-[(2R*,3S*)-5-Fluoro-3-hydroxy-2-methylpentanoyl)]-2-benzoxazolone

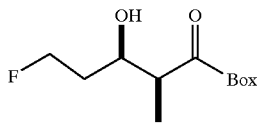

(a) A solution of 3-fluoropropanol in dichloromethane was oxidized with the Dess-Martin periodinane. Analysis by $^1$H-NMR revealed complete oxidation to 3-fluoropropanal. The suspension was filtered, washed with saturated sodium thiosulfate, then dried over MgSO$_4$. $^1$H-NMR (CDCl$_3$, 400 MHz): δ 9.8 (t, 1H), 4.8 (dt, 2H), 2.85 (dt, 2H).

(b) The aldol adduct is prepared according to the method of paragraph C by reaction of N-propionyl-2-benzoxazolone with the solution of 3-fluoropropanal.

GG. (±)-N-[(2R*,3S*)-(5-Phthalimido-2-methyl-3-hydroxypentanoyl)]-2-benzoxazolone

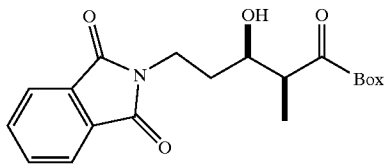

(a) 3-Phthalimidopropanal was prepared by addition of phthalimide to acrolein in the presence of tetrabutylammonium hydroxide according to the procedure described by R. O. Atkinson & F. Poppelsdorf, *J Chem. Soc.* (1952) 2448. $^1$H-NMR (CDCl$_3$, 400 MHz): δ 9.82 (t, 1H, J=2); 7.85 (m, 2H); 7.72 (m, 2H); 4.04 (t, 2H, J=7); 2.88 (dt, 2H, J=2, 7). $^{13}$C-NMR (CDCl$_3$, 100 MHz): δ 199.36, 167.98, 134.10, 131.95, 123.36, 42.35, 31.67.

(b) The aldol adduct was prepared by reacting 3-phthalimidopropanal with N-propionyl-2-benzoxazolone according to the procedure of paragraph C. $^{13}$C-NMR (CDCl$_3$, 100 MHz): δ 175.52, 168.75, 151.02, 142.17, 134.02, 132.05, 127.75, 125.46, 124.87, 123.35, 116.29, 109.85, 69.02, 44.00, 34.93, 33.11, 11.11.

HH. (±)-N-[(2R*,3S*)-(6-Fluoro-2-methyl-3-hydroxyhexanoyl)]-2-benzoxazolone

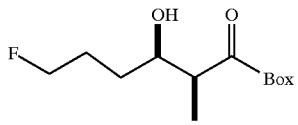

(a) 1-Bromo-3-fluoropropane is reacted with sodium cyanide to give 4-fluorobutyronitrile. The nitrile is reduced with diisobutylaluminum hydride to give 4-fluorobutyraldehyde.

(b) The aldol adduct is prepared by reacting 4-butyraldehyde with N-propionyl-2-benzoxazolone according to the procedure of paragraph C.

EXAMPLE 8

(±)-N-[(2R*,3S*)-(3-Cyclopropyl-2-methyl-3-hydroxylropionyl)]chlorzoxazone

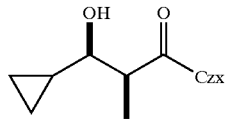

A solution of N-propionylchlorzoxazone (2.25 g, 10 mmol) in anhydrous CH$_2$Cl$_2$ (50 mL) was cooled to 3° C. with mechanical stirring under N$_2$ atmosphere. TiCl$_4$ (1.2 mL) was added at a rate such that the internal temperature remained below 10° C. (ca. 1 minute). The resultingyellow slurry was stirred vigorously for 5 minutes, then triethylamine (1.5 mL) was added at a rate such that the internal temperature remained below 10° C. (ca. 1 minutes). The resulting deep red solution was stirred for 30 minutes. Cyclopropanecarboxaldehyde (0.75 mL) was added in one portion. After stirring for 60 minutes, the reaction was quenched by addition of 40 mL of 2 N HCl. The phases were separated, and the aqueous phase was extracted once with 40-mL of ether. The organic phases were combined, dried over MgSO$_4$, filtered, and concentrated under vacuum to a colorless oil. Recrystallization from 1:1 ether/hexanes yielded 1.89 g of pure product. $^1$H-NMR (CDCl$_3$, 400 MHz): δ 8.12 (d, 1H, J=2 Hz); 7.25 (dd, 1H, J=2, 8 Hz); 7.14 (d, 1H, J=8 Hz); 4.16 (dq, 1H, J=4, 7 Hz); 3.28 (dd, 1H, J=4, 9 Hz); 2.22 (br s, 1H); 1.41 (d, 3H, J=7 Hz); 1.10 (m, 1H); 0.56 (m, 2H); 0.37 (m, 2H). $^{13}$C-NMR (CDCl$_3$, 100 MHz): δ 175.24, 150.7, 140.62, 130.42, 128.54, 125.40, 116.73, 110.64, 44.45, 14.93, 11.03, 3.47, 2.70.

EXAMPLE 9

(±)-N-](2R*,3S*)-(5-Bromo-2-methyl-3-hydroxypentanoyl)]chlorzoxazone

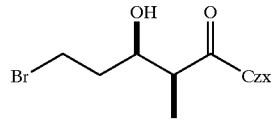

(a) A solution of 3-bromopropanal was prepared by bubbling anhydrous HBr into an ice-cold solution of acrolein (5.6 g, 100 mmol) in dichloromethane (50 mL) containing 5 mg of dicinnamnylacetone as indicator. Once the solution stayed red for 5 minutes after cessation of HBr addition, the solution was checked by $^1$H-NMR by addition of 20 uL to 750 uL of CDCl$_3$. NMR revealed clean conversion to 3-bromopropanal, and relative integration against the CH$_2$Cl$_2$ signal indicated a concentration of 2.6 M 3-bromopropanal. Anhydrous MgSO$_4$ was added to the reaction mixture and stirred to absorb water. This solution was filtered and used directly in the subsequent aldol condensation. $^1$H-NMR (CDCl$_3$, 400 MHz): δ 9.74 (t, 1H, J=1 Hz); 3.61 (t, 2H, J=7 Hz); 3.07 (dt, 2H, J=1, 7 Hz). $^{13}$C-NMR (CDCl$_3$, 400 MHz): δ 198.95, 45.96, 23.35.

(b) A solution of N-propionylchlorzoxazone (11.3 g, 50 mmol) in anhydrous CH$_2$Cl$_2$ (250 mL) was cooled to 3° C. with mechanical stirring under N$_2$ atmosphere. TiCl$_4$ (6.0 mL) was added at a rate such that the internal temperature remained below 10° C. (ca. 1 minute). The resulting yellow slurry was stirred vigorously for 30 minutes, then triethylamine (7.5 mL) was added at a rate such that the internal temperature remained below 10° C. (ca. 1 minutes). The resulting deep red solution was stirred for 30 minutes. The solution of 3-bromopropanal (25 mL, 60 mmol) was added in one portion. After stirring for 30 minutes, the reaction was quenched by addition of 200 mL of 2 N HCl. The phases were separated, and the aqueous phase was extracted once with 200-mL of ether. The organic phases were combined and filtered through a pad of silica, washing the silica with ether. The filtrate was evaporated to yield a tan solid, which was recrystallized from ether by addition of hexane to yield 9.5 g (52%) of the product as a colorless solid. $^1$H-NMR (CDCl$_3$, 400 MHz): δ 8.14 (d, 1H, J=2 Hz); 7.28 (dd, 1H, J=2, 8 Hz); 7.18 (d, 1H, J=8 Hz); 4.33 (dt, 1H, J=3, 10 Hz), 3.96 (dq, 1H, J=4, 7 Hz); 3.61 (m, 2H); 2.3 (br s, 1H); 2.16 (m, 1H); 1.98 (m, 1H); 1.35 (d, 3H, J=7 Hz). $^{13}$C-NMR (CDCl$_3$, 100 MHz): δ 175.76, 150.74, 140.62, 130.54, 128.29, 125.64, 116.78, 110.78, 69.39, 43.71, 36.49, 30.14, 10.66.

EXAMPLE 10

(±)-N-[(2R*,3S*)-(5-Chloro-2-methyl-3-hydroxypentanoyl)]chlorzoxazone

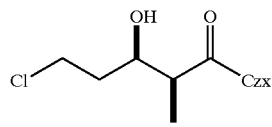

This was prepared according to the procedure for the corresponding bromide of Example 9, using a solution of 3-chloropropanal in dichloromethane. $^1$H-NMR (CDCl$_3$, 400 MHz): δ 8.12 (d, 1H, J=2 Hz); 7.26 (dd, 1H, J=2, 8 Hz); 7.17 (d, 1H, J=8 Hz); 4.33 (m, 1H); 3.94 (dq, 1H, J=4, 7 Hz); 3.74 (m, 2H); 2.70 (br s, 1H); 2.05 (m, 1H); 1.90 (m, 1H); 1.34 (d, 3H, J=7 Hz). $^{13}$C-NMR (CDCl$_3$, 100 MHz): δ 175.79, 150.74, 140.62, 130.53, 128.29, 125.63, 116.77, 110.78, 68.40, 43.76, 41.64, 36.37, 10.59.

EXAMPLE 11

(±)-N-[(2R*,3S*)-3-Hydroxy-2-vinyl-6-heptenoyl)]-2-benzoxazolone

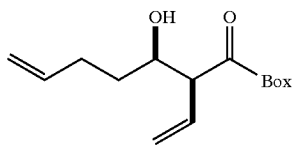

(a) N-crotonyl-2-benzoxazolone: A solution of 2-benzoxazolone (8.1 gm) in 60 mL of acetone was stirred with 8.3 gm of potassium carbonate while trans-crotonyl chloride (5.75 mL) was added dropwise. After 16 hours, the mixture was poured into 150 mL of water, and the resulting precipitate was collected by vacuum filtration and air dried. Recrystallization from ether/hexanes gave 10.5 gm (86%). $^1$H-NMR (CDCl$_3$, 400 MHz): δ 8.12 (m, 1H); 7.40 (m, 2H); 7.25 (m, 4H); 2.07 (m, 3H).

(b) Anhydrous CH$_2$Cl$_2$ (200 mL) was added to a flask containing N-crotonyl-2-benzoxazolone (8.00 g, 39.4 mmol, 1.00 eq) to make a 0.2 M solution which was cooled to −78° C. in a dry ice/acetone bath. Titanium (IV) chloride (4.41 mL, 40.2 mmol, 1.02 equiv) was added dropwise. The yellow slurry was stirred vigorously for 20 min. Freshly distilled triethylamine (6.58 mL, 47.2 mmol, 1.20 equiv) was added dropwise. The color changed from red-orange to deep purple during the addition. The solution was stirred for 1.5 h at −78° C. and 1.5 h at 0° C. The reaction mixture was returned to −78° C.; and freshly distilled 4-penten-1-al (bp 102–103° C.; 4.96 mL, 47.2 mmol, 1.2 equiv) was added dropwise over 15 min. The solution was stirred for 2 h at −78° C. and 1.5 h at 0° C. The color changed from purple to brown over this time. The reaction was quenched with 2 N HCl$_{(aq)}$ (1.5 eq). The mixture was poured into a separatory funnel, and the layers were separated. The organic phase was vacuum filtered through a pad of silica. The silica was washed with 3 volumes of ether, and all of the filtrate was concentrated. The crude material was chromatographed over silica (85:15 hexanes: EtOAc) to give 8.05 g (71 %) of a faintly colored oil. $^{13}$C-NMR (CDCl$_3$, 400 MHz): δ 173.25, 150.90, 142.13, 137.91, 130.42, 127.67, 125.61, 124.91, 121.96, 116.19, 115.16, 109.92, 71.01, 53.79, 33.31, 29.85.

EXAMPLE 12

(4S)-N-[(1S,2R)-2-Hydroxy-5-cyclohexenyl-1-carboxyl]-2-benzoxazolone

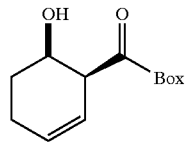

A solution of (4S)-N-[(2S,3R)-3-hydroxy-2-vinyl-6-heptenoyl)]-4-benzyl-2-oxazolidinone (35 mg) and 8 mg of bis(tricyclohexylphosphine) benzylideneruthenium dichloride (Grubbs' catalyst) in dichloromethane (5 mL) was heated at reflux under inert atmosphere for 1.5 h. Chromatography yielded the cyclic metathesized product. $^{13}$C-NMR (CDCl$_3$, 100 MHz): δ 173.10, 153.56, 135.09, 130.30, 19.42, 128.95, 127.39, 121.36, 67.10, 66.30, 55.34, 45.57, 37.84, 27.44, 22.39.

EXAMPLE 13

Conversion to Thioesters

A. (±)-(2R*,3S*)-2-Methyl-3-hydroxyhexanoate N-Propionylcysteamine Thioester

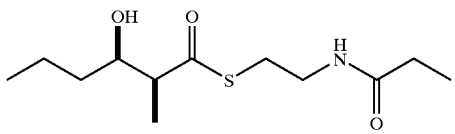

One molar equivalent of sodium methoxide (25% w/v in methanol; ca. 150 mL) is added in a slow stream to a solution of N,S-dipropionylcysteamine (173 g) in methanol (910 mL) under N$_2$. When half of the calculated volume has been added, the reaction is monitored by TLC (1:1 ethyl acetate/hexanes), and methoxide addition is continued until complete conversion of the N,S-dispropionylcysteamine to N-propionylcysteamine.

The resulting solution of sodium N-propionylcysteamine thiolate is cannulated into a flask containing solid (±)-N-[(2R*,3S*)-(2-methyl-3-hydroxyhexanoyl)]-2- benzoxazolone (240 g) under N$_2$. After 15 minutes, the reaction is quenched with solid oxalic acid dihydrate (80.4 g), filtered, and concentrated to a yellow oil. The residue is dissolved in 2:1 hexanes/ethyl acetate and submitted to batch elution chromatography on SiO$_2$. The silica is washed with 2:1 hexanes/ethyl acetate to remove 2-benzoxazolone, then with ethyl acetate/methanol (9:1) to elute the product thioester. Evaporation of the thioester-containing eluent yields 222 g of the thioester (98% yield) as a yellow oil, which crystallizes on standing; mp 37–39° C. $^1$H-NMR (CDCl$_3$, 400 MHz): δ 5.8 (br s, 1H); 3.93 (dt, 1H); 3.44 (m, 2H); 3.03 (dt, 2H); 2.69 (dq, 1H); 2.19 (q, 2H); 1.47 (m, 2H); 1.36 (m, 2H); 1.19 (d, 3H); 1.14 (t, 3H); 0.92 (t, 3H).

The following are prepared according to the method of paragraph A of this example.

B. (±)-(2R*,3S*)-2-Methyl-3-hydroxyhexanoate N-Acetylcysteamine Thioester:

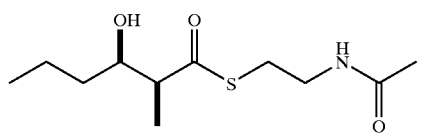

Prepared according to the method of paragraph A, by reaction of N,S-diacetylcysteamine and (±)-N-[(2R*,3S*)-(2-methyl-3-hydroxyhexanoyl)]-2-benzoxazolone. $^1$H-NMR (CDCl$_3$, 400 MHz): δ 6.1 (brs, 1H); 3.93 (dt, 1H); 3.44 (m, 2H); 3.03 (dt, 2H); 2.72 (dq, 1H); 1.97 (s, 3H); 1.51 (m, 2H); 1.37 (m, 2H); 1.23 (d, 3H); 1.14 (t, 3H); 0.94 (t, 3H). $^{13}$C-NMR (CDCl$_3$, 100 MHz): δ 204.05, 170.52, 71.87, 53.40, 39.33, 36.31, 28.53, 23.14, 19.16, 13.91, 11.14.

C. (±)-(2R*,3S*)-2-Methyl-3-hydroxy-4-pentenoate N-Propionylcysteamine Thioester

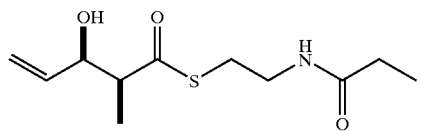

Prepared according to the method of paragraph A, by reaction of N,S-dipropionyl-cysteamine and (±)-N-[(2R*,3S*)-(2-methyl-3-hydroxy-4-pentenoyl)]-2-benzoxazolone.

D. (±)-(2R*,3S*)-5-Chloro-2-methyl-3-hydroxypentanoate N-Acetylcysteamine Thioester

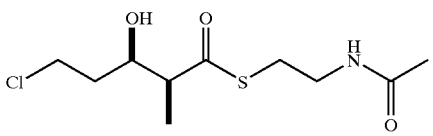

Prepared according to the procedure of paragraph A from N,S-diacetylcysteamine and (±)-N-[(2R*,3S*)-5-chloro-2-methyl-3-hydroxypentanoyl]chlorzoxazone. $^{13}$C-NMR (CDCl$_3$, 100 MHz): δ 203.47, 170.76, 69.01, 53.43, 41.79, 39.13, 36.80, 28.75, 23.17, 11.52.

E. (±)-(2R*,3S*)-5-Bromo-2-methyl-3-hydroxypentanoate N-Acetylcysteamine Thioester

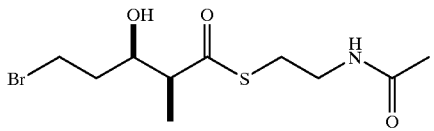

Prepared according to the procedure of paragraph A from N,S-diacetylcysteamine and (+)-N-[(2R*,3S*)-5-bromo-2-methyl-3-hydroxypentanoyl]-chlorzoxazone. $^{13}$C-NMR (CDCl$_3$, 100 MHz): δ 203.32, 170.82, 70.05, 53.44, 39.11, 37.00, 30.41, 28.74, 23.18, 11.64.

F. (±)-(2R*,3S*)-5-Azido-2-methyl-3-hydroxypentanoate N-Acetylcysteamine Thioester

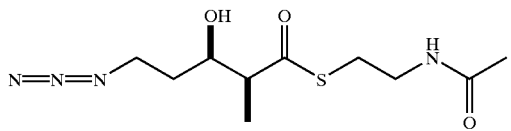

Prepared according to the procedure of paragraph A from N,S-diacetylcysteamine and (±)-N-[(2R*,3S*)-5-azido-2-methyl-3-hydroxypentanoyl]-2-benzoxazolone. $^{13}$C-NMR (CDCl$_3$, 100 MHz): δ 203.41, 170.75, 69.43, 53.62, 48.46, 39.12, 33.22, 28.73, 23.13, 11.57.

G. (±)-(2R*,3S*)-4-(2-Methoxethoxy)-2-methyl-3-hydroxybutanoate N-Propionylcysteamine Thioester

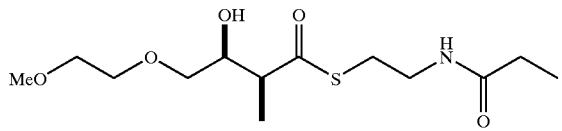

Prepared according to the procedure of paragraph A from N,S-dipropionylcysteamine and (±)-(±)-N-[(2R*,3S*)-(4-(2-methoxyethoxy)-2-methyl-3-hydroxybutanoyl)]-2-benzoxazolone. $^{13}$C-NMR (CDCl$_3$, 100 MHz): δ 202.77, 174.05, 72.83, 71.89, 71.15, 70.66, 58.97, 50.93, 39.30, 29.58, 28.61, 12.73, 9.72.

H. (±)-(2R*,3S*)-5-(2-Pyrimidinylthio)-2-methy-3-hydroxypentanoate N-Propionylcysteamine Thioester

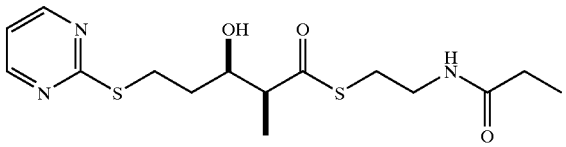

Prepared according to the procedure of paragraph A from N,S-dipropionylcysteamine and (±)-(±)-N-[(2R*,3S*)-(5-(2-pyrimidinylthio)-2-methyl-3-hydroxypentanoyl)]-2-benzoxazolone. $^{13}$C-NMR (CDCl$_3$, 100 MHz): δ 203.23, 174.10, 157.30, 116.57, 70.12, 53.62, 39.28, 34.56, 29.60, 28.61, 27.24, 14.17, 12.26, 9.74

I. (±)-(2R*,3S*)-2-Methyl-3-hydroxy-6-heptenoate N-Acetylcysteamine Thioester

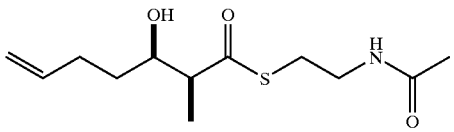

Prepared according to the procedure of paragraph A from N,S-diacetylcysteamine and (±)-N-[(2R*,3S*)-(2-methyl-3-hydroxy-6-heptenoyl)]-2-benzoxazolone. $^{1}$H-NMR (CDCl$_{3}$, 400 MHz): δ 5.91 (br s, 1H), 5.82 (m, 1H), 5.06 (dq, 1H), 4.99 (dq, 1H), 3.94 (m, 1H), 3.47 (m, 2h), 3.03 (m, 2H), 2.73 (dq, 1h), 2.56 (brd, 1H), 2.25 (m, 1H), 2.15 (m, 1H), 1.97 (s, 3H), 1.60 (m, 1H), 1.51 (m, 1H), 1.23 (d, 3H). $^{13}$C-NMR (CDCl$_{3}$, 100 MHz): δ 203.96, 170.44, 137.93, 115.18, 71.55, 53.40, 39.32, 33.30, 30.20, 28.60, 23.18, 11.26.

J. (±)-(2R*,3S*)-2-Methyl-3-hydroxyhexanoate N-Butyrylcysteamine Thioester

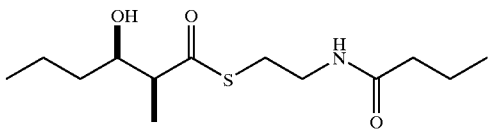

Prepared according to the method of paragraph A using N,S-dibutyrylcysteamine. $^{1}$H-NMR (CDCl$_{3}$): δ 5.85 (br s, 1H), 3.93 (m, 1H), 3.45 (m, 2H), 3.02 (m, 2H), 2.70 (dq, 1H, J=3, 7), 2.13 (m, 3H), 1.65 (m, 2H), 1.49 (m, 2H), 1.33 (m, 2H), 1.21 (d, 3H, J=7), 0.95 (t, 3H, J=7), 0.92 (t, 3H, J=7).

K. (±)-(2R*,3S*)-2-Methyl-3-hydroxyhexanoate N-Pentanoylcysteamine Thioester

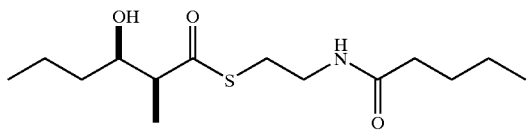

Prepared according to the method of paragraph A using N,S-dipentanoylcysteamine. $^{1}$H-NMR (CDCl$_{3}$): δ 5.81 (br s, 1H), 3.92 (m, 1H); 3.44 (m, 2H), 3.03 (m, 2H), 2.70 (dq, 1H, J=3, 7), 2.15 (m, 3H), 1.6 (m, 2H), 1.5 (m, 2H), 1.35 (m, 4H), 1.21 (d, 3H, J=7), 0.93 (t, 3H, J=7), 0.91 (t, 3H, J=7).

L. (±)-(2R*,3S*)-2-Methyl-3-hydroxyhexanoate N-Hexanoylcysteamine Thioester

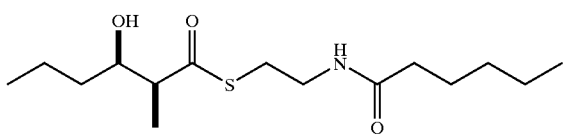

Prepared according to the method of paragraph A using N,S-dihexanoylcysteamine. $^{1}$H-NMR (CDCl$_{3}$): δ 5.83 (br s, 1H), 3.92 (m, 1H); 3.44 (m, 2H), 3.03 (m, 2H), 2.69 (dq, 1H, J=3, 7), 2.14 (m, 3H), 1.6 (m, 2H), 1.45 (m, 2H), 1.30 (m, 6H), 1.20 (d, 3H, J=7), 0.93 (t, 3H, J=7), 0.88 (t, 3H, J=7).

M. (±)-(2R*,3S*)-2-Methyl-3-hydroxyhexanoate N-Heptanoylcysteamine Thioester

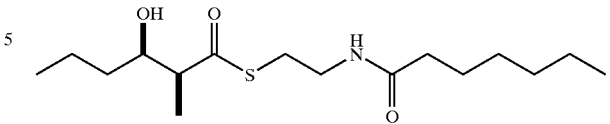

Prepared according to the method of paragraph A using N,S-diheptanoylcysteamine. $^{1}$H-NMR (CDCl$_{3}$): δ 5.83 (br s, 1H), 3.92 (m, 1H); 3.44 (m, 2H), 3.03 (m, 2H), 2.70 (dq, 1H, J=3, 7), 2.16 (m, 3H), 1.6 (m, 2H), 1.49 (m, 2H), 1.30 (m, 8H), 1.20 (d, 3H, J=7), 0.93 (t, 3H, J=7), 0.87 (t, 3H, J=7).

N. (±)-(2R*,3S*)-2-Methyl-3-hydroxyhexanoate N-Octanoylcysteamine Thioester

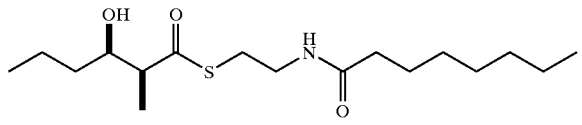

Prepared according to the method of paragraph A using N,S-dioctanoylcysteamine. $^{1}$H-NMR (CDCl$_{3}$): δ 5.79 (br s, 1H), 3.93 (m, 1H); 3.44 (m, 2H), 3.03 (m, 2H), 2.69 (dq, 1H, J=3, 7), 2.15 (m, 3H), 1.6 (m, 2H), 1.49 (m, 2H), 1.30 (m, 10H), 1.21 (d, 3H, J=7), 0.93 (t, 3H, J=7), 0.87 (t, 3H, J=7).

EXAMPLE 14

(±)-(2S*,3R*)-2-Vinyl-3-hydroxy-6-heptenoate N-Propionylcysteamine Thioester

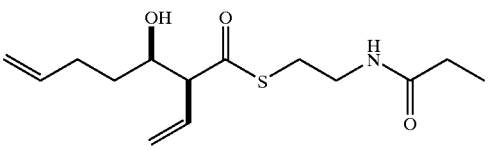

N,S-Dipropionyl cysteamine (4.28 g, 22.6 mmol, 1.00 eq) was dissolved in methanol (36 mL). A 25 wt % solution of sodium methoxide in methanol (3.89 mL, 17.0 mmol, 0.750 eq) was added dropwise. The solution was stirred for 15 min and then cooled to −78° C. A methanolic solution of the aldol adduct (6.50 g, 22.6 mmol, 1.00 eq in 9 mL of MeOH) was added dropwise. The reaction was stirred for 10 minutes at −78° C. and brought up to room temperature before quenching with solid oxalic acid (1.42 g). Volatiles were removed in vacuo. The residue was redissolved in ethyl acetate and washed with saturated NaHCO$_{3}$ followed by saturated CuSO$_{4}$. The organic layer was dried over MgSO$_{4}$, filtered, concentrated, and chromatographed on silica gel (1:1 hexanes:EtOAc) to give 5.61 g (87.0%) of a colorless oil. $^{13}$C-NMR (CDCl$_{3}$, 100 MHz): δ 200.97, 174.15, 137.88, 131.18, 121.63, 115.06, 71.02, 64.45, 38.97, 33.38, 29.83, 29.54, 28.83, 9.68.

EXAMPLE 15

Production of 6-Deoxyerythronolides

A. 15-Methyl-6-deoxyervthronolide B

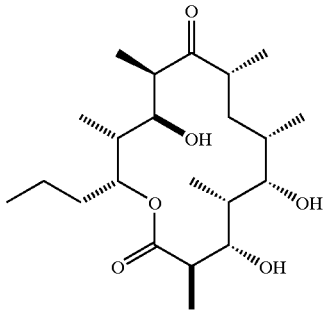

A seed culture of *Streptomyces coelicolor* K39-02/pJRJ2 was made by inoculating 1 mL of frozen mycelium into a 2.8 L baffled flask containing 500 mL of R2YE and shaking at 150–200 rpm/28–30° C. for 2 days. A 10 L stirred tank bioreactor was prepared, filled with 10 L, of FKA medium, autoclaved at 121° C. for 30 min., allowed to cool, and then inoculated with 400–500 mL of seed culture.

Temperature was maintained at 28–30° C. with agitation provided by 3 rushton impellers at 500–750 rpm, aeration at ~1 L/min., and pH controlled at 7.00 via automatic addition of 1 N NaOH or 1 N $H_2SO_4$. Glucose consumption, dissolved oxygen, pH, and cell mass were monitored. When the glucose concentration dropped below 0.1 g/L, the culture was supplemented with 10 g of (±)-(2R*,3S*)-2-methyl-3-hydroxyhexanoate N-propionylcysteamine thioester in 50 mL of DMSO. Controlled feeding of glucose maintained a glucose concentration of ~0.5 g/L. Titers of 15-methyl-6-deoxyerythronolide B were monitored by HPLC/MS, and the culture was harvested by centrifugation when the maximum titer was reached.

The 15-methyl-6-deoxyerythronolide B was purified by solid phase extraction. Fermentation broth was cooled to 4–15° C., and methanol was added to 10% (v/v). The broth was clarified by centrifugation and loaded onto an XAD-16 resin (Rohm and Haas) column (1 kg XAD/1 g 15-methyl-6-deoxyerythronolide B) at a flow rate of 2–4 mL/cm$^2$-min. The loaded resin was washed with 2 column volumes of 15% (v/v) methanol in water and the 15-methyl-6-deoxyerythronolide B was eluted from the resin with acetone and collected in ½ column volume fractions. The fractions containing 15-methyl-6-deoxyerythronolide B were identified by thin-layer chromatography (ethyl acetate-:hexanes 1:1) and HPLC/MS. The acetone fractions containing 15-methyl-6-deoxyerythronolide B were pooled, and the volatiles were removed under reduced pressure. The resulting aqueous mixture is extracted with ethyl acetate. The ethyl acetate extract was washed with saturated $NaH_2CO_3$ and brine solutions, dried over sodium or magnesium sulfate, filtered, and concentrated to dryness under reduced pressure. The crude material was purified by chromatography on silica gel using a gradient of hexanes and ethyl acetate. Fractions containing the product were pooled and concentrated to a pale yellow oil that spontaneously crystallized. Recrystallization from ether-hexane gave pure 15-methyl-6-deoxyerythronolide B. Mass spectrometry shows [M+H]=401. $^{13}$C-NMR (CDCl$_3$, 100 MHz): δ 213.57, 178.31, 79.51, 76.44, 74.47, 70.90, 43.95, 43.44, 40.88, 39.30, 37.66, 37.48, 35.52, 34.37, 19.45, 16.58, 14.68, 13.73, 13.23, 9.22, 6.87, 6.22.

B. 15-Fluoro-6-deoxyerythronolide B

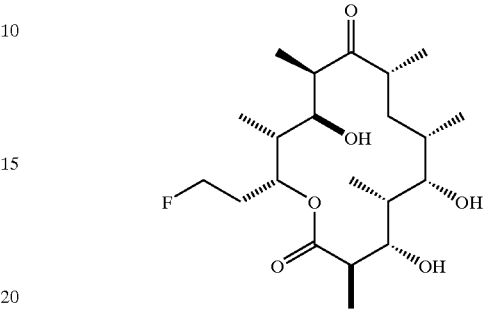

Prepared by feeding (2S,3R)-5-fluoro-3-hydroxy-2-methylpentanoate N-acetyl-cysteamine thioester to *S. coelicolor* CH999/pJRJ2 according to the method of paragraph A. The crude material was purified by silica gel chromatography using ethyl acetate/hexanes. APCI-MS: [M+H]=405. $^{19}$F-NMR (CDCl$_3$, 376 MHz): δ-222.0 (relative to CF$_3$CO$_2$H at δ-77.0). $^1$H-NNR (CDCl$_3$, 400 MHz): δ 5.49 (m, 1H); 4.94 (m, 2H); 3.99 (m, 1H); 3.90 (d, 1H, J=10); 3.84 (d, 1H, J=4); 3.70 (m, 1H); 3.18 (br s, 1H); 2.79 (m, 1H); 2.77 (m, 1H); 2.61 (m, 1H); 2.47 (br s, 1H); 2.20 (m, 1H); 2.00 (m, 1H); 1.92 (m, 1H); 1.85 (m, 1H); 1.70 (m, 1H); 1.65 (dd, 1H, J=4, 10); 1.29 (d, 3H, J=7); 1.24 (dd, 1H, J=4, 10); 1.07 (d, 3H, J=7); 1.06 (d, 3H, J=7); 1.05 (d, 3H, J=7); 1.02 (d, 3H, J=7); 0.93 (d, 3H, J=7). $^{13}$C-NMR (CDCl$_3$, 100 MHz): δ 213.70, 177.98, 80.68 (d, $J_{CF}$=167 Hz), 79.34, 76.37, 70.84 (d, $J_{CF}$=4 Hz), 70.74, 43.88, 43.27, 41.13, 39.54, 37.63, 37.52, 35.52, 33.34 (d, $J_{CF}$=20 Hz), 16.63, 14.60, 13.32, 9.20, 6.92, 6.28.

C. 14,15-Dehydro-6-deoxyerythronolide B

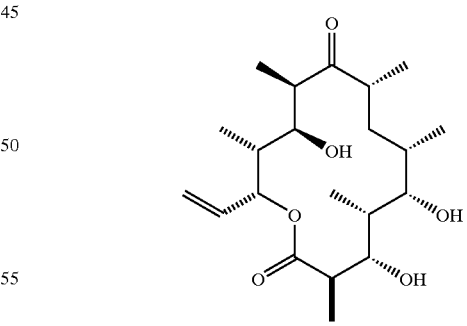

Prepared by feeding (2S,3R)-3-hydroxy-2-methyl-4-pentenoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=385. $^{13}$C-NMR (CDCl$_3$, 100 MHz): δ 213.67, 177.51, 134.80, 116.58, 79.40, 76.47, 74.11, 70.84, 43.80, 43.16, 41.48, 39.58, 37.61, 37.42, 35.56, 16.60, 14.55, 13.34, 9.20, 6.91, 6.30.0

D. 15-Chloro-6-deoxyerythronolide B

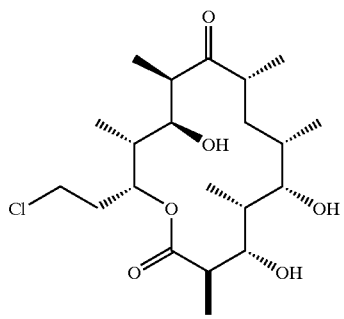

Prepared by feeding (±)-(2S*,3R*)-5-chloro-3-hydroxy-2-methylpentanoate N-acetylcysteamine thioester to *S. coelicolor* CH999/pJRJ2 according to the method of paragraph A. The crude material is purified by silica gel chromatography using ethyl acetate/hexanes. APCI-MS: [M+H]=421.

E. 15-Bromo-6-deoxyerythronolide B

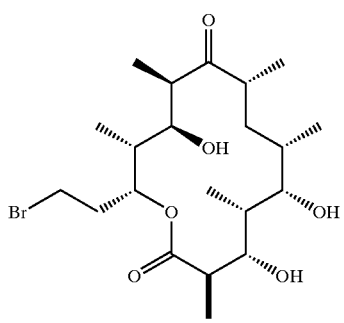

Prepared by feeding (±)-(2S*,3R*)-5-bromo-3-hydroxy-2-methylpentanoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=465, 467.

F. 15-Dimethyl-6-deoxyerythronolide B

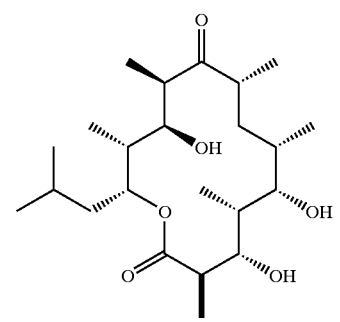

Prepared by feeding (±)-(2S*,3R*)-2,5-dimethyl-3-hydroxyhexanoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=415. $^{13}$C-NMR (CDCl$_3$, 100 MHz): δ 213.98, 178.35, 79.58, 76.41, 72.87, 71.01, 43.96, 43.48, 41.26, 41.16, 39.35, 37.65, 37.43, 35.43, 25.33, 22.99, 21.95, 16.58, 14.56, 13.21, 9.29, 6.90, 6.24.

G. 15-Phenyl-6-deoxyerythronolide B

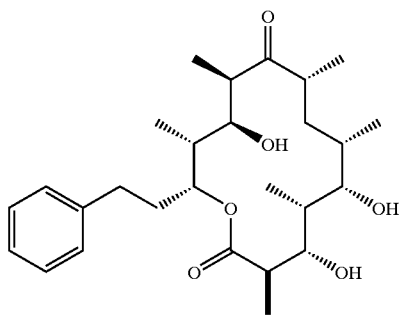

Prepared by feeding (±)-(2S*,3R*)-5-phenyl-3-hydroxy-2-methylpentanoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=463. $^{13}$C-NMR (CDCl$_3$, 100 MHz): δ 213.85, 178.30, 140.78, 128.55, 128.30, 126.23, 79.45, 76.37, 74.19, 70.90, 43.93, 43.37, 42.35, 41.04, 40.80, 39.47, 37.56, 37.56, 35.47, 34.41, 32.58, 16.65, 14.80, 13.28, 9.28, 6.95, 6.26.

H. 15-Ethyl-6-deoxyerythronolide B

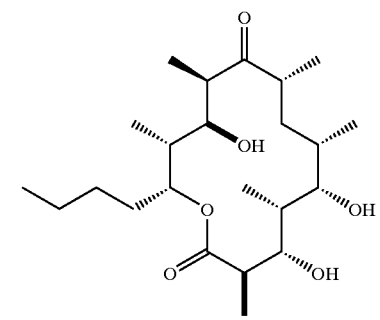

Prepared by feeding (±)-(2S*,3R*)-3-hydroxy-2-methylheptanoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=415. $^{13}$C-NMR (CDCl$_3$, 100 MHz): δ 213.65, 178.32, 79.51, 76.42, 74.74, 70.91, 43.95, 43.44, 40.84, 39.32, 37.65, 37.48, 35.50, 31.96, 28.37, 22.32, 16.58, 14.68, 13.93, 13.23, 9.20, 6.88, 6.23.

I. 15-Propyl-6-deoxyerythronolide B

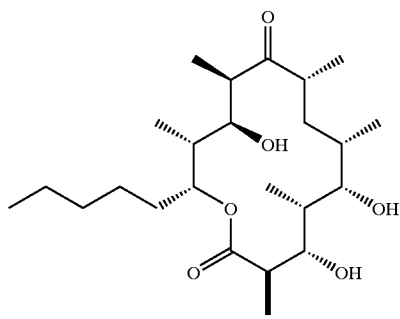

Prepared by feeding (±)-(2S*,3R*)-3-hydroxy-2-methyloctanoate N-acetylcysteamine thioester to *S. coelicolor* CH999/pJRJ2 according to the method of paragraph A. The crude material was purified by silica gel chromatography using ethyl acetate/hexanes. APCI-MS: [M+H]=429. 13C-NMR (CDCl3, 100 MHz): δ 213.66, 178.33, 79.51, 76.41, 74.76, 70.91, 43.95, 43.44, 40.85, 39.31, 37.65, 37.47, 35.50, 32.23, 31.38, 25.86, 22.48, 16.58, 14.68, 13.91, 13.22, 9.20, 6.88, 6.22.

J. 15-Ethenyl-6-deoxyerythronolide B

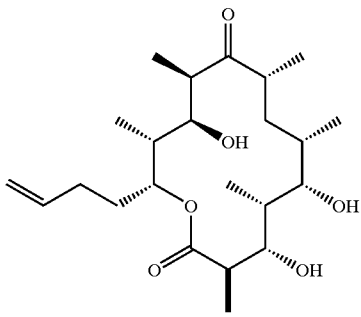

Prepared by feeding (±)-(2S*3R*)-3-hydroxy-2-methyl-6-heptenoate N-acetylcysteamine thioester to *S. coelicolor* CH999/pJRJ2 according to the method of paragraph A. The crude material was purified by silica gel chromatograp hy using ethyl acetate/hexanes. APCI-MS: [M+H]=413.

K. 13-Desesthyl-13-phenyl-6-deoxyerythronolide B

Prepared by feeding (±)-(2S*,3R*)-3-hydroxy-2-methylpropanoate N-acetylcysteamine thioester to *S. coelicolor* CH999/pJRJ2 according to the method of paragraph A. The crude material is purified by silica gel chromatography using ethyl acetate/hexanes. APCI-MS: [M+H]=435.

L. 12-Ethenyl-12-desmethyl-6-deoxyerythronolide B

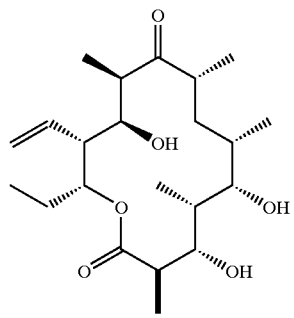

Prepared by feeding (2S,3R)-3-hydroxy-2-vinylpentanoate N-actylcysteamine thioester to *S. coelicolor* CH999/pJRJ2 according to the method of paragraph A. APCI-MS: [M+H]=398.

M. 12,15-Bisethenyl-12-desmethyl-6-deoxyerythronolide B

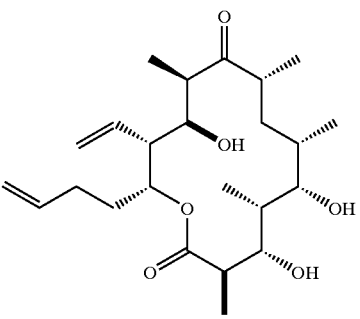

Prepared by feeding (2S,3R)-3-hydroxy-2-vinyl-6-heptenoate N-acetylcysteamine thioester to *S. coelicolor* CH999/pJRJ2 according to the method of paragraph A. APCI-MS: [M+H]=425.

N. 15-Azido-6-deoxyerythronolide B

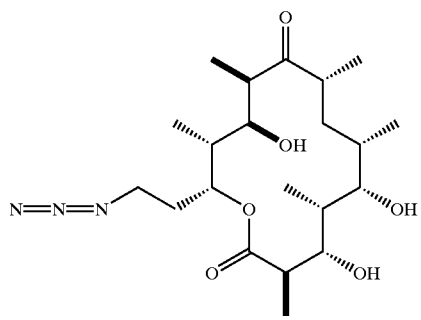

Prepared according to the method of Example Y using (2S*,3R*)-5-azido-2-methylpentanoate N-acetylcysteamine thioester. APCI-MS: [MH+]=429.

EXAMPLE 16

Derivatives of dEB

A. 12-Desmethyl-13-desethyl-12,13-(cyclohexenyl)-6-deoxyervthronolide B

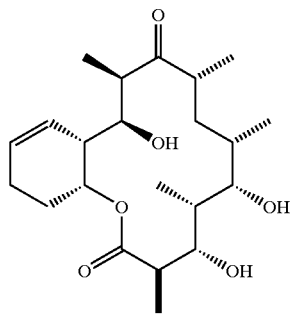

Prepared by treatment of 12,15-bisethenyl-12-desmethyl-6-deoxyerythronolide B with Grubbs' catalyst according to the procedure of Example 12.

B. 15-Bromo-14-hydroxy-6-deoxyerythronolide B

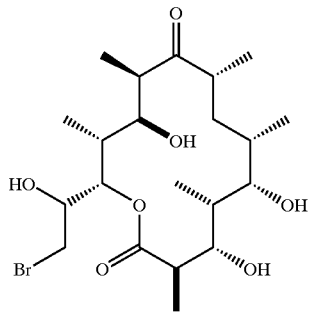

A solution of 14,15-dehydro-6-deoxyerythronolide B in aqueous acetonitrile is treated with N-bromosuccinimide. The mixture is evaporated to dryness, and the product is isolated by silica gel chromatography. $^{13}$C-NMR (CDCl$_3$, 100 MHz): δ 214.19, 175.82, 88.69, 81.52, 78.96, 77.46, 76.22, 49.43, 46.69, 43.76, 43.30, 38.50, 35.60, 34.30, 27.65, 18.06, 16.35, 15.53, 13.84, 13.06, 7.53.

EXAMPLE 17

Conversion of 6-Deoxyerythronolides into Erythromycins

A. Fermentations were conducted in 10 L (and 150 L) bioreactors. A 1 mL aliquot of frozen *Sac. erythraea* K40–67 mycelium was used to inoculate a seed culture in 500 mL of R2YE medium. The culture was shaken at 150–200 rpm/28–30° C. in a 2.8 L baffled Fernbach flask for ~48 hr. A 10 L stirred tank bioreactor was prepared, filled with 10 L of R2YE medium (70 L for the 150 L fermentation), autoclaved at 121° C. for 45 min., allowed to cool, and then inoculated with 200 mL (1.4 L for the 150 L fermentation) of seed culture. Temperature was maintained at 28–30° C. with agitation provided by 2 rushton impellers at 500–700 rpm, aeration at ~1 L/min., and pH controlled at 7.20 via automatic addition of 1 N NaOH or 1 N H$_2$SO$_4$. Foam was suppressed by addition of antifoam at 1 mL/L. The pH was controlled to avoid potentialproduct degradation into enol ether and spiroketal. Sucrose consumption, glucose evolution, dissolved oxygen, pH, and absorbance at 600 nm (cell mass) were monitored. After 24–36 hr., the culture was fed 300 mg (1.62 g for the 150 L fermentation) of a 6-dEB derivative compound dissolved in 3 mL (15 mL for the 150 L fermentation) of 100% ethanol. Fermentation continued for ~68–85 additional hr., and the fermentation broth was harvested by centrifugation. Titers of erythromycin A, B, C, and D analogs during the course of the fermentation were determined by electrospray MS analysis.

The erythromycins produced were purified by solid phase extraction. Fermentation broth was brought to pH 8.0 by addition of NaOH and chilled to 4–15° C. and ethanol was added (0.1 L/L broth). The broth was clarified by centrifugation and loaded onto an XAD-16 resin (Rohm and Haas) column (1 kg XAD/1 g erythromycin derivative) at a flow rate of 2–4 mL/cm$^2$-min. The loaded resin was washed with 2 column volumes of 15% (v/v) ethanol in water and the erythromycin derivative was eluted, from the resin with acetone and collected in ½ column volume fractions. The fractions containing the erythromycin derivative were identified by thin-layer chromatography and HPLC/MS.

The acetone fractions containing erythromycin analogs are pooled and the volatiles are removed under reduced pressure. The resulting aqueous mixture is extracted with ethyl acetate. The ethyl acetate extract is washed with saturated NaHCO$_3$ and brine solutions, dried over sodium or magnesium sulfate, filtered, and concentrated to dryness under reduced pressure. The crude material is dissolved in dichloromethane and loaded onto a pad of silica gel and washed with dichloromethane:methanol (96:4 v/v) until the eluent is no longer yellow. The desired material is then eluted with dichloromethane:methanol:triethylamine (94:4:2 v/v) and collected in fractions. Fractions containing erythromycin are identified by thin-layer chromatography, collected and concentrated under reduced pressure. This material is recrystallized from dichloromethane/hexanes.

B. 15-Fluoroerythromycin A

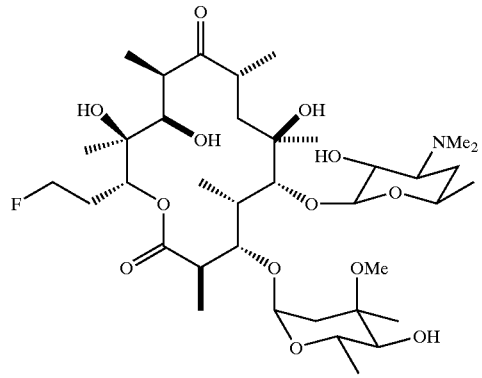

Prepared by feeding 15-fluoro-6-deoxyerythronolide B to *Sac. erythraea* according to the method of paragraph A. The crude material was purified by silica gel chromatography. APCI-MS: [M+H]=752. $^1$H NMR (400 MHz, CDCl$_3$): δ 5.27 (1H, dd, 10, 2 Hz); 4.87 (1H, d, 5); 4.53 (2H, dtd, 40, 6, <1); 4.41 (1H, d, 7); 3.98 (3H, m); 3.86 (1H, d, 1); 3.56 (1H, d, 7); 3.48 (1H, m); 3.31 (3H, s); 3.23, (1H, dd, 10, 7); 3.19 (1H, br s); 3.08 (1H, qd, 7, 1); 3.00 (1H, br s, 8); 2.84 (1H, qd, 7.1); 2.70 (1H, m); 2.46 (1H, 7, 4); 2.36 (1H, d, 16), 2.30 (6H, s); 2.03–1.95 (2H, m); 1.94 (1H, m); 1.73 (1H, br d, 15); 1.69 (1H, br d, 14); 1.57 (1H, m); 1.47 (3H, s); 1.28 (3H, d, 6); 1.24 (3H, s); 1.22 (3H, d, 6); 1.21 (1H, ovrlp); 1.17 (3H, d, 7); 1.15 (3H, d, ovrlp); 1.14 (3H, s); 1.14 (3H, d, ovrlp); 1.10 (3H, d, 7). $^{13}$C NMR (100 MHz, CDCl$_3$): δ 222.0, 175.4, 103.2, 96.3, 83.4, 82.3 (d, 170 Hz), 79.8, 77.9, 75.1, 74.3, 72.6, 72.5 (d, 4 Hz), 70.9, 68.9, 68.5, 65.6, 65.6, 49.5, 45.2, 44.8, 40.3, 39.6, 38.5, 37.7, 34.9, 29.5, 29.4 (d, 20 Hz), 28.7, 27.0, 21.5, 21.4, 18.6, 18.2, 16.1 15.3, 11.9, 9.1.

C. 15-Ethenylerythromycin A

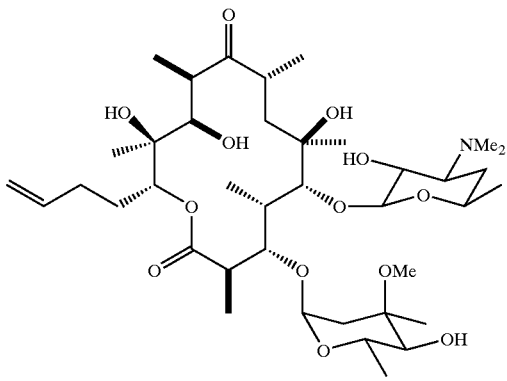

Is prepared by feeding 15-ethenyl-6-deoxyerythronolide B to *Sac. eythraea* according to the method of paragraph A. The crude material is purified by silica gel chromatography.

EXAMPLE 18

15-(2-(3-Quinolyl)ethyl)erythromycin A

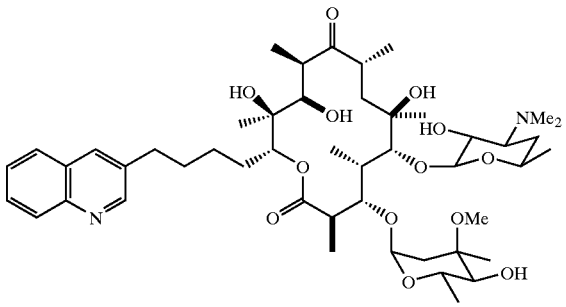

(1) A solution of 15-ethenylerythromycin A (1 mmol) in 5 mL of dichloromethane is treated with benzoic anhydride (1.5 mmol) and triethylamine (1.5 mmol) at ambient temperature for 30 hours. Aqueous 5% $Na_2CO_3$ is added and stirred for 30 minutes, then the mixture is extracted with dichloromethane. The organic extracts are combined, washed with saturated aqueous $NaHCO_3$ followed by brine, dried over $MgSO_4$, filtered, and evaporated. Chromatography on silica gel provides pure 2'-O-benzoyl-15-ethenylerythromycin A.

(2) A mixture of 2'-O-benzoyl-15-ethenylerythromycin A (1 mmol), palladium diacetate (0.2 mmol), tritolylphosphine (0.4 mmol), and 3-bromoquinoline (2 mmol) in 8 mL of deoxygenated acetonitrile is cooled to −78° C., degassed, and sealed in a reaction tube. The mixture is kept at 50° C. with stirring for 30 hours, then cooled and opened and the acetonitrile removed under vacuum. The residue is dissolved in ethyl acetate and washed successivelywith 5% aqueous $Na_2CO_3$, 2% aqueous Tris, and brine. After drying over $Mg_2SO_4$, the mixture is filtered and evaporated. Silica gel chromatography gives pure 2'-O-benzoyl-15-(2-(3-quinolyl) ethyl)erythromycin A.

(3) A solution of 2'-O-benzoyl-15-(2-(3-quinolyl)ethyl) erythromycin A (1 mmol) in methanol (10 mL) is heated at reflux for 6 hours, then evaporated. The residue is purified by silica gel chromatography to yield 15-(2-(3-quinolyl) ethyl)erythromycin A.

EXAMPLE 19

Preparation of Polystyrene-Supported 2-Benzimidazolone (1) A mixture of 2-hydroxybenzimidazole, 6-(acetylthio)-1-bromohexane, and triethylamine in acetonitrile is heated at reflux to prepare 1-(6-(acetylthio)hexyl)-2-benzimidazolone.

(2) A solution of 1-(6-(acetylthio)hexyl)-2-benzimidazolone in methanol is treated with one equivalent of sodium methoxide to prepare 1-(6-mercaptohexyl)-2-benzimidazolone.

(3) Merrifield resin (chloromethylated polystyrene-divinylbenzene) is suspended in dichloromethane by gentle stirring, and treated with 1-(6-mercaptohexyl)-2-benzimidazolone and triethylamine to prepare polystyrene-supported 2-benzimidazolone.

EXAMPLE 20

Preparation of Polystyrene-Supported (4S)-4-Benzyl-2-imidazolidinone (1) N-ethoxycarbonyl-(L)-phenylalinal is prepared from commercially-available N-ethoxycarbonyl-(L)-phenylalanine according to the method described for N-tbutoxycarbonyl-(L)-leucinal by O. P. Goel, et al., *Organic Syntheses* (1988) 67:69. This aldehyde is dissolved in methanol and treated with 1,4-diaminobutane, acetic acid, and sodium cyanoborohydride at 0° C. The resulting amine is isolated by chromatography, then heated under vacuum with removal of ethanol to provide (4S)-1-(4-aminobutyl)-4-benzyl-2-imidazolinone.

(2) Carboxypolystyrene resin is suspended by gentle stirring in dichloromethane and treated sequentially with 1-hydroxybenzotriazole and dicyclohexylcarbodiimide. After 30 minutes, (4S)-1-(4-aminobutyl)-4-benzyl-2-imidazolinone is added. The solution is checked periodically for disappearance of the amine. The resin is collected by vacuum filtration, washed with dichloromethane and dried.

EXAMPLE 21

General Solid-Phase Synthesis of (2S,3R)-2-Methyl-3-hydroxy-diketide Thioesters (1) Polystyrene-supported (4S)-4-benzyl-2-imidazolidinone is suspended in tetrahydrofuran and treated with excess propionic anhydride, triethylamine, and catalytic 4-dimethylaminopyridine overnight. The resin is collected by vacuum filtration and washed with water followed by acetone, then dried under vacuum to yield propionylated resin.

(2) The propionylated resin is suspended by shaking in anhydrous dichloromethane in a bottom-fritted reaction vessel under inert atmosphere and cooled to 0° C. A small molar excess of dibutylboron triflate is added and the vessel contents are shaken for 30 minutes. A small molar excess of triethylamine is added and the vessel contents are shaken for another 30 minutes. The liquid phase is drained from the vessel through the bottom frit using gas pressure, and is replaced with clean dichloromethane. containing a small molar excess of the aldehyde component. After shaking for 4 hours, the solvent is drained from the vessel via the frit and the resin is washed with clean dichloromethane. The resin is suspended in a mixture of phosphate buffer, pH 7, methanol, and $H_2O_2$ and shaken for 1 hour at 0° C. The solution is drained and the resin is washed sequentially with water, saturated NaHCO$_3$, water, methanol, and tetrahydrofuran, then dried under vacuum.

(3) An N-acylcysteamine is dissolved in tetrahydrofuran under inert atmosphere and cooled to −78° C. One molar equivalent of n-butyllithium is added, resulting in a white suspension. Addition of one molar equivalent of trimethylaluminum results in a clear solution of the aluminate salt. The resulting solution is added to the diketide-containing resin, and the mixture is shaken to release the diketide thioester. The solution is neutralized with oxalic acid, collected from the resin by vacuum filtration via the frit, and evaporated to dryness. The residue is resuspended in ethyl acetate and washed with saturated aqueous CuSO$_4$ followed by brine. After drying over MgSO$_4$, the solution is filtered and evaporated. Chromatography yields the purified diketide thioester.

EXAMPLE 22

Preparation of Polystyrene-Supported 2-Benzoxazolone (1) A mixture of chlorzoxazone, 3-(t-butoxycarbonylamino)-1-propene, palladium diacetate, tritolylphosphine, and acetonitrile is cooled to −78° C., degassed, and sealed in a reaction tube. The mixture is kept at 50° C. with stirring for 60 hours, then cooled and opened and the acetonitrile removed under vacuum. The residue is dissolved in ethyl acetate and washed successively with 5% aqueous NaHCO3 and brine. After drying over Mg2SO4, the mixture is filtered and evaporated. Silica gel chromatography gives 5-(3-(t-butoxycarbonylamino)-1-propenyl)-2-benzoxazolone.

(2) A solution of 5-(3-(t-butoxycarbonylamino)-1-propenyl)-2-benzoxazolone in trifluoroacetic acid is stirred at ambient temperature for 30 min, then evaporated to dryness to yield 5-(3-amino-1-propenyl)-2-benzoxazolone.

(3) Carboxypolystyrene resin is suspended by gentle stirring in dichloromethane and treated sequentially with 1-hydroxybenzotriazole and dicyclohexylcarbodiimide. After 30 minutes, 5-(3-amino-1-propenyl)-2-benzoxazolone is added. The solution is checked periodically for disappearance of the amine. The resin is collected by vacuum filtration, washed with dichloromethane and dried.

EXAMPLE 23

General Solid-Phase Synthesis of Racemic 2-Methyl-3-hydroxy-diketide Thioesters (1) Polystyrene-supported 2-benzoxazolone is suspended in acetone and treated with excess propionic anhydride and triethylamine overnight. The resin is collected by vacuum filtration and washed with water followed by acetone, then dried under vacuum to yield propionylated resin.

(2) The propionylated resin is suspended by shaking in anhydrous dichloromethane in a bottom-fritted reaction vessel under inert atmosphere and cooled to 0° C. A small molar excess of titanium tetrachloride is added and the vessel contents are shaken for 30 minutes. A small molar excess of triethylamine is added and the vessel contents are shaken for another 30 minutes. The liquid phase is drained from the vessel through the bottom frit using gas pressure, and is replaced with clean dichloromethane containing a small molar excess of the aldehyde component. After shaking for 4 hours, the solvent is drained from the vessel via the frit and the resin is washed with clean dichloromethane. The resin is washed with 1 N HCl to remove titanium residues, followed by water and methanol. This provides 2-methyl-3-hydroxy-diketides bound to polystyrene.

(3) An N,S-diacylcysteamine is dissolved in methanol and treated with one molar equivalent of methanolic sodium methoxide. The resulting solution is added to the diketide-containing resin, and the mixture is shaken to release the diketide thioester. The solution is neutralized with oxalic acid, collected from the resin by vacuum filtration via the frit, and evaporated to dryness. The residue is resuspended in ethyl acetate and washed with saturated aqueous CuSO$_4$ followed by brine. After drying over MgSO$_4$, the solution is filtered and evaporated. Chromatography yields the purified racemic diketide thioester.

EXAMPLE 24

15-(2-(3-Quinolyl)ethyl)-3-descladinosyl-3-oxo-6-O-methylerythromycin A 11,12-Cyclic Carbamate

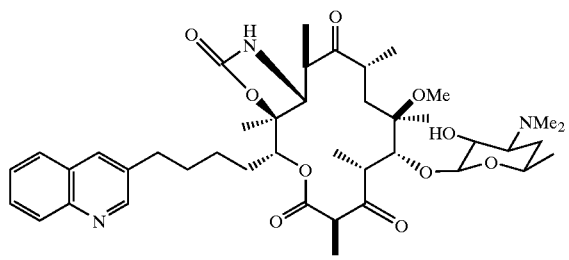

A. 15-(2-(3-Quinolyl)ethyl)erythromycin A-9-oxime 15-(2-(3-quinolyl)ethyl)erythromycin A (25.7 g, 28.9 mmol, 1.00 eq) is suspended in 42 mL of 2-propanol. Hydroxylamine (50 wt % in H$_2$O, 22.2 mL, 375 mmol, 13.0 eq) is added. The mixture is stirred until homogeneous. Glacial HOAc is added. The solution is stirred at 50° C. for 11 h. Saturated NaHCO$_3$ is added. The mixture is concentrated and extracted with CHCl$_3$ (4×400 mL); washed with NaHCO$_3$ and water. The combined aqueous layers are back-extracted with 400 mL CHCl$_3$. The combined organic phases are washed with brine, dried over Na$_2$SO$_4$, filtered, and concentrated to yield the crude material. This is carried on without further purification.

B. 15-(2-(3-Quinolyl)ethyl)erythromycin A-9-(Isopropoxycyclohexyl)oxime

The crude 15-(2-(3-quinolyl)ethyl)erythromycin A-9-oxime from above is dissolved in 72 mL of anhydrous CH$_2$Cl$_2$, and 1,1-diisopropoxycyclohexane (29.2 mL, 140 mmol, 4.86 eq) is added dropwise. A solution of pyridinium p-toluenesulfonate (10.5 g, 41.9 mmol, 1.45 eq) in CH$_2$Cl$_2$ (36 mL) is added dropwise. Dichloromethane (200 mL) is added after 15 h. The solution is washed with NaHCO$_3$ (2×100 mL) and water (100 mL). The combined aqueous phases are back-extracted with 100 mL CH$_2$Cl$_2$. The combined organic layers are washed with brine, dried over MgSO$_4$, filtered, and concentrated. The material is chromatographed over silica gel to give the desired product.

C. 2',4"-bis(O-Trimethylsilyl)-15-(2-(3-quinolyl)ethyl) erythromycin A-9-(Isopropoxycyclohexyl)oxime The 15-(2-(3-quinolyl)ethyl)erythromycin A-9-(isopropoxycyclohexyl)oxime (22.2 g, 21.3 mmol, 1.0 eq) is dissolved in 54 mL anhydrous CH$_2$Cl$_2$ and cooled in an ice/water bath. A mixture of chlorotrimethylsilane (4.05 mL, 31.9 mmol, 1.5 eq), N-(trimethylsilyl)-imidazole (7.81 mL, 53.2 mmol, 2.5 eq), and CH$_2$Cl$_2$ (18 mL) is added dropwise. The reaction is stirred for 15 minutes after complete addition and quenched with 600 mL EtOAc. The mixture is washed with sat. NaHCO$_3$ (2×200 mL), water (200 mL), and brine (200 mL). The organic layer is dried over MgSO$_4$, filtered, and concentrated to yield the crude product which was carried on without further purification.

D. 2',4"-bis(O-Trimethylsilyl)-6-O-methyl-15-(2-(3-quinolyl)ethyl)erythromycin A-9-(Isopropoxycyclohexyl)oxime Crude 2',4"-bis(O-trimethylsilyl)-15-(2-(3-quinolyl)ethyl)erythromycin A-9-(isopropoxycyclohexyl)oxime is dissolved in anhydrous tetrahydrofuran (41 mL) and cooled to 10° C. Anhydrous methylsulfoxide (41.4 mL) and methyl bromide (2.0 M in ether, 20.7 mL, 41.4 mmol, 2.0 eq) are added. A 1.0 M solution of potassium t-butoxide in THF (41.4 mL, 41.4 mmol, 2.0 eq) is diluted with anhydrous methylsulfoxide (41.4 mL). This is added to the reaction mixture at a rate of 0.5 eq/hr. The reaction is monitored by TLC (5:1 toluene:acetone). The reaction is quenched by the addition of ethyl acetate (200 mL) and sat. NaHCO$_3$ (70 mL). The mixture is transferred to a separatory funnel and diluted with 850 mL of ethyl acetate. The organic phase is washed with sat. NaHCO$_3$, water, and brine (300 mL each). The resulting emulsion is filtered through Celite. The separated organic phase is then dried over MgSO$_4$, filtered, and concentrated to give the crude product which is carried on without further purification.

E. 6-O-Methyl-15-(2-(3-quinolyl)ethyl)erythromycin A-9-oxime

The crude 2',4"-bis(trimethylsilyl)-6-O-methyl-15-(2-(3-quinolyl)ethyl)erythromycin A-9-(isopropoxycyclohexyl)oxime from above is dissolved in acetonitrile (110 mL). Glacial acetic acid (67 mL) diluted with water (55 mL) is added slowly. The solution is stirred 8 h. Toluene and 2-propanol are added, and the solution is concentrated. The product is then dissolved in toluene and concentrated twice to give the crude product which was carried on without further purification.

F. 6-O-methyl-15-(2-(3-quinolyl)ethyl)erythromycin A

The crude 6-O-methyl-15-(2-(3-quinolyl)ethyl)erythromycin A-9-oxime from above and sodium hydrosulfite (23.1 g, 113 mmol, 5.63 eq) are placed in a round-bottom flask equipped with a condenser and flushed with N$_2$. Ethanol (140 mL) and water (140 mL) are added. Formic acid (3.75 mL, 95.4 mmol, 4.77 eq) is added dropwise. The mixture is stirred at 80 C for 4.5 h. After the solution returned to room temperature, sat. NaHCO$_3$ was added. The pH is adjusted to 9–10 with 6 N NaOH. The mixture is then extracted with 3×400 mL of ethyl acetate. The combined organic phases are washed with sat. NaHCO$_3$ then water (250 mL each). The combined aqueous phases are back-extracted with ethyl acetate (400 mL). The combined organic phases are washed with brine, dried over MgSO$_4$, filtered, and concentrated to give the crude product which was carried on without further purification. Pure product can be obtained by chromatography on silica gel.

G. 6-O-Methyl-15-(2-(3-quinolyl)ethyl)-3-descladinosylerythromycin A

The crude 6-O-methyl-15-(2-(3-quinolyl)ethyl)erythromycin A is stirred in 280 mL of 0.5 M HCl for 3 h. The pH is adjusted to 9–10 with 6 N NaOH. The precipitate is collected by vacuum filtration and washed with water. The mother liquor is extracted with 3×400 mL ethyl acetate. The combined organic phases are washed with sat. NaHCO$_3$ and water. The combined aqueous phases are back-extracted with ethyl acetate. The combined organic phases are washed with brine, dried over MgSO$_4$, filtered, and concentrated. The combined product is chromatographed over silica gel the desired product as a white solid.

H. 2'-O-Acetyl-6-O-methyl-15-(2-(3-quinolyl)ethyl)-3-descladinosylerythromycin A 6-O-Methyl-15-(2-(3-quinolyl)ethyl)-3-descladinosyl erythromycin A (11.5 g, 15.5 mmol, 1.0 eq) is dissolved in 40 mL ethyl acetate. A solution of acetic anhydride (2.92 mL, 31.0 mmol, 2.0 eq) in ethyl acetate (35 mL) is added dropwise. The reaction is stirred for 30 min and then concentrated. The material is chromatographed over silica gel to give the desired product as a white solid.

I. 2'-O-Acetyl-3-descladinosyl-3-oxo-6-O-methyl-15-(2-(3-quinolyl)ethyl)erythromycin A 2'-O-Acetyl-6-O-methyl-15-(2-(3-quinolyl)ethyl)-3-descladinosyl erythromycin A (10 g, 12.8 mmol, 1.0 eq) and 1-[3-(dimethylamino)propyl]-3-ethylcarbodiimide hydrochloride (16.51 g, 86.1 mmol, 6.7 eq) are combined in a round-bottom flask and flushed with N$_2$. The solids are dissolved in anhydrous CH$_2$Cl$_2$ (64 mL) and cooled in an ice water bath. Anhydrous DMSO (15.5 mL, 218 mmol, 17 eq) is added. A solution of pyridinium trifluoroacetate (12.14 g, 62.9 mmol, 4.9 eq) in CH$_2$Cl$_2$ (47 mL) is added over 3 h. The solution is diluted with 600 mL of ethyl acetate and washed with sat. NaHCO$_3$, water, and brine (200 mL each). The organic phase is dried over MgSO$_4$, filtered, and concentrated. Chromatography over silica gel gives the desired product.

J. 2'-O-Acetyl-3-oxo-3-descladinosyl-11-methanesulfonyl-6-O-methyl-15-(2-(3-quinolyl)ethyl)erythromycin A 2'-O-Acetyl-3-descladinosyl-3-oxo-6-O-methyl-15-(2-(3-quinolyl)ethyl)erythromycin A is dissolved in freshly distilled pyridine (35 mL) and cooled in an ice water bath. Methanesulfonyl chloride is added dropwise. The reaction is allowed to come to ambient temperature and stirred overnight. Ethyl acetate (700 mL) is added, and the solution is washed with sat. NaHCO$_3$, water, and brine (200 mL each). The organic phase is dried over MgSO$_4$, filtered, and concentrated. Chromatography over silica gel gives the desired compound.

K. 2'-O-Acetyl-10,11-anhydro-3-descladinosyl-3-oxo-6-O-methyl-15-(2-(3-quinolyl)ethyl)erythromycin A 2'-O-Acetyl-3-oxo-3-descladinosyl-11-methanesulfonyl-6-O-methyl-15-(2-(3-quinolyl)ethyl)erythromycin A (6 g, 6.98 mmol, 1.0 eq) is dissolved in acetone (23 mL). 1,8-Diazabicyclo(5.4.0)undec-7-ene (5.22 mL, 34.9 mmol, 5.0 eq) is added dropwise. The reaction is stirred at ambient temperature for 4 h and then concentrated. Chromatography over silica gel gave the desired compound.

L. 3-Descladinosyl-3-oxo-6-O-methyl-15-(2-(3-quinolyl)ethyl)erythromycin A 11,12-Cyclic Carbamate A solution of 2'-O-Acetyl-10,11-anhydro-3-descladinosyl-3-oxo-6-O-methyl-15-(2-(3-quinolyl)ethyl)erythromycin A in dry tetrahydrofuran is added to a stirred suspension of NaH (3 eq.) in THF cooled to −10° C. To this is added a solution of carbonyldiimidazole (10 eq.) in THF/DMF (5:3), and the mixture is stirred for 2 hours. The reaction is warmed to ambient temperature and diluted with concentrated aqueous ammonia and stirred overnight. The mixture is diluted with ethyl acetate and washed with aq. NaHCO$_3$ and brine, dried over MgSO$_4$, and evaporated. Chromatography on silica gel yields the product.

The following provides additional products of the benzoxazolones.

A. Methyl (±)-(2S*,3R*)-3-Hydroxy-2-methylhexanoate

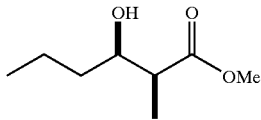

4-Dimethylaminopyridine (25 mg, 0.2 mmol) was added to a solution of (±)-N-[(2S*,3R*)-(2-methyl-3-hydroxyhexanoyl)]-2-benzoxazolone (263 mg, 1.0 mmol) in methanol (10 mL). The reaction mixture was stirred overnight and the methanol was removed at reduced pressure. The resulting oil was redissolved in ether (50 mL) and washed with 1 N sodium hydroxide (2×10 mL), 2 N HCl (10 mL), and brine (10 mL), dried with magnesium sulfate and concentrated at reduced pressure to give a clear oil (118 mg, 74%). $^1$H-NMR (CDCl$_3$, 400 MHz) δ 3.90 (m, 1H), 2.53 (dq, J=3, 3 Hz 1H), 2.45 (br s, 1H), 1.49 (m, 2H), 1.34 (m, 2H), 1.76 (d, J=7 Hz), 0.93 (t, J=7 Hz). $^{13}$C-NMR (CDCl$_3$, 100 MHz) δ 176.3, 71.4, 51.5, 44.3, 36.0, 19.0, 13.8, 10.6.

B. N-Benzyl (±)-(2S*,3R*)-3-Hydroxy-2-methylhexanamide

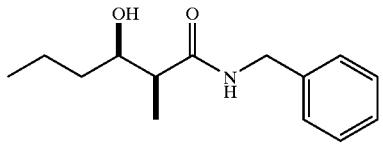

Benzylamine (0.6 mL, 5.5 mmol) is added dropwise to a solution of N-[(2S*,3R*)-3-hydroxy-2-methylhexanoyl]-2-benzoxazolinone (1.31 g, 5.0 mmol) in 10 mL of tetrahydrofuran. A mildly exothermic reaction ensues. After 15 min, the solvent is evaporated. The residue is redissolved in 50 mL of CH$_2$Cl$_2$ and washed successively with equal volumes of 1 N HCl, 1 N NaOH, water, and brine. After drying over MgSO4, the solution is evaporated to yield 1.12 g (95% yield) of the product as a white solid which was recrystallized from ethyl acetate/hexanes as white needles, mp 114–115° C. $^1$H-NMR (d$_6$-DMSO, 400 MHz) δ 8.27 (t, J=6, 1H), 7.30 (m, 2H), 7.22 (m, 3H), 4.49 (d, J=6, 1H), 4.27 (dd, J=6, 15, 1H), 4.20 (dd, J=6,15, 1H), 3.44 (m, 1H), 2.20 (q, J=7, 1H), 1.43 (m, 1H), 1.22 (m, 3H), 1.04 (d, J=7, 3H), 0.79 (t, J=7, 3H). $^{13}$C-NMR (d$_6$-DMSO, 100 MHz): 175.2, 140.2, 128.6, 127.6, 127.1, 71.8, 46.9, 42.2, 37.6, 19.0, 14.7, 14.5.

What is claimed is:

1. A racemic N-acylcysteamine thioester of the formula

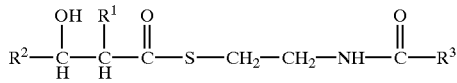

wherein
$R^1$ is methyl or vinyl;
$R^2$ is optionally substituted $C_1$–$C_5$ alkyl, or
$R^2$ is $C_2$–$C_4$ alkenyl, $C_2$–$C_4$ alkynyl, $C_3$ cycloalkyl, phenyl, 2-methylthiazolyl, tetrahydrofuryl, or pyridyl; and
$R^3$ is $C_1$–$C_7$ alkyl,
wherein said racemic N-acylcysteamine thioester has a (2R*,3S*) relative stereochemical configuration.

2. The racemic thioester of claim 1 wherein $R^2$ is alkyl optionally substituted with one or more cycloalkyl, halogen, alkoxy, alkylthio, azido, alkoxycarbonyl, phenyl, aryloxy, benzyloxy, arylthio, pyridyl, thiazolyl, or phthalimido groups.

3. The racemic thioester of claim 1 wherein $R^2$ is CH$_2$CH$_2$CH$_3$.

4. The racemic thioester of claim 1 wherein $R^2$ is CH═CH$_2$.

5. The racemic thioester of claim 1 wherein $R^2$ is CH$_2$CH$_2$CH═CH$_2$.

6. The racemic thioester of claim 1 wherein $R^2$ is CH$_2$CH$_2$F.

7. The racemic thioester of claim 1 wherein $R^2$ is CH$_2$CH$_2$Cl.

8. The racemic thioester of claim 1 wherein $R^2$ is CH$_2$CH$_2$N$_3$.

9. The racemic thioester of claim 1 wherein $R^3$ is ethyl.

10. The racemic thioester of claim 9 wherein $R^1$ is methyl.

11. The racemic thioester of claim 10 wherein $R^2$ is CH═CH$_2$.

12. The racemic thioester of claim 10 wherein $R^2$ is CH$_2$═CHCH$_2$CH$_2$.

13. The racemic thioester of claim 10 wherein $R^2$ is FCH$_2$CH$_2$.

14. The racemic thioester of claim 10 wherein $R^2$ is ClCH$_2$CH$_2$.

15. The racemic thioester of claim 10 wherein $R^2$ is N$_3$CH$_2$CH$_2$.

16. The racemic thioester of claim 10 wherein $R^2$ is CH$_3$CH$_2$CH$_2$.

17. The racemic thioester of claim 9 wherein $R^1$ is vinyl and $R^2$ is CH$_2$═CHCH$_2$CH$_2$.

* * * * *